United States Patent
Waksal et al.

(10) Patent No.: US 10,407,502 B2
(45) Date of Patent: Sep. 10, 2019

(54) IMMUNOMODULATORY AGENTS

(71) Applicant: KADMON CORPORATION, LLC, New York, NY (US)

(72) Inventors: Samuel D. Waksal, New York, NY (US); Zhenping Zhu, Woodcliff Lake, NJ (US); Yan Wu, Doylestown, PA (US); Stella Martomo, Edgewater, NJ (US); Zhaojing Zhong, Bronx, NY (US); Dan Lu, Montvale, NJ (US)

(73) Assignee: KADMON CORPORATION, LLC, New York, NY (US)

(*) Notice: Subject to any disclaimer, the term of this patent is extended or adjusted under 35 U.S.C. 154(b) by 260 days.

(21) Appl. No.: 15/111,102

(22) PCT Filed: Jan. 15, 2015

(86) PCT No.: PCT/US2015/011657
§ 371 (c)(1),
(2) Date: Jul. 12, 2016

(87) PCT Pub. No.: WO2015/109124
PCT Pub. Date: Jul. 23, 2015

(65) Prior Publication Data
US 2016/0340429 A1    Nov. 24, 2016

Related U.S. Application Data

(60) Provisional application No. 61/927,907, filed on Jan. 15, 2014.

(51) Int. Cl.
*C07K 16/28* (2006.01)
*C07K 14/54* (2006.01)
*C07K 14/715* (2006.01)
*A61K 47/68* (2017.01)
*A61K 39/00* (2006.01)

(52) U.S. Cl.
CPC ...... *C07K 16/2827* (2013.01); *A61K 47/6849* (2017.08); *C07K 14/5443* (2013.01); *C07K 14/7155* (2013.01); *A61K 2039/505* (2013.01); *C07K 2317/31* (2013.01); *C07K 2317/55* (2013.01); *C07K 2317/74* (2013.01); *C07K 2317/76* (2013.01); *C07K 2317/92* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 6,803,192 B1 | 10/2004 | Chen | |
| 6,808,710 B1 | 10/2004 | Wood et al. | |
| 6,936,704 B1 | 8/2005 | Freeman et al. | |
| 8,124,084 B2 | 2/2012 | Lefrancois et al. | |
| 8,981,063 B2 | 3/2015 | Chen | |
| 2009/0238791 A1* | 9/2009 | Jacques | C07K 14/5443 424/85.2 |
| 2011/0177074 A1 | 7/2011 | Sivakumar et al. | |
| 2012/0244118 A1 | 9/2012 | Berraondo Lopez et al. | |
| 2012/0251537 A1* | 10/2012 | Ahmed | A61K 39/12 424/134.1 |
| 2012/0276125 A1 | 11/2012 | Ast et al. | |

FOREIGN PATENT DOCUMENTS

| | | |
|---|---|---|
| EP | 1 537 878 A1 | 6/2005 |
| JP | 2012-511329 A | 5/2012 |
| JP | 2013-150606 A | 8/2013 |
| WO | 2004/004771 A1 | 1/2004 |
| WO | 2007/005874 A2 | 1/2007 |
| WO | 2010/077634 A1 | 7/2010 |
| WO | 2012/040323 A2 | 3/2012 |
| WO | 2012/175222 A1 | 12/2012 |
| WO | 2013/079174 A1 | 6/2013 |
| WO | 2013/181634 A2 | 12/2013 |

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Jones (Pharmacogenomics Journal, 1:126-134, 2001).*
Tosatto et al (Current Pharmaceutical Design, 12:2067-2086, 2006).*
Winkler et al (J. Imm., 265:4505-4514, 2000).*
Kermer et al., Combining antibody-directed presentation of IL-15 and 4-1BBL in a trifunctional fusion protein for cancer immunotherapy. Mol Cancer Ther, published online Nov. 6, 2013, vol. 13, No. 1, pp. 112-121. Especially abstract; p. 112, col. 2, para. 1.
Files, D.B., et al., "Blockade of the B7-H1/PD-1 Pathway for Cancer Immunotherapy" Yale J. of Bio and Med (2011); vol. 84; pp. 409-421.
Mortier, E. et al., "Soluble Interleukin-15 Receptor ? (IL-15R?)-sushi as a Selective and Protein Agonist of IL-15 Action through IL-15R?/?", J. Biol. Chem (2006); vol. 281:3; pp. 1612-1619.
Now, T. et al., "Clinical Significance and Therapeutic Potential of the Programmed Death-1 Ligand/Programmed Death-1 Pathway in Human Pancreatic Cancer", Clin. Cancer Res (2007); vol. 13:7; pp. 2151-2157.
Stoklasek, T. A., et al., "Combined IL-15/R? Immunotherapy Maximizes IL-15 Activity in Vivo", J. of Immunology (2006); vol. 177; pp. 6072-6080.

(Continued)

*Primary Examiner* — Brad Duffy
(74) *Attorney, Agent, or Firm* — Fox Rothschild LLP

(57) ABSTRACT

The invention provides antibodies that specifically bind to PD-L1 and fusion molecules comprising PD-L1 binding proteins constructed with an IL15 receptor-binding domain, nucleic acid molecules encoding the same, and therapeutic compositions thereof. The agents inhibit PD-L1-mediated immunosuppression and enhance cell and cytokine mediated immunity for the treatment of neoplastic and infectious diseases.

7 Claims, 30 Drawing Sheets
Specification includes a Sequence Listing.

(56) References Cited

OTHER PUBLICATIONS

Wei. X. et al., "The Sushi Domain of Soluble IL-15 Receptor ? is Essential for Binding IL-15 and Inhibiting Inflammatory and Allogenic Response in Vitro and in Vivo", J. Immunology; (2001); vol. 167; pp. 277-282.

Zhou, Q. et al., "Blockade of Programmed Death-1 Pathway Rescues the Effector of Tumor-Infiltrating T Cells and Enhances the Antitumor Efficacy of Lentivector Immunization", J. Immunology (2010); vol. 185; pp. 5082-5092.

Zitvogel, L. et al., "Targeting PD-1/PD-L1 Interactions for Cancer Immunotherapy", Onco Immunology (2012); vol. 1:8; pp. 1223-1225.

Kremer, V. et al., "An Antibody Fusion Protein for Cancer Immunotherapy Mimicking IL-15 Trans-Presentation at the Tumor Site"; Molecular Cancer Therapeutics (2012); vol. 11:6; pp. 1279-1288.

Muller, D. "Antibody-Cytokine Fusion Proteins for Cancer Immunotherapy: An Update on Recent Developments"; BioDrugs (2013); vol. 28; pp. 123-131.

Sznol, M. et al., "Antagonist Antibodies to PD-1 and B7-H1 (PD-L1) in the Treatment of Advanced Human Cancer"; Clinical Cancer Research (2013); vol. 19:5; pp. 1021-1034.

\* cited by examiner

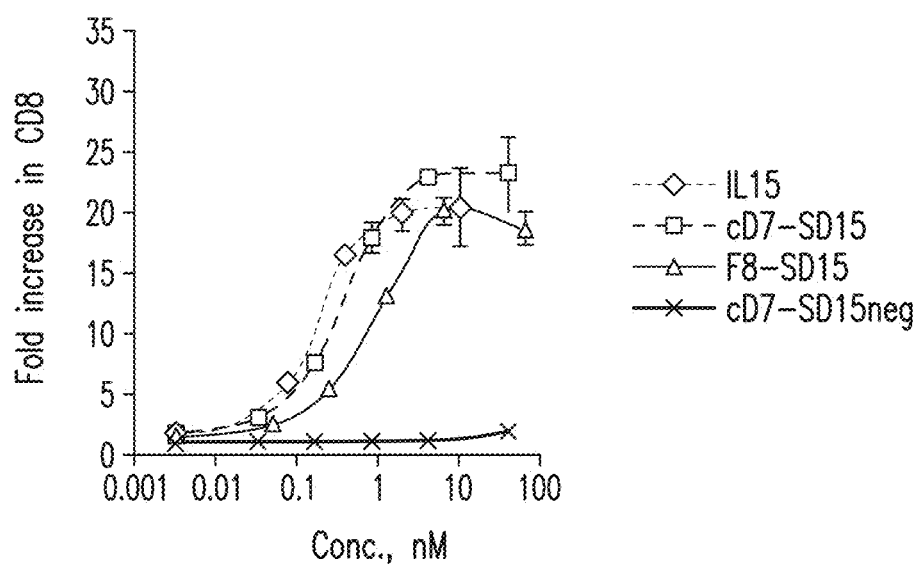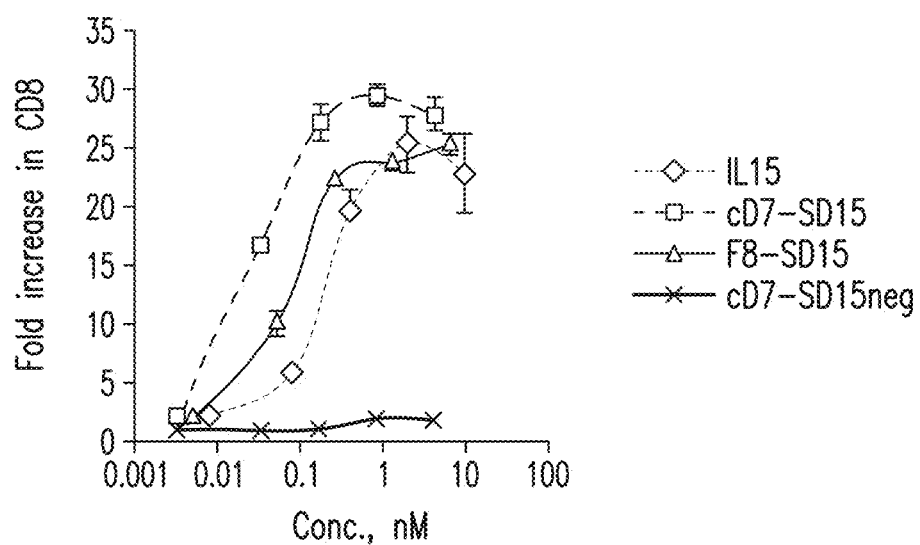
FIG. 11

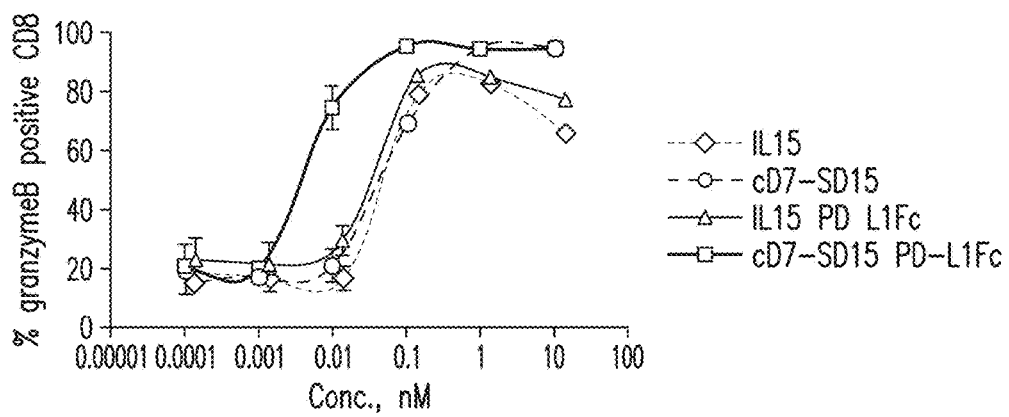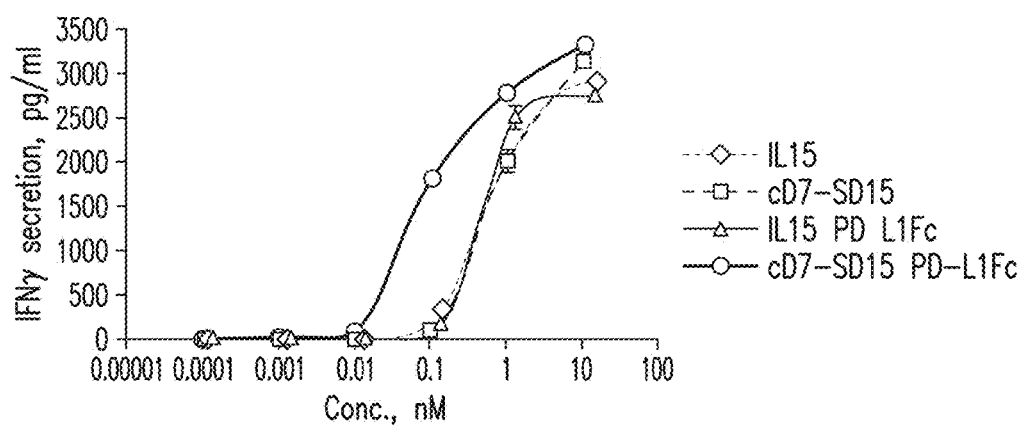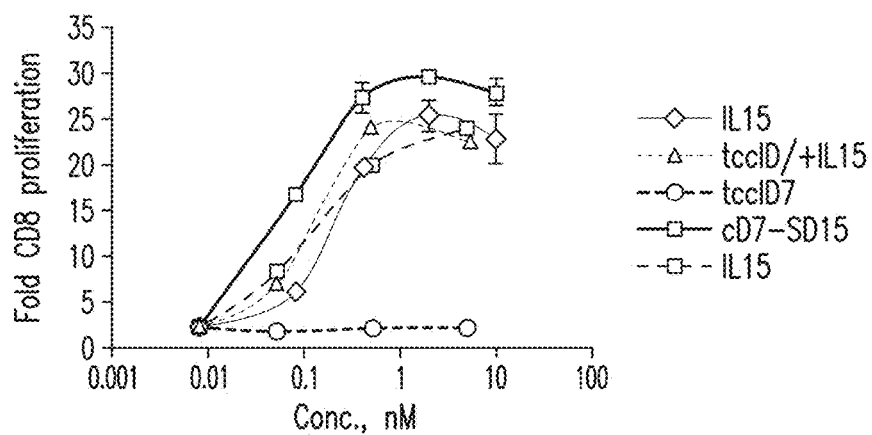
FIG. 12

FIG. 13A1

| Kabat No. | 1-25 (Framework) | 26-30 | 31-35, 35A, 35B (CDR1) | 36-43 |
|---|---|---|---|---|
| SEQ ID NO. 6 | EVQLLESGGGLVQPGGSLRLSCAAS | GFTFS | LYWMH - - | WVRQAPGK |
| SEQ ID NO. 16 | EVQLLESGGGLVQPGGSLRLSCAAS | GFTFS | PYPMW - - | WVRQAPGK |
| SEQ ID NO. 26 | EVQLLESGGGLVQPGGSLRLSCAAS | GFTFS | AYIMG - - | WVRQAPGK |
| SEQ ID NO. 36 | EVQLLESGGGLVQPGGSLRLSCAAS | GFTFS | MYWMA - - | WVRQAPGK |
| SEQ ID NO. 46 | EVQLLESGGGLVQPGGSLRLSCAAS | GFTFS | HYPMV - - | WVRQAPGK |
| SEQ ID NO. 56 | EVQLLESGGGLVQPGGSLRLSCAAS | GFTFS | EYVMI - - | WVRQAPGK |
| SEQ ID NO. 66 | EVQLLESGGGLVQPGGSLRLSCAAS | GFTFS | SYEMH - - | WVRQAPGK |
| SEQ ID NO. 76 | EVQLLESGGGLVQPGGSLRLSCAAS | GFTFS | RYGMG - - | WVRQAPGK |
| SEQ ID NO. 86 | EVQLLESGGGLVQPGGSLRLSCAAS | GFTFS | KYVMH - - | WVRQAPGK |
| SEQ ID NO. 96 | EVQLLESGGGLVQPGGSLRLSCAAS | GFTFS | WYPMH - - | WVRQAPGK |
| SEQ ID NO. 106 | EVQLLESGGGLVQPGGSLRLSCAAS | GFTFS | WYPMT - - | WVRQAPGK |
| SEQ ID NO. 116 | EVQLLESGGGLVQPGGSLRLSCAAS | GFTFS | WYLMK - - | WVRQAPGK |
| SEQ ID NO. 126 | EVQLLESGGGLVQPGGSLRLSCAAS | GFTFS | WYIMA - - | WVRQAPGK |
| SEQ ID NO. 136 | EVQLLESGGGLVQPGGSLRLSCAAS | GFTFS | SYQMG - - | WVRQAPGK |
| SEQ ID NO. 146 | EVQLLESGGGLVQPGGSLRLSCAAS | GFTFS | HYPMS - - | WVRQAPGK |
| SEQ ID NO. 156 | EVQLLESGGGLVQPGGSLRLSCAAS | GFTFS | RYEML - - | WVRQAPGK |
| SEQ ID NO. 166 | EVQLLESGGGLVQPGGSLRLSCAAS | GFTFS | PYDMG - - | WVRQAPGK |
| SEQ ID NO. 176 | EVQLLESGGGLVQPGGSLRLSCAAS | GFTFS | PYDMS - - | WVRQAPGK |
| SEQ ID NO. 186 | EVQLLESGGGLVQPGGSLRLSCAAS | GFTFS | PYGMR - - | WVRQAPGK |
| SEQ ID NO. 196 | EVQLLESGGGLVQPGGSLRLSCAAS | GFTFS | MYDMA - - | WVRQAPGK |
| SEQ ID NO. 206 | EVQLLESGGGLVQPGGSLRLSCAAS | GFTFS | SYRMI - - | WVRQAPGK |
| SEQ ID NO. 216 | EVQLLESGGGLVQPGGSLRLSCAAS | GFTFS | KYDMY - - | WVRQAPGK |
| SEQ ID NO. 226 | EVQLLESGGGLVQPGGSLRLSCAAS | GFTFS | SIYSMN - | WVRQAPGK |
| SEQ ID NO. 236 | EVQLLESGGGLVQPGGSLRLSCAAS | GFTFS | MYMMM - - | WVRQAPGK |
| SEQ ID NO. 246 | EVQLLESGGGLVQPGGSLRLSCAAS | GFTFS | AYRMV - - | WVRQAPGK |
| SEQ ID NO. 256 | EVQLLESGGGLVQPGGSLRLSCAAS | GFTFS | AYRMV - - | WVRQAPGK |

Sequence of IL-15Rα Sushi Domain and IL 15 Fusion Protein (called SD15)

human IL-15Rα Sushi domain (NM-802189)             IRD-11(exone3 encoded AA    linker
CPPPMSVEHADIWVKSYSLYSRERYICNSGFKRKAGTSSLTECVLNKATNVAHWTTPSLKC IRDPALVHQRPAPP SGGSGGGSGGGSGGGSGGGSLQ human IL-15 (NM_000585-3)
NWVRVISDLKKIEDLIQSMHIDATLYTESDVHPSCKVTAMKCFLLELQVISLESGDASIHDTVENLIILANNSLSSNGNVTESGCKECEELEEKNIKEFLQSFVHIVQMFINTS Sequence Example of Fusion Heavy Chain
Wild Type Fusion Heavy Chain Sequence with tccλD7 Variable Domain and SD15 (called tccλD7HC-SD15)
EVQLLESGGGLVQPGGSLRLSCAASGFTFSMYMRMWVRQAPGKGLEWVSSIYPSGGITFYADSVKGRFTISRDNSKNTLYLQMNSLRAEDTAIYYCARIKLGTVTTVDYWGQ
GTLVTVSS *(tccλD7 heavy chain variable domain)* ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRKEMTKNQVSLTCLVKGFYPSDIAVEWESNGQP ENNYKTTPPVLDSDGSFFLYSKLTVDKSRW
QQGNVFSCSVMHEALHNHYTQKSLSLSPG *(IgG1CH1-CH2-CH3 domain)* SCPPPMSVEHADIWVKSYSLYSRERYICNSGFKRKAGTSSLTECVLNKATNVAHWTTPSL
KCIRDPALVHQRPAPPSGGSGGGSGGGSGGGSGGGSLQNWVNVISDLKKIEDLIQSMHIDATLYTESDVHPSCKVTAMKCFLLELQVISLESGDASIHDTVENLIILANNSLSS
NGNVTESGCKECEELEEKNIKEFLQSFVHIVQMFINTS  *(IL-15Rα Sushi domain and IL-15)*

LALA Mutant Fusion Heavy Chain Sequence with tccλD7 Variable Domain and SD15 (called LALA mutant tccλD7HC-SD15)
EVQLLESGGGLVQPGGSLRLSCAASGFTFSMYMRMWVRQAPGKGLEWVSSIYPSGGITFYADSVKGRFTISRDNSKNTLYLQMNSLRAEDTAIYYCARIKLGTVTTVDYWGQGTLV
TVSS *(tccλD7 heavy chain
variable domain)*
ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCP
APEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQP *(LALA mutant*
REPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG *(LALA mutant*
*IgG1CH1-CH2-CH3 domain)* SCPPPMSVEHADIWVKSYSLYSRERYICNSG FKRKAGTSSLTECVLNKATNVAHWTTPSLKCIRDPALVHQRPAPPSGGSGGGSGGGSGGG
GSLQNWVNVISDLKKIEDLIQSMHIDATLYTESDVHPSCKVTAMKCFLLELQVISLESGDASIHDTVENLIILANNSLSSNGNVTESGCKECEELEEKNIKEFLQSFVHIVQMF
INTS  *(IL-15Rα Sushi domain and IL-15)*

FIG. 14

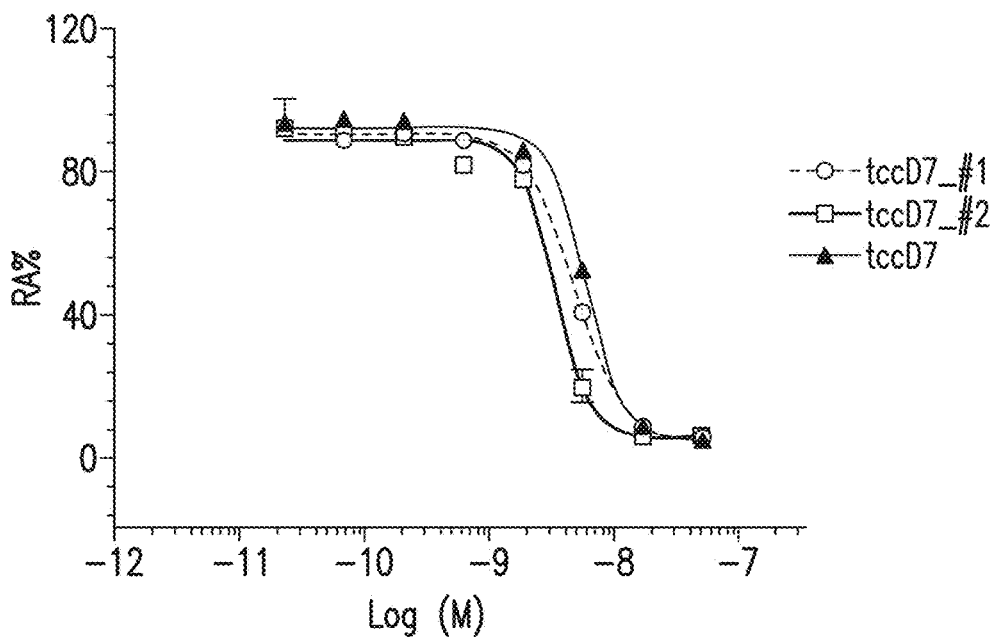
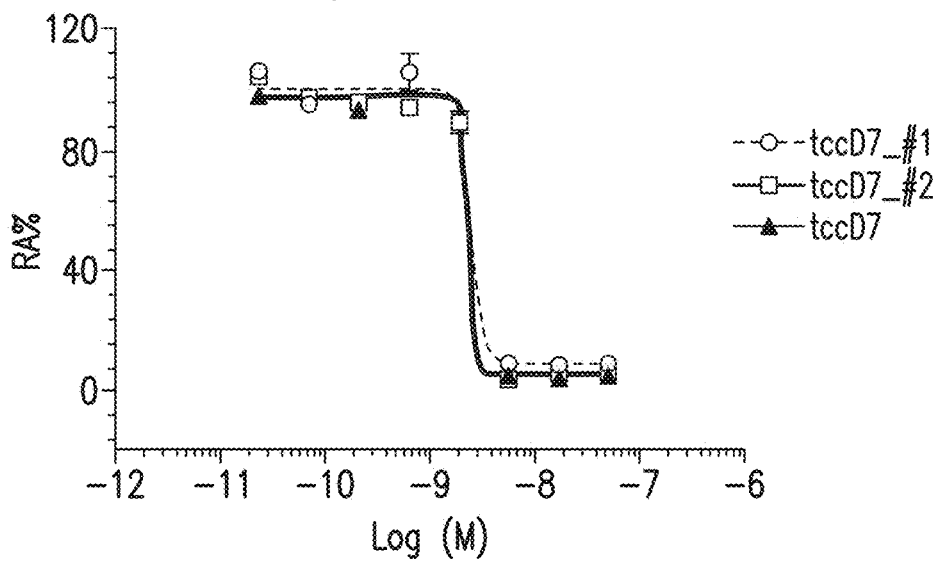
FIG. 18

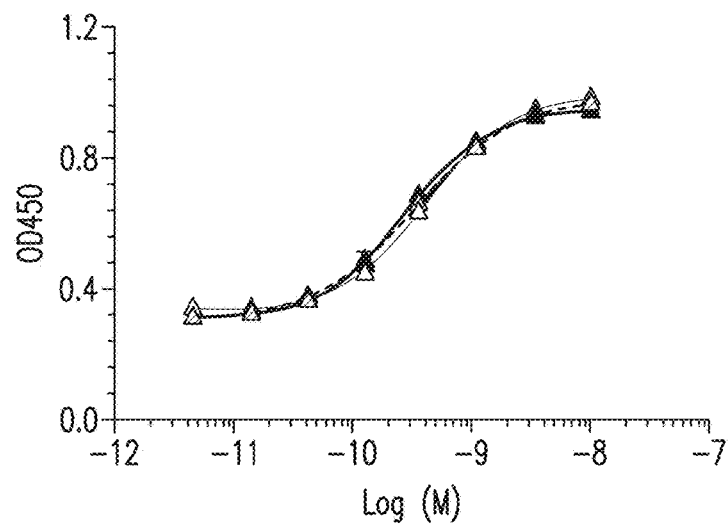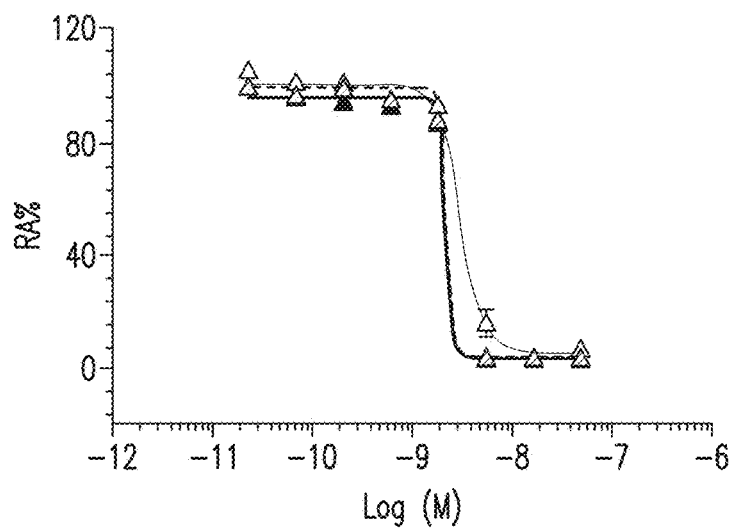
FIG. 23

IMMUNOMODULATORY AGENTS

CROSS-REFERENCE TO RELATED APPLICATIONS

This application claims priority to U.S. Provisional Application No. 61/927,907, filed Jan. 15, 2014, the content of which is incorporated herein by reference in its entirety.

FIELD OF THE INVENTION

The invention provides monoclonal antibodies that specifically bind to PD-L1 and bispecific fusion molecules comprising PD-L1 binding proteins constructed with IL15 and an IL15 receptor alpha sushi domain, nucleic acid molecules encoding the same, and therapeutic compositions thereof. The agents enhance T cell and NK cell function to increase cell and cytokine mediated immunity for the treatment of various immune dysfunction related disorders including cancers and infectious diseases.

BACKGROUND OF THE INVENTION

Programmed death 1 (PD-1) is a member of the CD28 family of receptors comprising CD28, CTLA-4, PD-1, ICOS, and BTLA (Freeman et al. (2000) J Exp Med 192: 1027-34; Latchman et al. (2001) Nat Immunol 2:261-8). PD-1 is an inducible immunosuppressive receptor mainly upregulated on activated T cells and B cells during the progression of immunopathological conditions. PD-1 interaction with its ligand PD-L1 results in the inhibition of TCR and BCR mediated proliferation and cytokine production and induction of apoptosis of antigen specific T cells through the intrinsic PD-1 mediated negative signaling of an immunoreceptor tyrosine-based inhibitory motif (ITIM) (Agata et al. (1996) Int. Immunol. 8:765, Unkeless and Jin. (1997) Curr. Opin. Immunol. 9:338-343, Okzaki et al. (2001) PNAS 98:13866-71, Dong et al. (2002) Nat. Med. 8:793-800). PD-L1 is a cell surface glycoprotein and a major ligand for PD-1. PD-L1 is also inducible on lymphoid tissues and non-lymphoid peripheral tissues following cellular activation. PD-L1 is upregulated in a variety of affected cell types including cancer and stromal cells in addition to immune cells, and plays an active role in immunosuppression during the course of the deterioration of diseases (Iwai et al (2002) PNAS 99:12293-7, Ohigashi et al. (2005) Clin Cancer Res 11:2947-53). PD-L1 upregulation has been linked to poor clinical outcomes in a variety of cancers and viral infection (Hofmeyer et al. (2011) J. BioMed. Biotech. 2011:1-9, McDermott and Atkins. (2013) Cancer Med. 2:662-73). The blockade of PD-1 or PD-L1 by antibody promoted CD8 T cell infiltration, CTL activity and increased presence of Th1 cytokine IFN-gamma in preclinical and clinical settings (Zhou et al. (2010) J. Immunol. 185:5082-92, Nomi et al. (2007) Clin Cancer Res. 13:2152-7, Flies et al. (2011) Yale J. Bio. Med. 48:409-21, Zitvogel and Kroemer. (2012) OncoImmunol. 1:1223-25). PD-L1 antibody as an immunomodulating agent has been shown to be efficacious when used as monotherapy or combined with antibodies to other immunosuppressive molecules.

However, the immunomodulating intervention to immunosuppressive factors only partially resolves the problems associated with impaired immunity in cancer, infection, and other diseases. It is still highly desirable to utilize biotherapeutic agents to directly stimulate and expand effector immune cells for lifting weakened innate and adaptive immune response to a more effective level to control tumor and infection. Immunotherapy using cytokines including interleukins, i.e. IL-2, IL-12, IL15, IL-21, and TNFα, GM-CSF, etc., has been shown to be efficacious to some extent in the treatment of cancer and infection, but clinical outcome is often limited by systemic toxicity associated with the high blood concentrations of cytokine that need to obtain efficacy and lack of specificity of target in affected cells and tissues.

Among assessed cytokines, IL15 has been recognized to be dedicated to stimulate effector and central memory CD8 T cells composing of a subset of antigen specific CD8 cells to exert antitumor immunity without modulating effects on other T cell populations. Moreover, unlike IL-2 that activates Treg, IL15 has been shown to have capacity to rescue T cells from apoptosis induced by Treg and other immunosuppressive cells in addition to its ability to activate natural killer (NK) cells and effector and memory CD8 T cells (Van Belle et al. (2012) PLoS One 7:e45299, Obar and Lefrancois. (2010) J. Immunol. 185:263-72, Pelletier and Girard. (2006) J Immunol 177:100-108, Elpek et al. (2010) PNAS 107:21647-21652).

IL15 was identified as a γc cytokine in 1994 based on its ability to stimulate the proliferation of the murine T cell line CTLL-2 (Grabstein et al. (1994) Science 264:965-8, Bamford et al. (1996) PNAS 93:2897-902). Human IL15 shares approximately 97% and 96% amino acid sequence identity with simian and cynomolgus IL15, respectively. Human and mouse IL15 have 73% homology and are comparably active on mouse cells. IL15 is a 12.5 KD protein (114 amino acids), secreted by DC, macrophage and granular cells as a 14-15 kDa glycoprotein, and also a member of the four α-helix bundle-containing cytokines (Andderson et al. (1995) J Biol Chem. 270:29862-9, Steel et al. (2012) Trends Pharmacol. Sci. 33:35-41). IL15 is typically formed a complex with IL15 receptor alpha expressed on APCs prior to binding to functional IL15 receptor beta and gamma units on T cells and NK cells. IL15 may be presented in trans to responsive cells expressing CD122 and CD132 by cells expressing the cytokine itself bound to a membrane form of the receptor alpha chain (Dubois et al. (2002) Immunity 17:537-47). IL15 receptor alpha sushi domain (29.5 KD in size) is a critical component to form a complex with IL15 prior to properly engagement with receptor β and γ (Wei et al. (2001) J. Immunol. 167:277-82). IL15 and IL15Rα complex and IL15/IL15Rα sushi domain fusion protein were reported to be highly potent to stimulate CD8 T cells and NK cells in vitro and in vivo compared to IL15 alone (Mortier et al. (2005) J Biol Chem. 281:1612-19, Stoklasek et al. (2006) J. Immunol. 177:6072-80). IL15 also induces the proliferation and differentiation of stimulated human B cells (Armitage et al. (1995) J Immunol. 154:483-90). It was suggested that IL15 mostly opposed activation-induced cell death (AICD) by acting to prolong the survival of T lymphocytes (Marks-Konczalik et al. (2000) PNAS 97:11445-50). IL15 has an exceptional ability to support the maintenance of NK cells and memory phenotype and antigen specific memory CD8 T cells (Ma et al. (2006) Annu Rev Immunol. 24:657-79). Thus, among most active cytokines in immunomodulation, IL15 has an unique capacity to mediate many important aspects of immunity against a variety of tumor types and viral infection including HIV, HBV, HCV, LCMV, etc (Steel et al. (2012) Trends Pharmacol. Sci. 33:35-41, Verbist and Klonowski, (2012) Cytokine. 59:467-478).

SUMMARY OF THE INVENTION

The present invention provides antibodies and binding proteins that bind to PD-L1. In certain embodiments of the invention, the antibodies bind to PD-L1 and block interaction with PD-1. By blocking the interaction of PD-L1 with PD-1, such antibodies are useful to reduce or inhibit immunosuppression.

In another aspect, the invention provides antibodies and binding proteins that bind specifically to PD-L1 and at least one other molecule. Examples of such embodiments include PD-L1 binding proteins that also bind to one or more other ligands and/or receptors, which may be membrane bound or soluble.

In another aspect, the invention provides molecules, such as fusion proteins that bind PD-L1 that, apart from reducing or inhibiting immunosuppression by binding to PD-L1, also promote one or more immune responses by interaction with other ligands or receptors. In an embodiment of the invention, the molecule binds to PD-L1 on target cells, and also stimulates a cell-mediated immune response, for example, by promoting proliferation of T cells and/or NK cells. In an embodiment of the invention, the molecule stimulates cells that respond to an interleukin or an interferon, such as, without limitation, IL2, IL7, IL15, and IL21. In an embodiment of the invention, the molecule includes a sequence or domain that promotes IL15 stimulation of the IL15 receptor (IL15R). In an embodiment of the invention, the molecule that promotes IL15R stimulation is a portion of the IL15R alpha chain comprising a sushi domain. In an embodiment of the invention, the molecule provides the sushi domain of the IL15R alpha chain. In an embodiment of the invention, the molecule provides a complex of IL15 and the sushi domain of the IL15R alpha chain, which may be covalent or non-covalent. The experiments disclosed herein demonstrate that single molecules containing both a PD-L1 binding domain that blocks binding or PD-L1 to PD-1, and an IL15R stimulating domain, promote a better immune response than separate molecules used together. More particularly, providing a molecule that provides an anti-PD-L1 antibody domain as well as a hybrid domain comprising IL15 and the IL15 alpha chain sushi domain, promoted increased proliferation, Th1 cytokine release, and killing activity-related molecules of NK and T cells, compared to providing the domains in separate molecules.

In one embodiment, the invention provides an antibody or fragment that binds to PD-L1, which comprises a heavy chain CDR-1H which has the sequence $X_1YX_2MX_3$ (SEQ ID NO:328) wherein $X_1$ is A, G, M, Q, S, Y, or W, $X_2$ is A, L, M, Q, R, S, V, W, or Y, and $X_3$ is A, F, L, M, S, T, V, or Y, a heavy chain CDR-2H which has SEQ ID NO:243, and a heavy chain CDR-3H which has the sequence of SEQ ID NO:245. In certain such embodiments, the heavy chain CDR-1H has a sequence selected from SEQ ID NO:241, SEQ ID NO:264, SEQ ID NO:266, SEQ ID NO:268, SEQ ID NO:270, SEQ ID NO:272, SEQ ID NO:274, SEQ ID NO:276, SEQ ID NO:278, SEQ ID NO:280, SEQ ID NO:282, SEQ ID NO:284, SEQ ID NO:286, SEQ ID NO:288, SEQ ID NO:290, SEQ ID NO:292, SEQ ID NO:294, SEQ ID NO:296, SEQ ID NO:298, SEQ ID NO:300, SEQ ID NO:302, SEQ ID NO:304, SEQ ID NO:306, SEQ ID NO:308, SEQ ID NO:310, and SEQ ID NO:312. In such embodiments, the heavy chain variable domain is at least 80%, or at least 85%, or at least 90%, or at least 95% identical to SEQ ID NO:246. The antibodies may further comprise a light chain variable domain which comprises a CDR-1L which has SEQ ID NO:247, a CDR-2L which has SEQ ID NO:248, and a CDR-3L which has SEQ ID NO:249. In some such embodiments the light chain variable domain is at least 80%, or at least 85%, or at least 90%, or at least 95% identical to SEQ ID NO:250. In another embodiment, the invention provides an antibody or fragment thereof that binds to PD-L1, wherein the light chain comprises a CDR-1L which has SEQ ID NO:247, a CDR-2L which has SEQ ID NO:248, and a CDR-3L which has SEQ ID NO:249.

The invention also provides conjugates of the antibodies, for example, and without limitation, to imaging agents, therapeutic agents, or cytotoxic agents.

The invention further provides compositions comprising the antibodies and conjugates and a pharamaceutically acceptable carrier.

In another aspect, the invention provides a fusion protein capable of binding to PDL1, which also stimulates an immune response mediated by, for example, a T cell or an NK cell. In an embodiment of the invention, the fusion protein includes a portion that binds to IL15 receptor. In other emodiments, the fusion protein includes a portion that binds to, e.g., an interleukin receptor or an interferon receptor. In an emodiement of the invention, the portion of the fusion protein that binds to PD-L1 is an antibody or PD-L1 binding fragment thereof. In an embodiment of the invention, the IL15 receptor-binding portion is IL15, whose binding may be enhanced by the presence in the fusion protein of an IL15R alpha sushi domain.

The invention provides a method of inhibiting the interaction of PD1 with PD-L1 in a subject, which comprises administering an effective amount of an antibody or fragment of the invention. The invention further provides a method of inhibiting immunosuppression mediated by PD-L1 which comprises administering an effective amount of the antibody or fragment of the invention, or a fusion protein of the invention.

The invention further provides a method of stimulating an immune response against a cell or tissue that expresses PD-L1, which comprises administering to a subject an effective amount of the antibody or fragment of the invention, or a fusion protein of the invention. In certain embodiments, the cell or tissue the expresses PD-L1 is a neoplastic cell or an infected cell.

BRIEF DESCRIPTION OF THE FIGURES

FIG. 11 shows anti-PD-L1-SD15 fusion proteins function to activate CD8 similarly to IL15 when added to in vitro CD8 stimulation in the presence of αCD3 coated beads (A). However, in the presence of αCD3 and PD-L1Fc coated beads, anti-PD-L1-SD15 fusion proteins can increase CD8 proliferation by more than five-fold when compared to IL15 (B). cD7-SD15neg is anti-PD-L1 cD7 with non-functional IL15 serving as negative controls.

FIG. 12 shows CD8 activation in the presence of PD-L1Fc on the antigen presenting cells. Anti-PD-L1-SD15 fusion protein cD7-SD15 stimulated CD8 at significantly lower concentrations as measured by (A) percent increase in granzymeB positive CD8, and (B) increased in total cytokine secretions. The maximum levels of CD8 activation were also increased in CD8 activated by αCD3 and PD-L1Fc with addition of cD7-SD15 as compared to IL15. (C) Data on CD8 proliferation in the presence of both anti-PD-L1 antibody and free IL15 (dotted lines) is superimposed on data of CD8 proliferation in presence of anti-PD-L1-SD15 fusion protein (straight lines).

Figure 13A2:
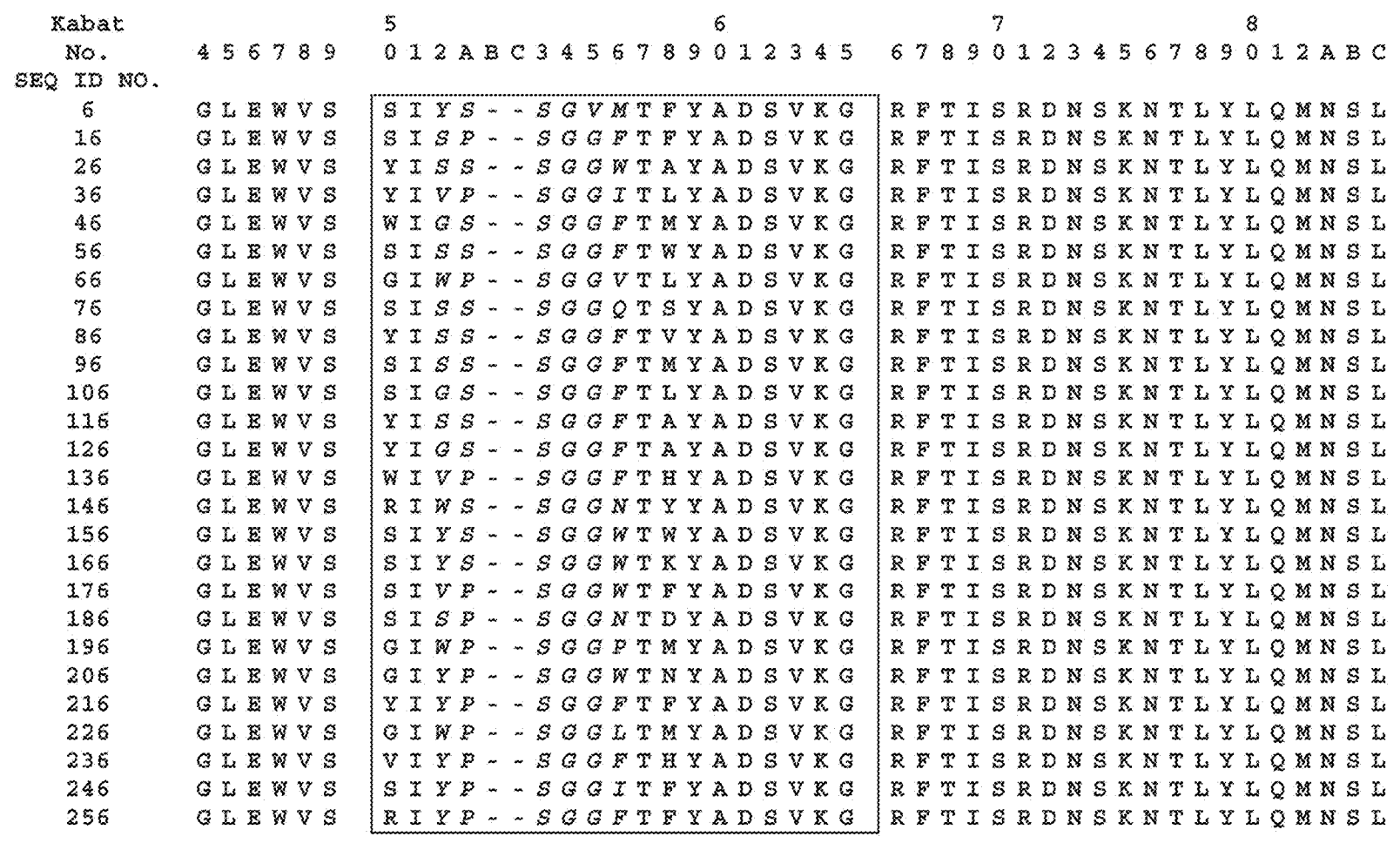
Figure 13A3:
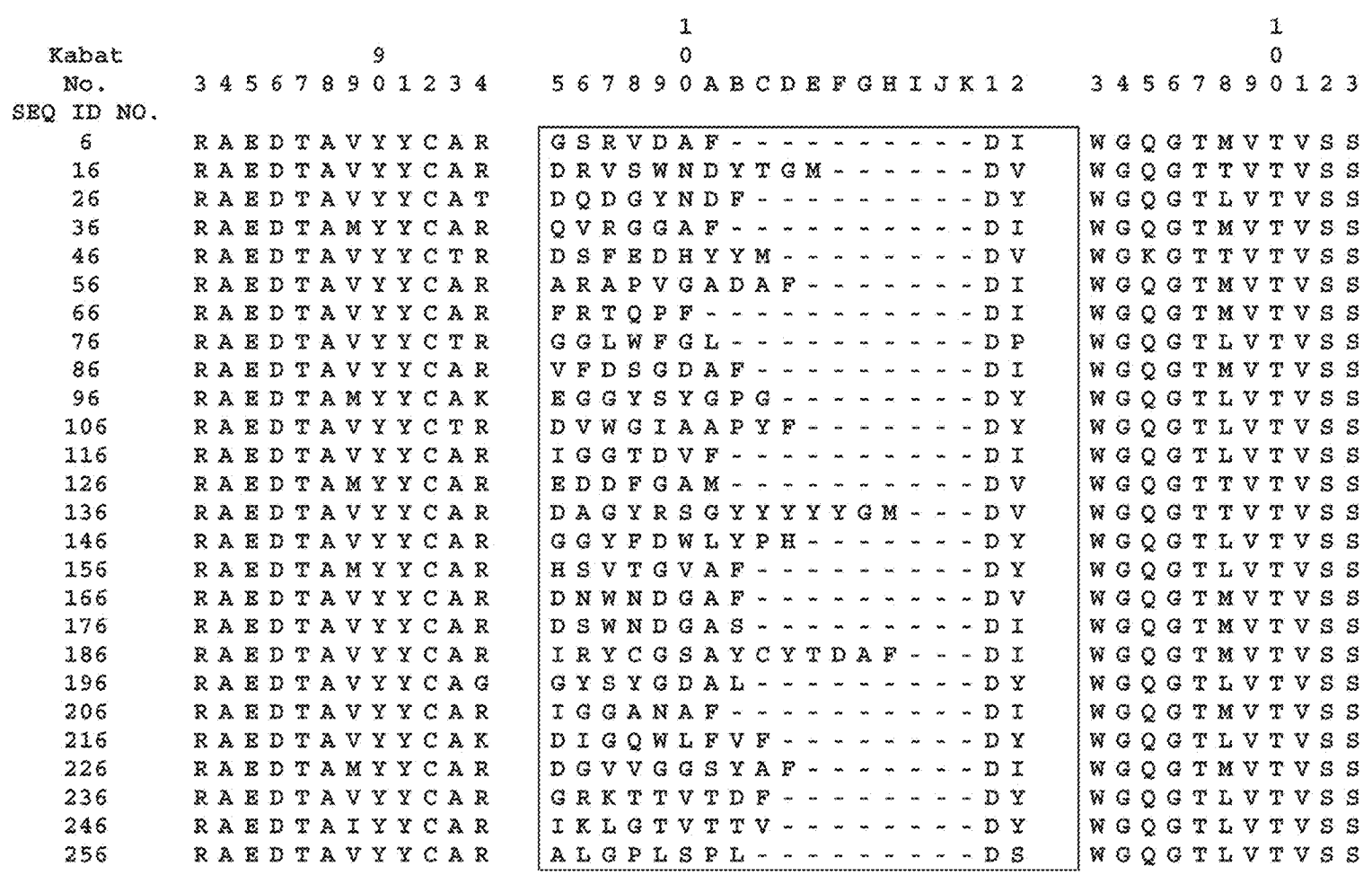
Figure 13B1:
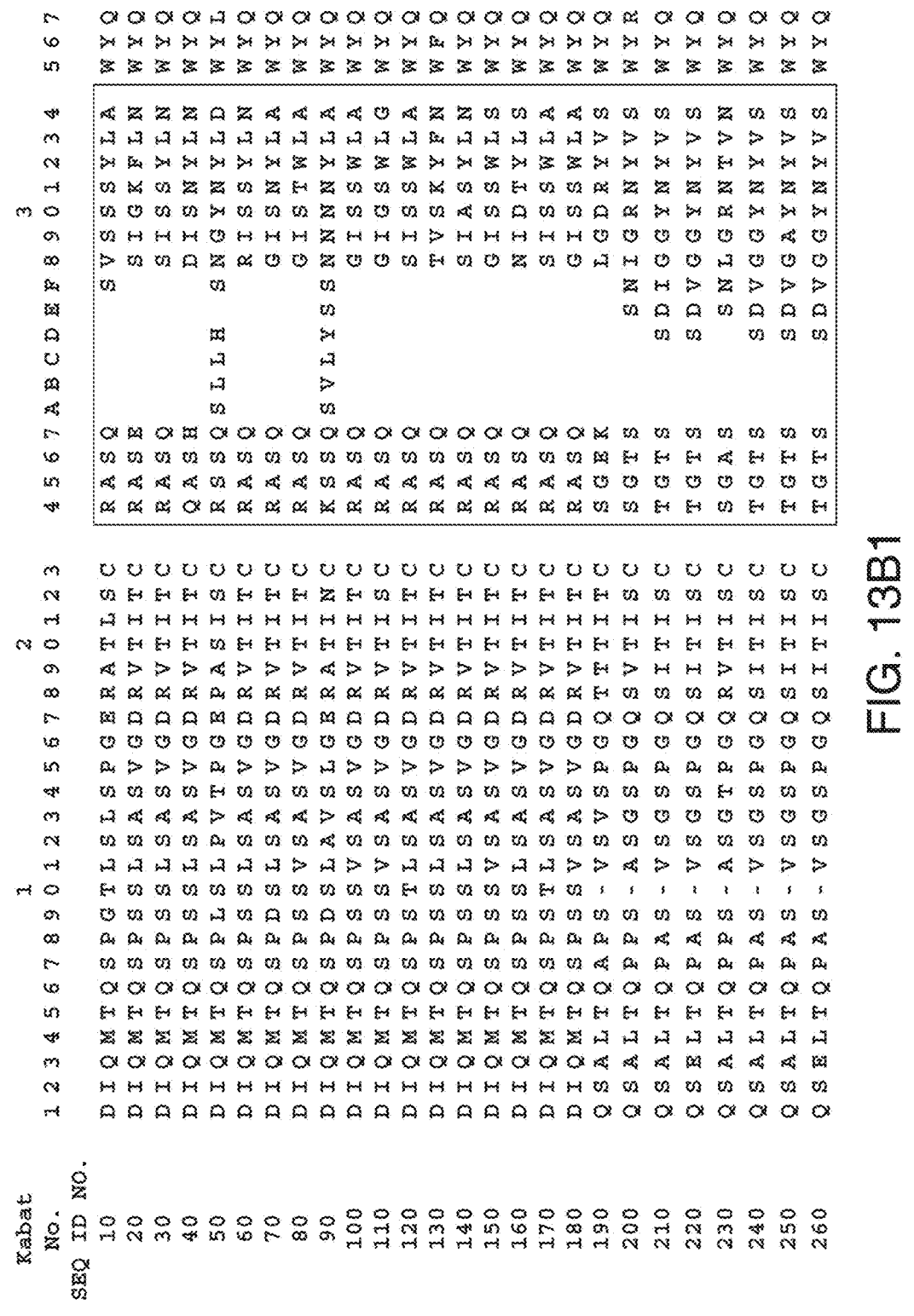
Figure 13B2:
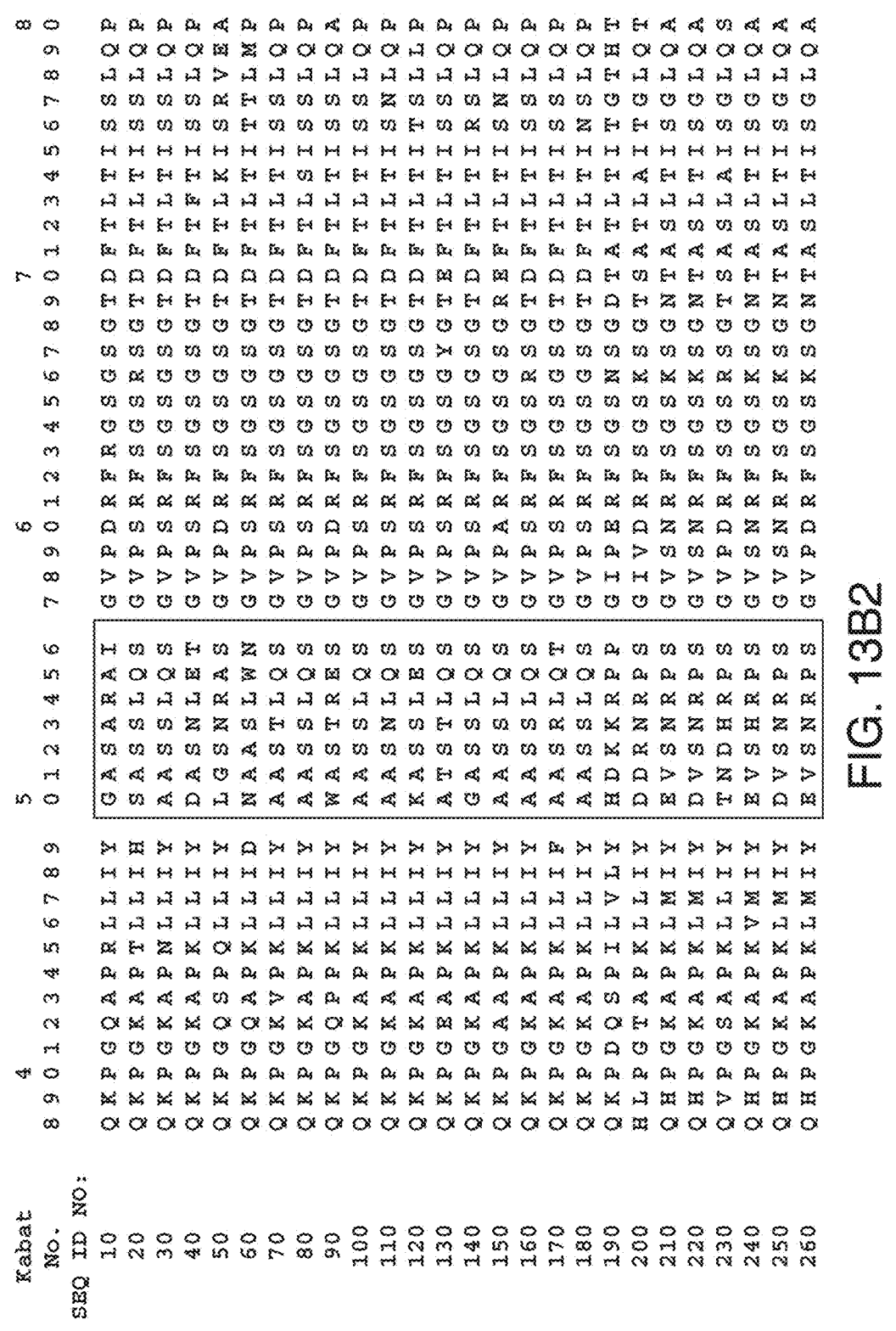
Figure 13B3:
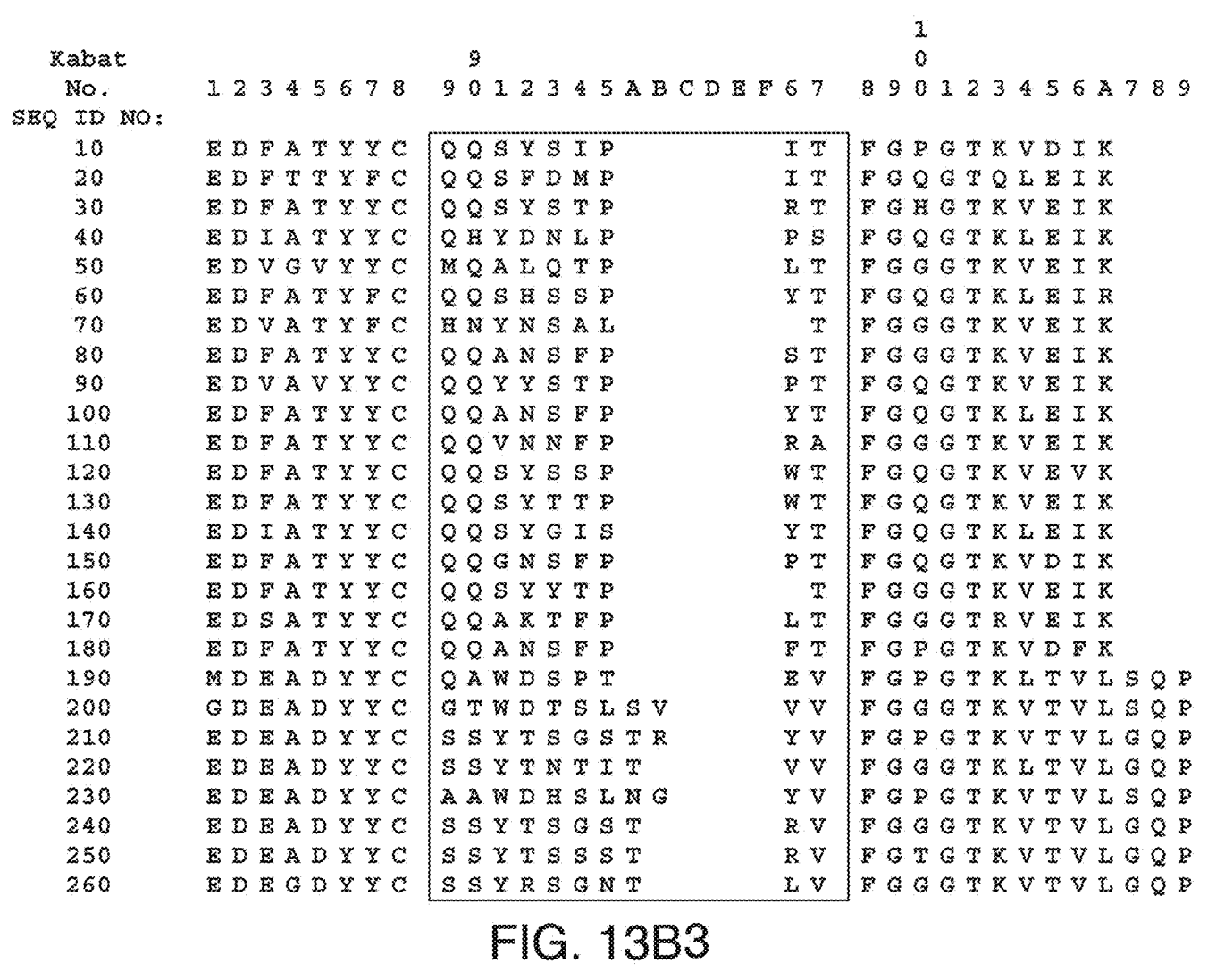

FIG. 13 provides amino acid sequences of $V_H$ (FIG. 13A1-3) and $V_L$ (FIG. 13B1-3) chains of anti-PD-L1 antibodies. For $V_H$ sequences, boxed regions indicate CDRs. For CDR-1H, Chothia CDRs are in italics, and Kabat CDRs are underlined. For CDR-2H, Kabat CDRs are coextensive with the boxed sequences, with Chothia CDRs initalics. For $V_L$ sequences, boxed regions indicate Kabat/Chothia CDRs.

FIG. 14 shows the amino acid sequences of SD15 (SEQ ID NO:261), which includes the IL15R alpha sushi domain and IL15, tccλD7HC-SD15 (SEQ ID NO:262) and the LALA mutant of tccλD7HC-SD15 (SEQ ID NO:263), which contains alanine substitutions for two adjacent leucines at positions (Leu$^{234}$ and Leu$^{235}$) in the heavy chain constant region important for FcγRI.

FIG. 18 shows blocking of human PD1 to human PDL1 (left panel) and blocking of mouse PD1 to mouse PDL1 (right panel) by two affinity matured anti-PDL1 antibodies, compared to their parent tcc λD7 antibody.

FIG. 23 shows hPD-L1 binding (left panel) and ligand blocking (right panel) activity for fusion proteins of the invention.

DETAILED DESCRIPTION

Figure 1:
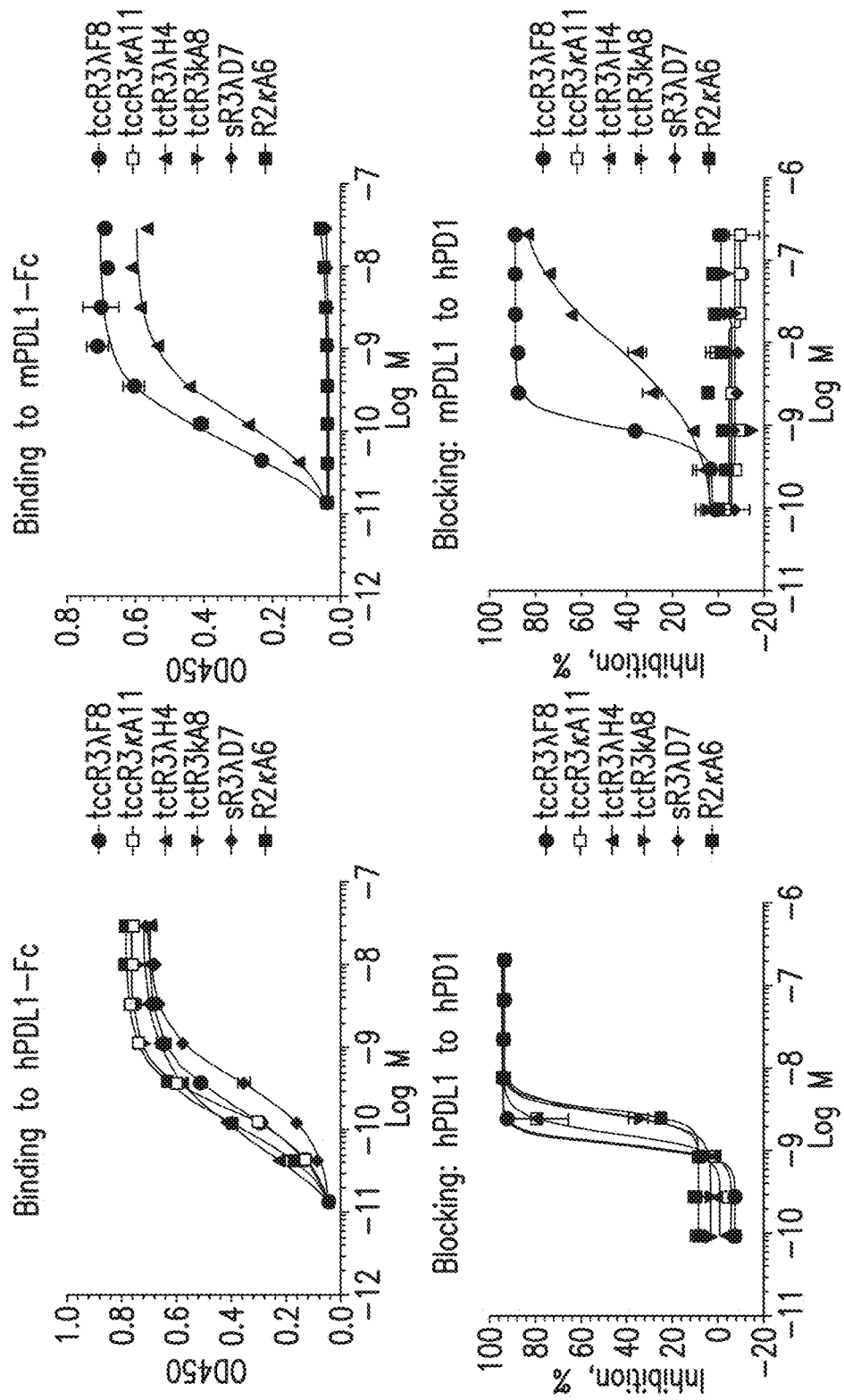
FIG. 1 depicts binding to human hPDL1-Fc (top left panel), blocking of hPDL1 to hPD1 (bottom left panel), binding to mouse mPDL1-Fc (top right panel), and blocking of mPDL1 to hPD1 (bottom right panel) of antibodies tccR3λF8, tccR3κA11, tccR3λH4, tctR3κA8, sR3λD7, and R2κA6.

The interaction of PD-1 on immune cells with PD-L1 inhibits proliferation and cytokine production by immune cells. PD-L1 is also inducible and upregulated in various tissues, including cancer. Together, PD-1 and PD-L1 play a role in immunosuppression. The invention provides novel antibodies or antigen binding fragments of such antibodies that bind to PD-L1 and block the interaction with PD-1. In embodiments of the invention, the antibodies reduce or inhibit immunosuppression.

Novel antibodies of the invention are set forth in Table 1 and the accompanying sequence listing, which set forth amino acid sequences of heavy and light chain CDRs (identified according to the identification systems of Kabat and Chothia), as well as complete heavy and light chain variable region. The first two heavy chain CDRs are identified according to the common systems of Kabat and Chothia, which provide distinct, but overlapping locations for the CDRs. A comparison of the numerous heavy and light chains shows a significant similarity among many of the CDR sequences. Accordingly, it would be expected that many of the CDRs can be mixed and matched among the sequences.

The antibodies can have one or more amino acid substitutions, deletions, insertions, and/or additions. In certain embodiments, the antibodies comprise one of the above-mentioned heavy chain variable domains and one of the above-mentioned light chain variable domains. In certain embodiments, the PD-L1 antibodies or binding fragments thereof comprise one or more CDRs or one or more variable domains with an amino acid sequence at least 85% at least 90%, at least 95%, at least 97%, at least 98%, or at least 99%, identical to the CDR and variable domain sequences set forth in Table 1.

"Identity" refers to the number or percentage of identical positions shared by two amino acid or nucleic acid sequences, taking into account the number of gaps, and the length of each gap, which need to be introduced for optimal alignment of the two sequences. "Substantially identical" means an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein. Amino acid substitutions can be made, in some cases, by selecting substitutions that do not differ significantly in their effect on maintaining (a) the structure of the peptide backbone in the area of the substitution, (b) the charge or hydrophobicity of the molecule at the target sit; or (c) the bulk of the side chain. For example, naturally occurring residues can be divided into groups based on side-chain properties; (1) hydrophobic amino acids (norleucine, methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Examples of substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenyalanine, glycine for proline, threonine for serine, serine for threonine, tyrosine for tryptophan, phenylalanine for tyrosine, and/or leucine for valine.

Preferably, the amino acid sequence is at least 80%, or at least 85%, or at least 90%, or at least 95% identical to an amino acid sequence disclosed herein. Methods and computer programs for determining sequence similarity are publically available, including, but not limited to, the GCG program package (Devereux et al., Nucleic Acids Research 12: 387, 1984), BLASTP, BLASTN, FASTA (Altschul et al., J. Mol. Biol. 215:403 (1990), and the ALIGN program (version 2.0). The well-known Smith Waterman algorithm may also be used to determine similarity. The BLAST program is publicly available from NCBI and other sources (BLAST Manual, Altschul, et al., NCBI NLM NIH, Bethesda, Md. 20894; BLAST 2.0 at http://www.ncbi.nlm.nih.gov/blast/). In comparing sequences, these methods account for various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

Antibodies of the invention also include those for which binding characteristics have been improved by direct mutation, methods of affinity maturation, phage display, or chain shuffling. Affinity and specificity may be modified or improved by mutating CDRs and screening for antigen binding sites having the desired characteristics. CDRs are mutated in a variety of ways. One way is to randomize individual residues or combinations of residues so that in a population of otherwise identical antigen binding sites, all twenty amino acids are found at particular positions. Alternatively, mutations are induced over a range of CDR residues by error prone PCR methods (see, e.g., Hawkins et al., J. Mol. Biol., 226: 889-896 (1992)). For example, phage display vectors containing heavy and light chain variable region genes may be propagated in mutator strains of E. coli (see, e.g., Low et al., J. Mol. Biol., 250: 359-368 (1996)). These methods of mutagenesis are illustrative of the many methods known to one of skill in the art.

To minimize the immunogenicity, antibodies which comprise human constant domain sequences are preferred. The antibodies may be or may combine members of any immunoglobulin class, such as IgG, IgM, IgA, IgD, or IgE, and the subclasses thereof. The antibody class may be selected to optimize effector functions (e.g., complement dependent cytotoxicity (CDC) and antibody dependent cellular cytotoxicity (ADCC)) of natural antibodies.

Certain embodiments of the invention involve the use of PD-L1-binding antibody fragments. An Fv is the smallest fragment that contains a complete heavy and light chain variable domain, including all six hypervariable loops (CDRs). Lacking constant domains, the variable domains are noncovalently associated. The heavy and light chains may be connected into a single polypeptide chain (a "single-chain Fv" or "scFv") using a linker that allows the $V_H$ and $V_L$ domains to associate to form an antigen binding site. In an embodiment of the invention, the linker is (Gly-Gly-Gly-Gly-Ser)$_3$. Since scFv fragments lack the constant domains of whole antibodies, they are considerably smaller than whole antibodies. scFv fragments are also free of normal heavy-chain constant domain interactions with other biological molecules which may be undesired in certain embodiments.

Fragments of an antibody containing $V_H$, $V_L$, and optionally $C_L$, $C_H1$, or other constant domains can also be used. Monovalent fragments of antibodies generated by papain digestion are referred to as Fab and lack the heavy chain hinge region. Fragments generated by pepsin digestion, referred to as F(ab')$_2$, retain the heavy chain hinge and are divalent. Such fragments may also be recombinantly produced. Many other useful antigen-binding antibody fragments are known in the art, and include, without limitation, diabodies, triabodies, single domain antibodies, and other monovalent and multivalent forms.

The invention further provides multivalent antigen-binding proteins, which can be in the form, without limitation, of antibodies, antigen-binding fragments thereof, and proteins comprising all or part of antigen-binding portions of antibodies. Multivalent antigen-binding proteins may be monospecific, bispecific, or multispecific. The term specificity refers to the number of different types of antigenic determinants to which a particular molecule can bind. If an immunoglobulin molecule binds to only one type of antigenic determinant, the immunoglobulin molecule is monospecific. If the immunoglobulin molecule binds to different types of antigenic determinants then the immunoglobulin molecule is multispecific.

In an embodiment of the invention, the PD-L1 binding protein has an on rate constant (Kon) of at least about $10^2 M^{-1} s^{-1}$; at least about $10^3 M^{-1} s^{-1}$; at least about $10^4 M^{-1} s^{-1}$; at least about $10^5 M^{-1} s^{-1}$; or at least about $10^6 M^{-1} s^{-1}$, as measured by surface plasmon resonance. In an embodiment, the PD-L1 binding protein has an on rate constant (Kon) between $10^2 M^{-1} s^{-1}$ and $10^3 M^{-1} s^{-1}$; between $10^3 M^{-1} s^{-1}$ and $10^4 M^{-1} s^{-1}$; between $10^4 M^{-1} s^{-1}$ and $10^5 M^{-1} s^{-1}$; or between $10^5 M^{-1} s^{-1}$ and $10^6 M^{-1} s^{-1}$, as measured by surface plasmon resonance.

In another embodiment the PD-L1 binding protein has an off rate constant (Koff) of at most about $10^{-3} s^{-1}$; at most about $10^{-4} s^{-1}$; at most about $10^{-5} s^{-1}$; or at most about $10^{-6} s^{-1}$, as measured by surface plasmon resonance. In an embodiment, the PD-L1 binding protein has an off rate constant (Koff) of $10^{-3} s^{-1}$ to $10^{-4} s^{-1}$; of $10^{-4} s^{-1}$ to $10^{-5} s^{-1}$; or of $10^{-5} s^{-1}$ to $10^{-6} s^{-1}$, as measured by surface plasmon resonance.

In another embodiment the PD-L1 binding protein has a dissociation constant ($K_D$) of at most about $10^{-7} M$; at most about $10^{-8} M$; at most about $10^{-9} M$; at most about $10^{-10} M$; at most about $10^{-11} M$; at most about $10^{-12} M$; or at most $10^{-13} M$. In an embodiment, the binding protein has a dissociation constant ($K_D$) to its targets of $10^{-7} M$ to $10^{-8} M$; of $10^{-8} M$ to $10^{-9} M$; of $10^{-9} M$ to $10^{-10} M$; of $10^{-10} M$ to $10^{-11} M$; of $10^{-11} M$ to $10^{-12} M$; or of $10^{-12} M$ to $10^{-13} M$.

The binding protein described herein may be a conjugate further comprising an imaging agent, a therapeutic agent, or a cytotoxic agent. In an embodiment, the imaging agent is a radiolabel, an enzyme, a fluorescent label, a luminescent label, a bioluminescent label, a magnetic label, or biotin. In another embodiment, the radiolabel is: $^3H$, $^{14}C$, $^{35}S$, $^{90}Y$, $^{99}Tc$, $^{111}In$, $^{125}I$, $^{131}I$, $^{177}Lu$, ro $^{153}Sm$. In yet another embodiment, the therapeutic or cytotoxic agent is an antimetabolite, an alkylating agent, an antibiotic, a growth factor, a cytokine, an anti-angiogenic agent, an anti-mitotic agent, an anthracycline, toxin, or an apoptotic agent. As discussed below, immunostimulatory cytokines are of particular importance.

The invention also provides molecules that bind PD-L1 to inhibit immunosuppression, which also promote immune responses by interaction with other ligands or receptors. As exemplified herein, such a molecule combines the PD-L1-binding domain of an antibody with a domain that stimulates NK or T cell function. Such a stimulatory domain can be, without limitation, one that binds to and stimulates a receptor that is responsive to an interleukin or an interferon, such as, without limitation, IL2, IL7, IL15, and IL21. The stimulatory domain exemplified herein is a hybrid domain comprising the sushi domain of the IL15R alpha chain attached to IL15 by a linker (e.g., SEQ ID NO:261). An example of a complete molecule is set forth by SEQ ID NO:262. A nearly identical molecule, modified with two amino acid substitutions in the region between the antibody domain and the IL15R-stimulating domain, to inhibit proteolysis in the region, is set forth by SEQ ID NO:263. As demonstrated herein, a molecule which comprises a PD-L1 binding domain that inhibits immunosuppression, and a second domain which promotes an immune response, provides for increased immune cell activity, compared to two distinct molecules that providing the functions separately.

As exemplified herein, the PD-L1-binding portion of the molecule is an antigen-binding domain of an antibody. Several novel antibody heavy and light chain variable domains and antibodies that include them are provided. According to the invention, the PD-L1-binding portion can be any agent that binds to PD-L1 and blocks immunosuppression. These include anti-PD-L1 antibodies and fragments, not limited to those novel antibodies disclosed herein, as well as peptides and proteins derived from PD1, the natural ligand of PD-L1.

As disclosed herein, the PD-L1-binding domain is linked to a domain that stimulates NK and T cell activity. The domain comprises IL15, and joined to it by a flexible linker, the "sushi" domain from the alpha chain of the IL15 receptor. The sushi domain binds to IL15 with high affinity and the complex of IL15 with the sushi domain is particularly active for stimulating NK and T cell proliferation. What is especially notable is that, as shown in the Examples, treatment with an agent combining the PD-L1-binding domain in the same molecule as the IL15 stimulatory domain is more effective than combined treatment using the PD-L1-binding domain and IL15 stimulatory domain as separate molecules.

Thus, in certain embodiments, the invention contemplates hybrid molecules comprising a domain that bind to PD-L1 and blocks binding to PD1, and a domain that stimulates IL15R, thus proliferation of immune cells. As exemplified, the IL15R stimulatory domain comprises the sushi domain of the IL15R alpha chain joined to IL15 by a flexible linker similar to those employed for, e.g., single chain Fv molecules (i.e., containing 15-20 amino acids which are predominantly serine and glycine. In practice, there are other methods that can be used, which may be preferred for example for manufacturing procedures. Further, one recognizes the domain structures, thus the modular aspects and other features of the disclosed hybrid proteins. For example, the linker joining the sushi domain to IL15 is useful for expressing the hybrid as one polypeptide, but could just as well be replaced by other agents, linkers, or cross linkers. Alternatively, the high affinity of IL15 for the sushi-containing portion of the IL15R alpha chain indicates that the sushi domain and IL15 would form a stable complex that need not be covalent. Similarly, while the exemplified protein comprises an entire antibody constant region, other antigen binding fragments of a PD-L1-binding antibody would suffice.

Accordingly, the invention provides a PD-L1-binding domain linked to an IL15R stimulatory domain, which IL15R stimulatory domain comprises the sushi domain of the IL15R alpha chain or a variant thereof and IL15 or a variant thereof. In certain embodiments, the variants would be 80%, 85%, 87%, 90%, 91%, 92%, 93%, 94%, or 95% identical to the sequences disclosed herein. In one embodiment, the sushi domain of the IL15R alpha chain, and IL15 form a covalent complex. In another embodiment, the sushi domain of the IL15R alpha chain and IL15 form a non-covalent complex. The PD-L1 binding domain can comprise one, two, three, four, five, or six CDRs, or the heavy and or light chain variable domain of an antibody thereof disclosed herein, of be an antigen-binding fragment thereof, or a variant thereof, such as a variant that is 80%, 85%, 87%, 90%, 91%, 92%, 93%, 94%, or 95% identical, or a PD-L1 antibody known in the art that blocks binding to PD-1 or an antigen binding fragment thereof.

It is understood that the anti-PD-L1 antibodies and hybrid proteins of the invention, where used in a mammal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, sucrose, polysorbate, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the antibodies.

In the methods of the present invention, a therapeutically effective amount of an antibody of hybrid protein of the invention is administered to a mammal in need thereof. The term "administering" as used herein means delivering the antibodies and fusion proteins of the present invention to a mammal by any method that may achieve the result sought. They may be administered, for example, intravenously or intramuscularly. Although the exemplified antibodies of the invention are particularly useful for administration to humans, they may be administered to other mammals as well. The term "mammal" as used herein is intended to include, but is not limited to, humans, laboratory animals, domestic pets and farm animals. "Therapeutically effective amount" means an amount of antibody of the present invention that, when administered to a mammal, is effective in producing the desired therapeutic effect, such as inhibiting kinase activity.

Antibodies and hybrid proteins of the invention are useful for inhibiting tumors and other neoplastic diseases, as well as treating other pathologic conditions associated with immunosuppression. Tumors that can be treated include primary tumors, metastatic tumors, and refractory tumors. Refractory tumors include tumors that fail to respond or are resistant to treatment with chemotherapeutic agents alone, antibodies alone, radiation alone or combinations thereof. Refractory tumors also encompass tumors that appear to be inhibited by treatment with such agents, but recur up to five years, sometimes up to ten years or longer after treatment is discontinued. The antibodies are effective for treating vascularized tumors and tumor that are not vascularized, or not yet substantially vascularized.

Examples of solid tumors which may be accordingly treated include breast carcinoma, lung carcinoma, colorectal carcinoma, pancreatic carcinoma, glioma and lymphoma. Some examples of such tumors include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, and liver tumors. Other examples include Kaposi's sarcoma, CNS neoplasms, neuroblastomas, capillary hemangioblastomas, meningiomas and cerebral metastases, melanoma, gastrointestinal and renal carcinomas and sarcomas, rhabdomyosarcoma, glioblastoma, preferably glioblastoma multiforme, and leiomyosarcoma. Examples of vascularized skin cancers for which the antagonists of this invention are effective include squamous cell carcinoma, basal cell carcinoma and skin cancers that can be treated by suppressing the growth of malignant keratinocytes, such as human malignant keratinocytes.

Examples of non-solid tumors include leukemia, multiple myeloma and lymphoma that are unresponsive to cytokines, such as IL15. Some examples of leukemias include acute myelogenous leukemia (AML), chronic myelogenous leukemia (CML), acute lymphocytic leukemia (ALL), chronic lymphocytic leukemia (CLL), erythrocytic leukemia or monocytic leukemia. Some examples of lymphomas include Hodgkin's and non-Hodgkin's lymphoma.

The PD-L1 antibodies and immune cell stimulating hybrid proteins of the invention are also used in the treatment of viral infections. PD-1 expression on T cells correlates with viral load in HIV and HCV infected patients and PD-1 expression has been identified as a marker for exhausted virus-specific CD8+ T cells. For example, PD-1$^+$ CD8$^+$ T cells show impaired effector functions and PD-1 associated T cell exhaustion which can be restored by blocking the PD-1/PD-L1 interaction. This results in recovery of virus-specific CD8+ T cell mediated immunity, indicating that interrupting PD-1 signaling using an antagonistic antibody restores T-cell effector functions. Immunotherapy based on the blockade of PD-1/PD-L1 results in breakdown of T-cell tolerance not only to tumor antigens, but also provides a strategy to reactivate virus-specific effector T cells and eradicate pathogens in chronic viral infections. Accordingly, the antibodies and hybrid proteins of the invention are useful to treat chronic viral infections, including, without limitation, HCV and HIV, and lymphocytic choriomeningitis virus (LCMV).

The antibodies and hybrid proteins of the invention can be advantageously administered with second agents to patients in need thereof. For example, in some embodiments, an antibody or hybrid protein of the invention is administered to a subject with an anti-neoplastic agent. In some embodiments, an antibody or hybrid protein of the invention is administered to a subject with a second angiogenesis inhibitor. In some embodiments, an antibody or hybrid protein of the invention is administered with an anti-inflammatory agent or an immunosuppressant.

Antineoplastic agents include cytotoxic chemotherapeutic agents, targeted small molecules and biological molecules, and radiation. Non-limiting examples of chemotherapeutic agents include cisplatin, dacarbazine (DTIC), dactinomycin, irinotecan, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, interferon alpha, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, taxol and combinations thereof.

Targeted small molecules and biological molecules include, without limitation, inhibitors of components of signal transduction pathways, such as modulators of tyrosine kinases and inhibitors of receptor tyrosine kinases, and agents that bind to tumor-specific antigens. Non-limiting examples of growth factor receptors involved in tumorigenesis are the receptors for platelet-derived growth factor (PDGFR), insulin-like growth factor (IGFR), nerve growth factor (NGFR), and fibroblast growth factor (FGFR), and receptors of the epidermal growth factor receptor family, including EGFR (erbB1), HER2 (erbB2), erbB3, and erbB4.

EGFR antagonists include antibodies that bind to EGFR or to an EGFR ligand, and inhibits ligand binding and/or receptor activation. For example, the agent can block formation of receptor dimers or heterodimer with other EGFR family members. Ligands for EGFR include, for example, EGF, TGF-α amphiregulin, heparin-binding EGF (HB-EGF) and betaregullulin. An EGFR antagonist can bind externally to the extracellular portion of EGFR, which may or may not inhibit binding of the ligand, or internally to the tyrosine kinase domain. EGFR antagonists further include agents that inhibit EGFR-dependent signal transduction, for example, by inhibiting the function of a component of the EGFR signal transduction pathway. Examples of EGFR antagonists that bind EGFR include, without limitation, biological molecules, such as antibodies (and functional equivalents thereof) specific for EGFR, and small molecules, such as synthetic kinase inhibitors that act directly on the cytoplasmic domain of EGFR.

Small molecule and biological inhibitors include inhibitors of epidermal growth factor receptor (EGFR), including gefitinib, erlotinib, and cetuximab, inhibitors of HER2 (e.g., trastuzumab, trastuzumab emtansine (trastuzumab-DM1; T-DM1) and pertuzumab), anti-VEGF antibodies and fragments (e.g., bevacizumab), antibodies that inhibit CD20 (e.g., rituximab, ibritumomab), anti-VEGFR antibodies (e.g., ramucirumab (IMC-1121B), IMC-1C11, and CDP791), anti-PDGFR antibodies, and imatinib. Small molecule kinase inhibitors can be specific for a particular tyrosine kinase or be inhibitors of two or more kinases. For example, the compound N-(3,4-dichloro-2-fluorophenyl)-7-({[(3aR,6aS)-2-methyloctahydrocyclopenta[c] pyrrol-5-yl] methyl}oxy)-6-(methyloxy)quinazolin-4-amine (also known as XL647, EXEL-7647 and KD-019) is an in vitro inhibitor of several receptor tyrosine kinases (RTKs), including EGFR, EphB4, KDR (VEGFR), Flt4 (VEGFR3) and ErbB2, and is also an inhibitor of the SRC kinase, which is involved in pathways that result in nonresponsiveness of tumors to certain TKIs. In an embodiment of the invention, treatment of a subject in need comprises administration of a rho-kinase inhibitor of Formula I and administration of KD-019.

Dasatinib (BMS-354825; Bristol-Myers Squibb, New York) is another orally bioavailable, ATP-site competitive Src inhibitor. Dasatanib also targets Bcr-Abl (FDA-approved for use in patients with chronic myelogenous leukemia (CML) or Philadelphia chromosome positive (Ph+) acute lymphoblastic leukemia (ALL)) as well as c-Kit, PDGFR, c-FMS, EphA2, and SFKs. Two other oral tyrosine kinase inhibitor of Src and Bcr-Abl are bosutinib (SKI-606) and saracatinib (AZD0530).

In an embodiment of the invention, a PD-L1 antibody or conjugate of the invention is used in combination with an anti-viral agent to treat a chronic virus infection. For example, for HCV, the following agents can be used. HCV protease inhibitors include, without limitation, boceprevir, telaprevir (VX-950), ITMN-191, SCH-900518, TMC-435, BI-201335, MK-7009, VX-500, VX-813, BMS790052, BMS650032, and VBY376. HCV nonstructural protein 4B (NS4B) inhibitors include, but are not limited to, clemizole, and other NS4B-RNA binding inhibitors, including but not limited to benzimidazole RBIs (B-RBIs) and indazole RBIs (I-RBIs). HCV nonstructural protein 5A (NS5A) inhibitors include, but are not limited to, BMS-790052, A-689, A-831, EDP239, GS5885, and PP1461. HCV polymerase (NS5B) inhibitors include, but are not limited to nucleoside analogs (e.g., valopicitabine, R1479, R1626, R7128), nucleotide analogs (e.g., IDX184, PSI-7851, PSI-7977, and non-nucleoside analogs (e.g., filibuvir, HCV-796, VCH-759, VCH-916, ANA598, VCH-222 (VX-222), BI-207127, MK-3281, ABT-072, ABT-333, GS9190, BMS791325). Also, ribavirin or a ribavirin analog such as Taribavirin (viramidine; ICN 3142), Mizoribine, Merimepodib (VX-497), Mycophenolate mofetil, and Mycophenolate can be used.

In certain embodiments, a dose of an antibody or hybrid protein of the invention is administered to a subject every day, every other day, every couple of days, every third day, once a week, twice a week, three times a week, or once every two weeks. In other embodiments, two, three or four doses of a compound or a composition is administered to a subject every day, every couple of days, every third day, once a week or once every two weeks. In some embodiments, a dose(s) of a compound or a composition is administered for 2 days, 3 days, 5 days, 7 days, 14 days, or 21 days. In certain embodiments, a dose of a compound or a composition is administered for 1 month, 1.5 months, 2 months, 2.5 months, 3 months, 4 months, 5 months, 6 months or more.

Methods of administration include but are not limited to parenteral, intradermal, intravitrial, intramuscular, intraperitoneal, intravenous, subcutaneous, intranasal, epidural, oral, sublingual, intranasal, intracerebral, intravaginal, transdermal, transmucosal, rectally, by inhalation, or topically, particularly to the ears, nose, eyes, or skin. The mode of administration is left to the discretion of the practitioner. In most instances, administration will result in the release of a compound into the bloodstream. For treatment of ocular disease, intravitrial administration of biological agents is preferred.

In specific embodiments, it may be desirable to administer a compound locally. This may be achieved, for example, and not by way of limitation, by local infusion, topical application, by injection, by means of a catheter, or by means of an implant, said implant being of a porous, non-porous, or gelatinous material, including membranes, such as sialastic membranes, or fibers. In such instances, administration may selectively target a local tissue without substantial release of a compound into the bloodstream.

Pulmonary administration can also be employed, e.g., by use of an inhaler or nebulizer, and formulation with an aerosolizing agent, or via perfusion in a fluorocarbon or synthetic pulmonary surfactant. In certain embodiments, a compound is formulated as a suppository, with traditional binders and vehicles such as triglycerides.

In another embodiment, a compound is delivered in a vesicle, in particular a liposome (See Langer, 1990, Science 249:1527-1533; Treat et al., in Liposomes in the Therapy of Infectious Disease and Bacterial infection, Lopez-Berestein and Fidler (eds.), Liss, New York, pp. 353-365 (1989); Lopez Berestein, ibid., pp. 317-327; see generally ibid.).

In another embodiment, a compound is delivered in a controlled release system (See, e.g., Goodson, in Medical Applications of Controlled Release, supra, vol. 2, pp. 115-138 (1984)). Examples of controlled-release systems are discussed in the review by Langer, 1990, Science 249:1527-1533 may be used. In one embodiment, a pump may be used (See Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (See Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; See also Levy et al., 1985, Science 228:190; During et al., 1989, Ann. Neurol. 25:351; Howard et al., 1989, J. Neurosurg. 71:105).

The above-described administration schedules are provided for illustrative purposes only and should not be considered limiting. A person of ordinary skill in the art will readily understand that all doses are within the scope of the invention.

It is to be understood and expected that variations in the principles of invention herein disclosed may be made by one skilled in the art and it is intended that such modifications are to be included within the scope of the present invention.

Throughout this application, various publications are referenced. These publications are hereby incorporated into this application by reference in their entireties to more fully describe the state of the art to which this invention pertains. The following examples further illustrate the invention, but should not be construed to limit the scope of the invention in any way.

EXAMPLES

Mixed-Lymphocyte Reactions:

CD14 positive monocytes were isolated by negative selection from whole blood using RosetteSep human monocyte enrichment kit (StemCell technologies). Immature monocyte-derived dendritic cells (mo-DC) were generated by culturing CD14 positive cells in IMDM supplemented with 10% FBS with 150 ng/mL GM-CSF and 50 ng/mL IL-4 for 6 to 7 days. CD4 positive cells were negatively isolated from whole blood using RosetteSep human CD4 enrichment kit (StemCell technologies). Mo-DC and CD4 positive cells from a different donor were then co-cultured at a ratio 1 to 10 of mo-DC to CD4 cells respectively. To assess blocking function of anti-PDL1 antibodies, increasing amount of anti-PDL1 antibodies was added in the beginning of co-culture. In some cases, increasing amount of IL15 was also added at the beginning of co-culture. At day 6 or 7, the supernatants were collected for measurements of secreted IL-2 and IFNγ by ELISA. The number of CD4 cells and expression of the proliferation marker, Ki67, were evaluated by flow cytometry.

Activation of PBMC:

PBMC was isolated from whole blood using Histopaque-1077 (Sigma), cultured in IMDM supplemented with 10% FBS and activated by either SEB (0.1 ug/mL), PHA (1 ug/mL) or anti-CD3 clone HiT3a (1 ug/mL, eBioscience) for 3 to 7 days. Binding of either anti-PDL1 antibodies or anti-PDL1-SD15 fusion proteins were evaluated in activated PBMC after 3 days by flow cytometry. Functional assessment of anti-PDL1 antibodies were done by addition of increasing amount of anti-PDL1 antibodies during PBMC activation with SEB. At day 2 or 3 supernatants were collected for measurements of IL-2 and IFNγ. In the case of anti-PDL1-SD15 fusion proteins, PBMC were cultured in the presence of either anti-PDL1-SD15 or anti-PDL1 antibodies, with no other activations. At day 6, cells were collected, and the numbers of CD8 and granzymeB, CD8 and perforin, and CD4 cells were evaluated by flow cytometry.

Activation of CD4 and CD8 Cells:

CD4 and CD8 positive cells were negatively isolated from whole blood using RosetteSep enrichment kits (StemCell technologies). CD4 cells were activated by either anti-CD3 or anti-CD3 and PDL1Fc coated beads in IMDM, 10% FBS in the presence of anti-PDL1 antibodies. At day 5, supernatants were collected for IFNγ measurements by ELISA, and cells were evaluated for expression of the proliferation marker Ki67 using flow cytometry. CD8 cells were activated by anti-CD3 coated beads and either IL15 or anti-PDL1-SD15 fusion proteins. In some cases anti-CD3 and PDL1Fc was used in place of anti-CD3 coated beads. At day 6 or 7 the supernatants were collected for measurements of IFNγ and TNFα secretions by ELISA. The cells were collected for measurements of CD8 activation by granzymeB and perforin markers using flow cytometry.

Nomenclature of Antibody-Fusion Proteins:

In experiments with anti-PD-L1 IL15 fusion proteins, shorter names for the fusion proteins are identified in the legends. The fusion protein tcclD7HC-SD15 is identified in figure legends as cD7-SD15. The fusion protein tcclF8HC-SD15 is identified in figure legends as F8-SD15.

Specific High Affinity Antibodies to PD-L1 from Phage-Display Library

Anti-PD-L1 antibodies with high affinity were obtained using a phage display library. In one procedure, phage Fabs amplified from Dyax libraries were panned on either recombinant human PDL1-Fc (PDL1 ECD and human Fc fusion protein, Q9NZQ7) or murine PDL1-Fc (Q9EP73) which were immobilized on immune-tubes for three rounds. The ELISA positive clones from round (R2) and round 3 (R3) were sequenced.

In a second procedure, phage Fabs amplified from the Dyax libraries were panned on recombinant human PDL1-Fc (PDL1 ECD and human Fc fusion protein, Q9NZQ7) for the first round, and then panned on activated T cells for second round. For third round, either the activated T cells or recombinant human PDL1-Fc were used for the panning. Clones which can bind to both soluble PDL1-Fc and cell expressed PDL1-Fc were sequenced. $V_H$ and $V_L$ variable domain sequences of these antibodies are set forth in FIG. 13 and the rows 1-26 of Table 1.

Unique clones were converted to IgG for the further characterization. The variable domains were inserted to Dyax expression vector pBhl. Both wild type CH1-CH2-CH3 domains and mutated CH1-CH2-CH3 (L234A and L235A, also referred to herein as LALA mutants) were prepared in the IgG format.

TABLE 1

Antibody Amino Acid Sequences by SEQ ID NO.

| | $V_H$ CDRs | | | | | | $V_L$ CDRs | | | |
|---|---|---|---|---|---|---|---|---|---|---|
| | H1 | H1 | H2 | H2 | | | L1 | L1 | L3 | |
| Mab | (K) | (C) | (K) | (C) | H3 | $V_H$ | L1 | L1 | L3 | $V_L$ |
| R2κA3 | 1 | 2 | 3 | 4 | 5 | 6 | 7 | 8 | 9 | 10 |
| R2κA4 | 11 | 12 | 13 | 14 | 15 | 16 | 17 | 18 | 19 | 20 |
| R2κA6 | 21 | 22 | 23 | 24 | 25 | 26 | 27 | 28 | 29 | 30 |
| R2κF4 | 31 | 32 | 33 | 34 | 35 | 36 | 37 | 38 | 39 | 40 |
| R2κH5 | 41 | 42 | 43 | 44 | 45 | 46 | 47 | 48 | 49 | 50 |
| R2κH6 | 51 | 52 | 53 | 54 | 55 | 56 | 57 | 58 | 59 | 60 |
| R2κH3 | 61 | 62 | 63 | 64 | 65 | 66 | 67 | 68 | 69 | 70 |
| sR3κA8 | 71 | 72 | 73 | 74 | 75 | 76 | 77 | 78 | 79 | 80 |
| sR3κA9 | 81 | 82 | 83 | 84 | 85 | 86 | 87 | 88 | 89 | 90 |
| sR3κB2 | 91 | 92 | 93 | 94 | 95 | 96 | 97 | 98 | 99 | 100 |
| sR3κB5 | 101 | 102 | 103 | 104 | 105 | 106 | 107 | 108 | 109 | 110 |
| tccR3κA8 | 111 | 112 | 113 | 114 | 115 | 116 | 117 | 118 | 119 | 120 |
| tccR3κA11 | 121 | 122 | 123 | 124 | 125 | 126 | 127 | 128 | 129 | 130 |
| tccR3κB7 | 131 | 132 | 133 | 134 | 135 | 136 | 137 | 138 | 139 | 140 |
| tccR3κD9 | 141 | 142 | 143 | 144 | 145 | 146 | 147 | 148 | 149 | 150 |
| tccκF10 | 161 | 162 | 163 | 164 | 165 | 166 | 157 | 158 | 159 | 160 |
| tctR3κA4 | 161 | 162 | 163 | 164 | 165 | 166 | 167 | 168 | 169 | 170 |
| tctR3κF8 | 171 | 172 | 173 | 174 | 175 | 176 | 177 | 178 | 179 | 180 |
| R2λA7 | 181 | 182 | 183 | 184 | 185 | 186 | 187 | 188 | 189 | 190 |
| R2λB12 | 191 | 192 | 193 | 194 | 195 | 196 | 197 | 198 | 199 | 200 |
| R2λD12 | 201 | 202 | 203 | 204 | 205 | 206 | 207 | 208 | 209 | 210 |
| sR3λD7 | 211 | 212 | 213 | 214 | 215 | 216 | 217 | 218 | 219 | 220 |
| sR3λE1 | 221 | 222 | 223 | 224 | 225 | 226 | 227 | 228 | 229 | 230 |
| tccλF8 | 231 | 232 | 233 | 234 | 235 | 236 | 237 | 238 | 239 | 240 |
| tccλD7 | 241 | 242 | 243 | 244 | 245 | 246 | 247 | 248 | 249 | 250 |
| tctR3λH4 | 251 | 252 | 253 | 254 | 255 | 256 | 257 | 258 | 259 | 260 |
| #101 | 264 | — | 243 | 244 | 245 | 265 | 247 | 248 | 249 | 250 |
| #102 | 266 | — | 243 | 244 | 245 | 267 | 247 | 248 | 249 | 250 |
| #103 | 268 | — | 243 | 244 | 245 | 269 | 247 | 248 | 249 | 250 |
| #104 | 270 | — | 243 | 244 | 245 | 271 | 247 | 248 | 249 | 250 |
| #105 | 272 | — | 243 | 244 | 245 | 273 | 247 | 248 | 249 | 250 |

TABLE 1-continued

Antibody Amino Acid Sequences by SEQ ID NO.

| | $V_H$ CDRs | | | | | | $V_L$ CDRs | | | |
|---|---|---|---|---|---|---|---|---|---|---|
| | H1 | H1 | H2 | H2 | | | | | | |
| Mab | (K) | (C) | (K) | (C) | H3 | $V_H$ | L1 | L1 | L3 | $V_L$ |
| #106 | 274 | — | 243 | 244 | 245 | 275 | 247 | 248 | 249 | 250 |
| #107 | 276 | — | 243 | 244 | 245 | 277 | 247 | 248 | 249 | 250 |
| #108 | 278 | — | 243 | 244 | 245 | 279 | 247 | 248 | 249 | 250 |
| #109 | 280 | — | 243 | 244 | 245 | 281 | 247 | 248 | 249 | 250 |
| #110 | 282 | — | 243 | 244 | 245 | 283 | 247 | 248 | 249 | 250 |
| #111 | 284 | — | 243 | 244 | 245 | 285 | 247 | 248 | 249 | 250 |
| #112 | 286 | — | 243 | 244 | 245 | 287 | 247 | 248 | 249 | 250 |
| #113 | 288 | — | 243 | 244 | 245 | 289 | 247 | 248 | 249 | 250 |
| #114 | 290 | — | 243 | 244 | 245 | 291 | 247 | 248 | 249 | 250 |
| #115 | 292 | — | 243 | 244 | 245 | 293 | 247 | 248 | 249 | 250 |
| #116 | 294 | — | 243 | 244 | 245 | 295 | 247 | 248 | 249 | 250 |
| #117 | 296 | — | 243 | 244 | 245 | 297 | 247 | 248 | 249 | 250 |
| #118 | 298 | — | 243 | 244 | 245 | 299 | 247 | 248 | 249 | 250 |
| #119 | 300 | — | 243 | 244 | 245 | 301 | 247 | 248 | 249 | 250 |
| #120 | 302 | — | 243 | 244 | 245 | 303 | 247 | 248 | 249 | 250 |
| #121 | 304 | — | 243 | 244 | 245 | 305 | 247 | 248 | 249 | 250 |
| #122 | 306 | — | 243 | 244 | 245 | 307 | 247 | 248 | 249 | 250 |
| #123 | 308 | — | 243 | 244 | 245 | 309 | 247 | 248 | 249 | 250 |
| #124 | 310 | — | 243 | 244 | 245 | 311 | 247 | 248 | 249 | 250 |
| #125 | 312 | — | 243 | 244 | 245 | 313 | 247 | 248 | 249 | 250 |

Figure 4:
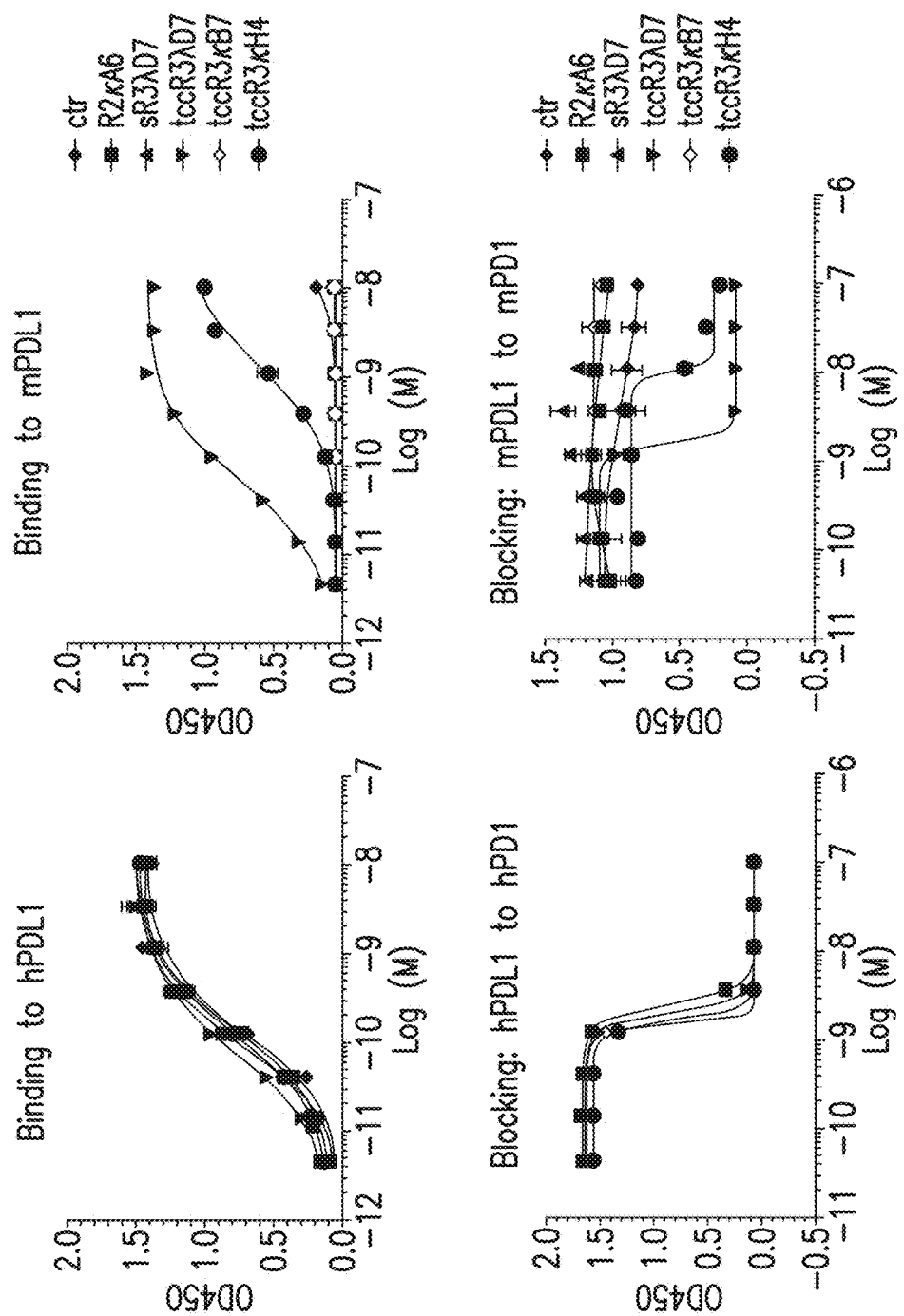
FIG. 4 depicts binding to human hPDL1-Fc (top left panel), blocking of hPDL1 to hPD1 (bottom left panel), binding to mouse mPDL1-Fc (top right panel), and blocking of mPDL1 to hPD1 (bottom right panel) of antibodies R2κA6, sR3λD7, tccR3λD7, tccR3κB7, and tccR3κH4.
Figure 5:
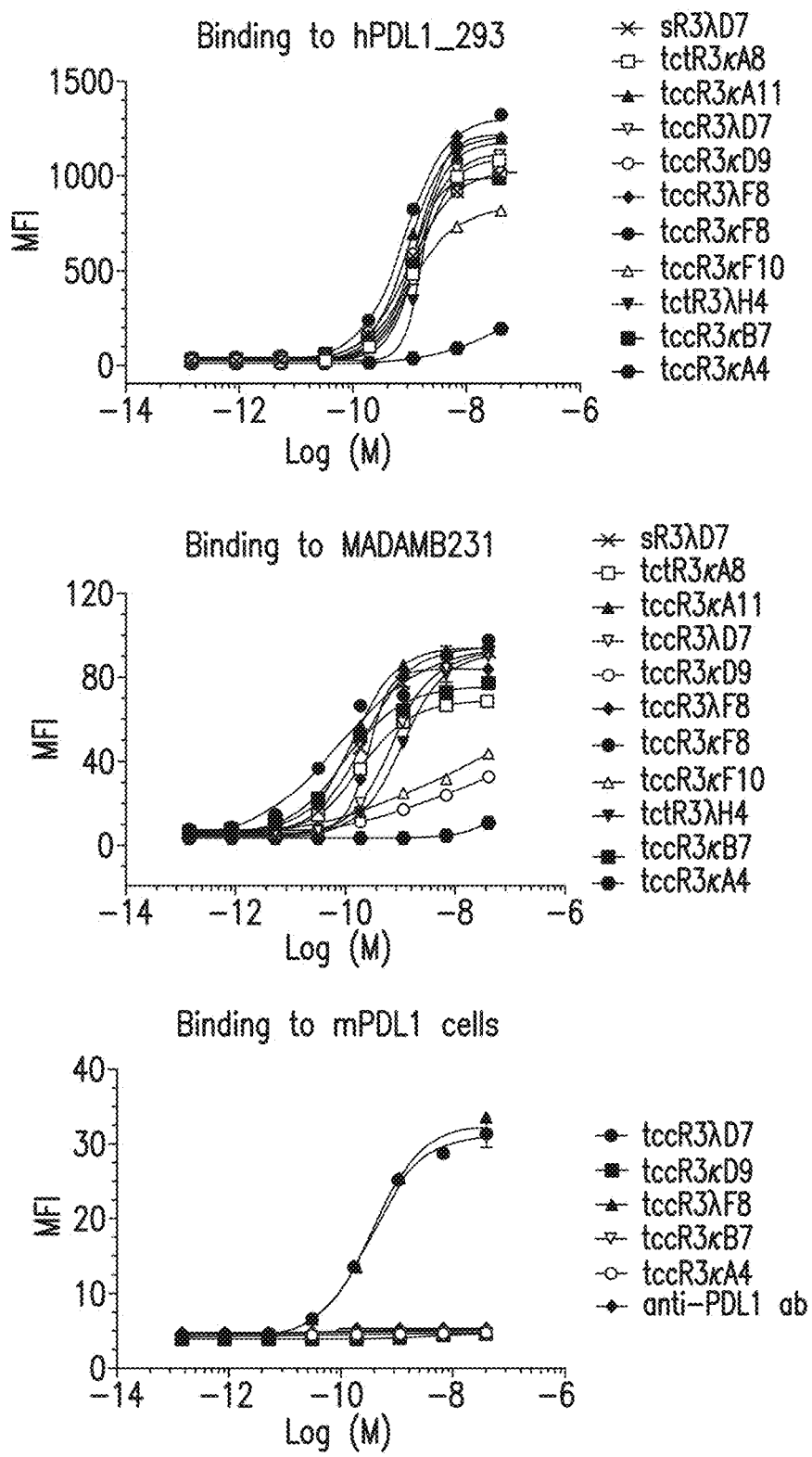
FIG. 5 depicts binding to PDLI-293 cells (top) and MDS-MB-231 (bottom) cells of antibodies sR3λD7, tctR3κA8, tccR3κA11, tccR3λD7, tccR3κD9, tccR3λF8, tccR3κF8, tccR3κF10, tccR3λH4, tccR3κB7, and tccR3κA4.

These antibodies were verified to have specific binding to PD-L1 by solid-phase ELISA (FIGS. 1-4) and HEK-293 cells (FIG. 5). Blocking of PD-1:PD-L1 interactions in the presence of these antibodies was determined by solid phase ELISA and by 293-HEK cells expressing PD-L1. Biacore was used to calculate the affinity constant for each antibody.

TABLE 2

$EC_{50}$ and $IC_{50}$ for antibodies of FIGS. 1-4

| FIG. 1 | tccR3λF8 | tccR3κA11 | tccR3λH4 | tctR3κA8 | sR3λD7 | R2κA6 |
|---|---|---|---|---|---|---|
| h_$EC_{50}$ | 0.167 | 0.172 | 0.056 | 0.106 | 0.388 | 0.117 |
| h_$IC_{50}$ | 1.19 | 1.58 | 1.17 | 2.94 | 2.89 | 3.17 |
| m_$EC_{50}$ | 0.0714 | ND | 0.144 | ND | ND | ND |
| m_$IC_{50}$ | 0.925 | ND | 9.14 | ND | ND | ND |

Figure 2:
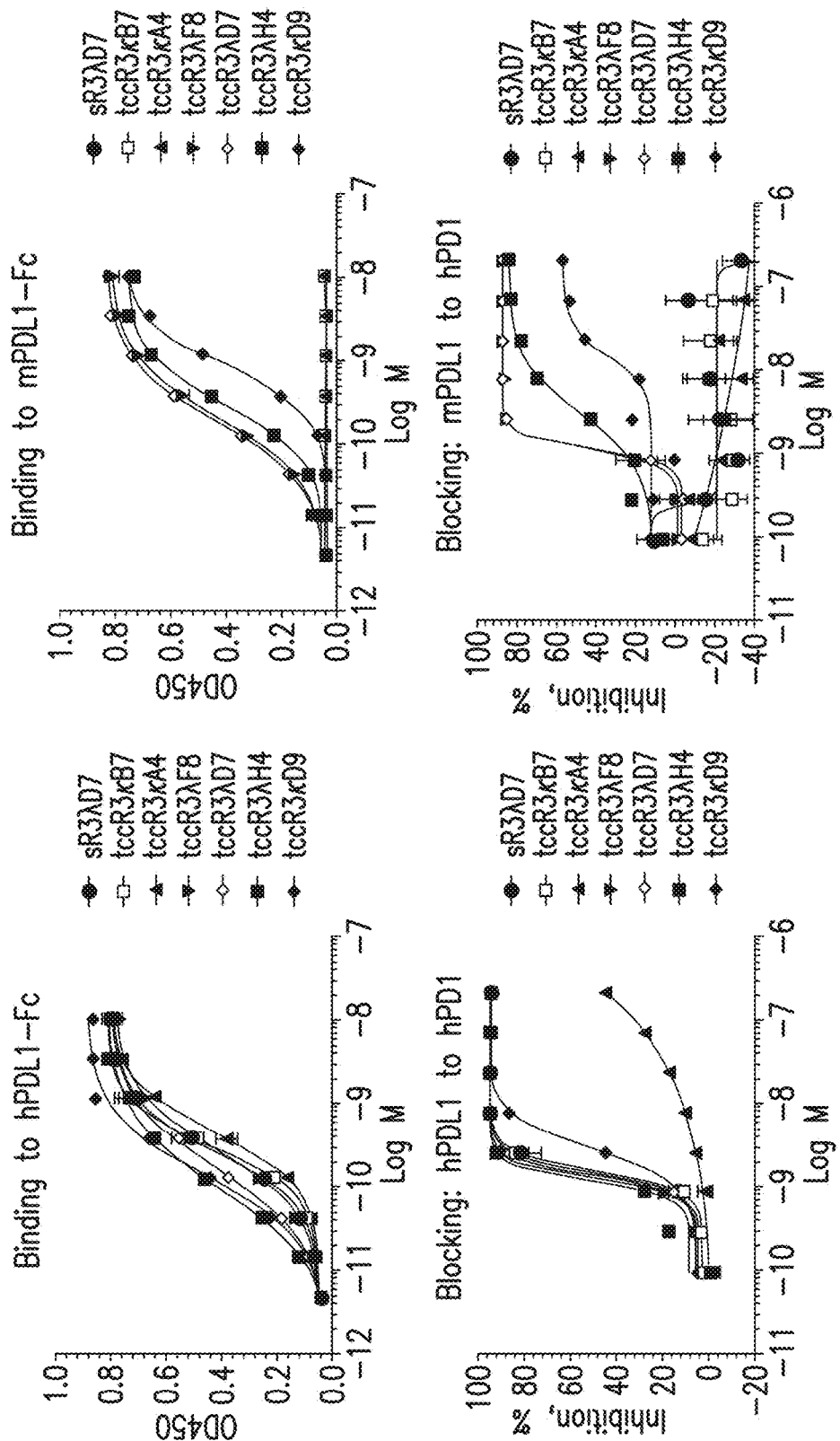
FIG. 2 depicts binding to human hPDL1-Fc (top left panel), blocking of hPDL1 to hPD1 (bottom left panel), binding to mouse mPDL1-Fc (top right panel), and blocking of mPDL1 to hPD1 (bottom right panel) of antibodies sR3λD7, tccR3κB7, tccR3κA4, tccR3λF8, tccR3λD7, tccR3λH4, and tccR3κD9.

| FIG. 2 | sR3λD7 | tccR3κB7 | tccR3κA4 | tccR3λF8 | tccR3λD7 | tccR3λH4 | tccR3κD9 |
|---|---|---|---|---|---|---|---|
| h_$EC_{50}$ | 0.255 | 0.3 | 0.443 | 0.265 | 0.155 | 0.0947 | 0.132 |
| h_$IC_{50}$ | 1.47 | 1.26 | ND | 1.36 | 1.24 | 1.12 | 2.75 |
| m_$EC_{50}$ | ND | ND | ND | 0.205 | 0.185 | 0.282 | ND |
| m_$IC_{50}$ | ND | ND | ND | 1.08 | 1.13 | 2.88 | ND |

Figure 3:
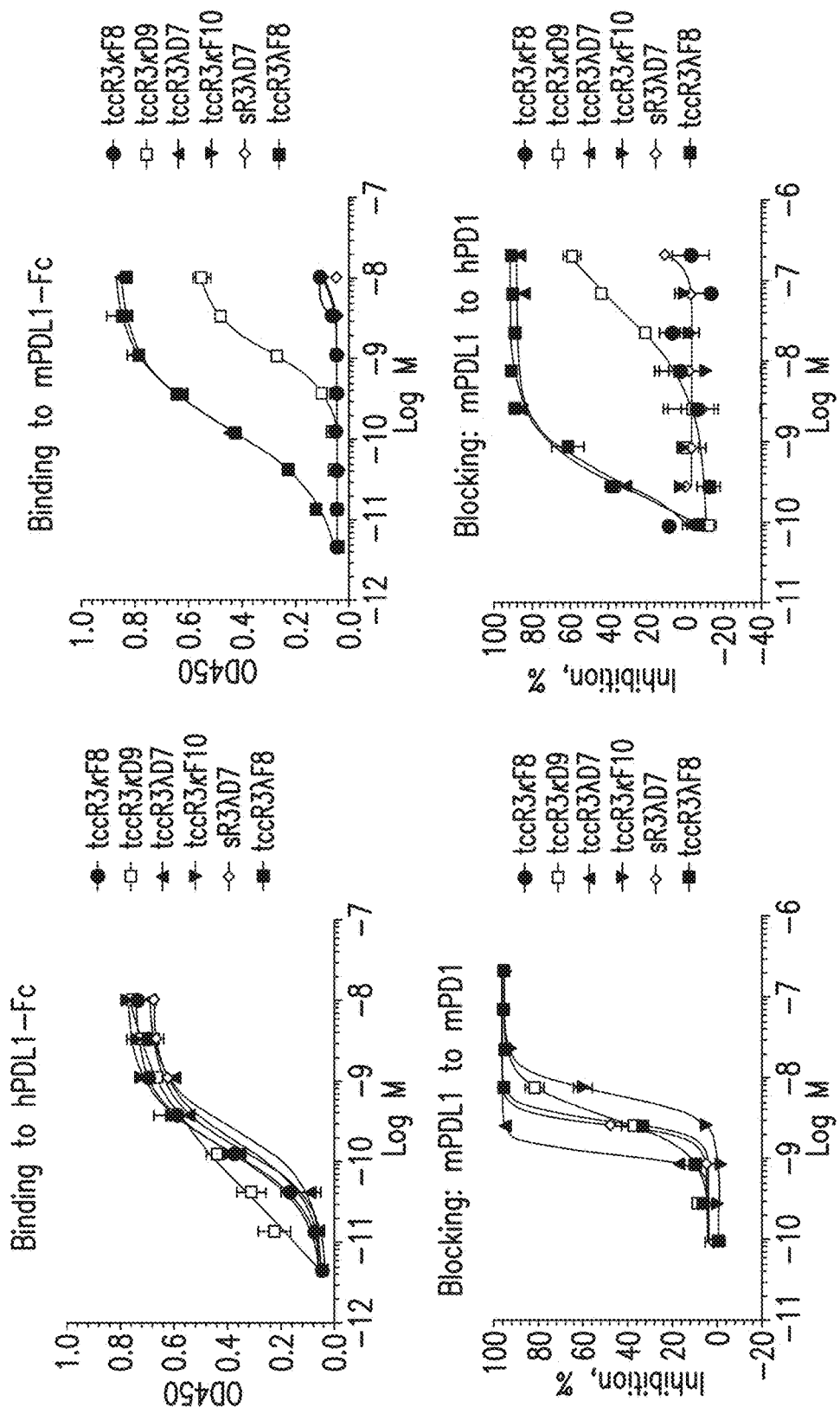
FIG. 3 depicts binding to human hPDL1-Fc (top left panel), blocking of hPDL1 to hPD1 (bottom left panel), binding to mouse mPDL1-Fc (top right panel), and blocking of mPDL1 to hPD1 (bottom right panel) of antibodies tccR3κF8, tccR3κD9, tccR3λD7, tccR3λD7 sR3κF10, sR3λD7, and tccR3λF8.

| FIG. 3 | tccR3κF8 | tccR3κD9 | tccR3λD7 | tccR3κF10 | sR3λD7 | tccR3F8 |
|---|---|---|---|---|---|---|
| h_$EC_{50}$ | 0.13 | 0.0259 | 0.14 | 0.137 | 0.244 | 0.174 |
| h_$IC_{50}$ | 2.78 | 3.23 | 1.09 | 6.22 | 2.52 | 2.89 |
| m_$EC_{50}$ | ND | 1.31 | 0.13 | ND | ND | 0.13 |
| m_$IC_{50}$ | ND | 52.3 | 0.349 | ND | ND | 0.184 |

| FIG. 4 | control | R2κA6 | sR3λD7 | tccR3λD7 | tccR3κB7 | tccR3λH4 |
|---|---|---|---|---|---|---|
| h_$EC_{50}$ | 0.146 | 0.0909 | 0.129 | 0.0682 | 0.126 | 0.117 |
| h_$IC_{50}$ | 1.49 | 2 | 2.55 | 1.97 | 2.05 | 1.68 |
| m_$EC_{50}$ | ND | ND | ND | 0.0622 | ND | ND |
| m_$IC_{50}$ | ND | ND | ND | 1.58 | ND | ND |

TABLE 3

$EC_{50}$ on PDLI-293, MDA-MB-231, and mPDLI cells

| | PDLI-293 | MDA-MB-231 | mPDL1 |
|---|---|---|---|
| sR3λD7 | $1.377 \times 10^{-9}$ | $2.138 \times 10^{-10}$ | ND |
| tctR3κA8 | $1.179 \times 10^{-9}$ | $1.886 \times 10^{-10}$ | ND |
| tccR3κA11 | $8.731 \times 10^{-10}$ | $1.437 \times 10^{-10}$ | ND |
| tccR3λD7 | $1.153 \times 10^{-9}$ | $6.943 \times 10^{-10}$ | $3.413 \times 10^{-10}$ |
| tccR3κD9 | $7.886 \times 10^{-10}$ | $1.241 \times 10^{-8}$ | $4.004 \times 10^{-9}$ |
| tccR3λF8 | $1.335 \times 10^{-9}$ | $2.610 \times 10^{-10}$ | $3.695 \times 10^{-10}$ |
| tccR3κF8 | $7.430 \times 10^{-10}$ | $7.777 \times 10^{-11}$ | ND |
| tccR3κF10 | $9.143 \times 10^{-10}$ | $1.922 \times 10^{-8}$ | ND |
| tccR3λH4 | $1.410 \times 10^{-9}$ | $1.049 \times 10^{-9}$ | ND |
| tccR3κB7 | $9.732 \times 10^{-10}$ | $9.833 \times 10^{-11}$ | $2.688 \times 10^{-9}$ |
| tccR3κA4 | $9.062 \times 10^{-8}$ | 0.0001903 | $2.025 \times 10^{-10}$ |

Figure 6:
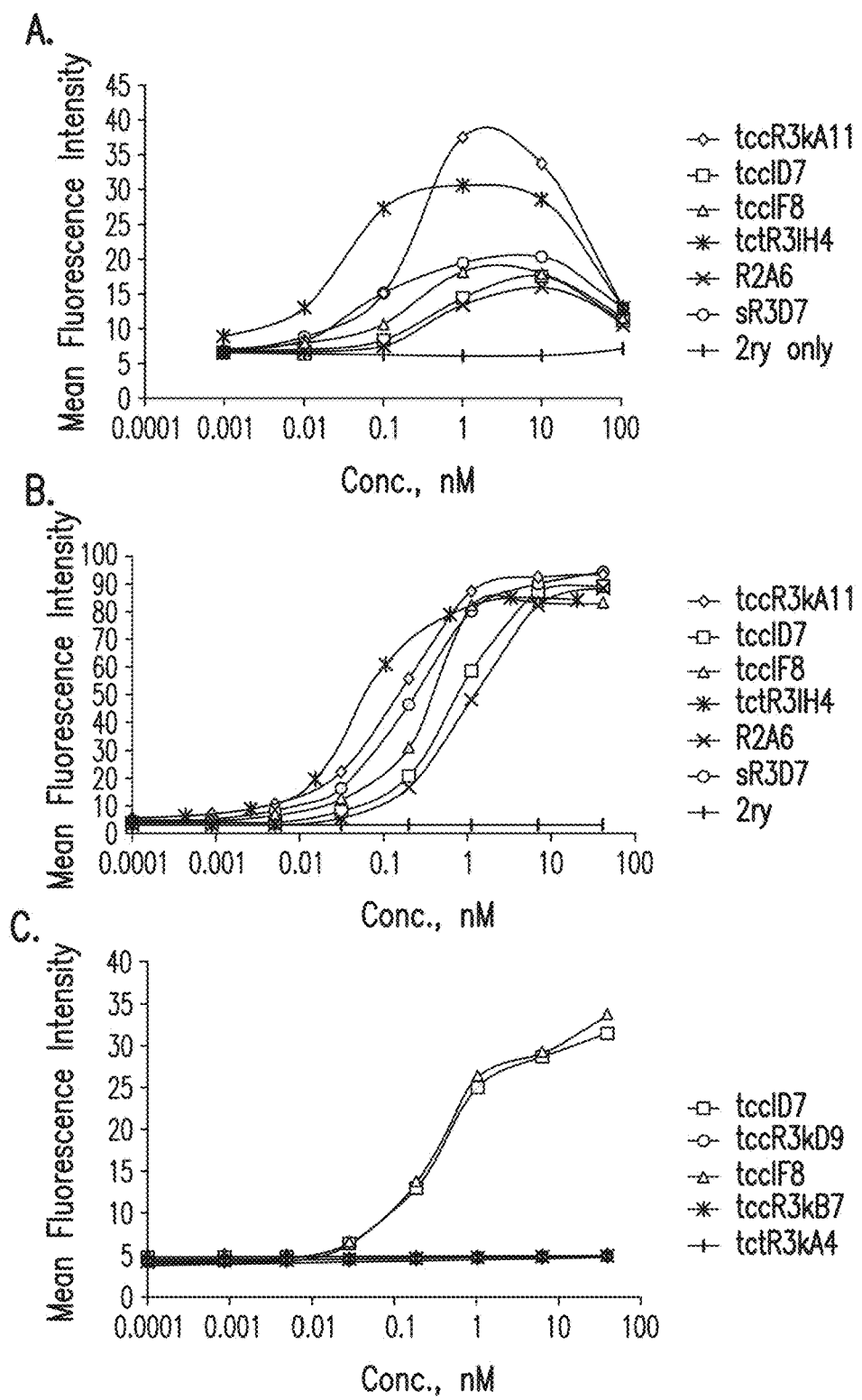
FIG. 6 depicts anti-PD-L1 antibodies binding to (A) human monocyte-derived dendritic cells, (B) human cancer cell line expressing PD-L1 MDA-MB-231 cells, and (C) mouse cell line expressing PD-L1 B16-F10.

These antibodies were also verified for binding on native cells expressing PD-L1 by binding to immature monocyte-derived dendritic cells (FIG. 6A), the human PD-L1-expressing breast cancer line MDA-MB-231 cells (FIG. 6B), the mouse PD-L1-expressing tumor line B16-F10 cells (FIG. 6C) as well as human activated CD4 and CD8 T cells. Functionally Active Anti-PD-L1 Antibodies Block PD-1 PD-L1 Interaction and Increase T Cell Proliferation and Activation High affinity binding anti-PD-L1 antibodies were evaluated for their function to block PD-1 PD-L1 interactions and increase T cell proliferation. Negatively purified CD4 T cells were activated in vitro with either αCD3 or αCD3 and PD-L1Fc coated beads in the presence of anti-PD-L1 antibodies. CD4 cells stimulated with αCD3 and PD-L1Fc coated beads showed lower proliferation and IFNγ as well as IL-2 secretions as compared to CD4 cells stimulated with αCD3 only coated beads. Addition of functionally active anti-PD-L1 antibodies to CD4 cultures stimulated with αCD3 and PD-L1Fc coated beads increases CD4 proliferation (measured by either total CD4 number or percentage of the proliferation marker Ki67) (FIG. 7A) as compared to cultures with no antibody added. Addition of functionally active blocking anti-PD-L1 antibodies to CD4 cultures with αCD3 and PD-L1Fc coated beads also increases cytokine secretions by CD4 (measured by ELISA of accumulated IFNγ and IL-2 in the supernatant).

Figure 7:
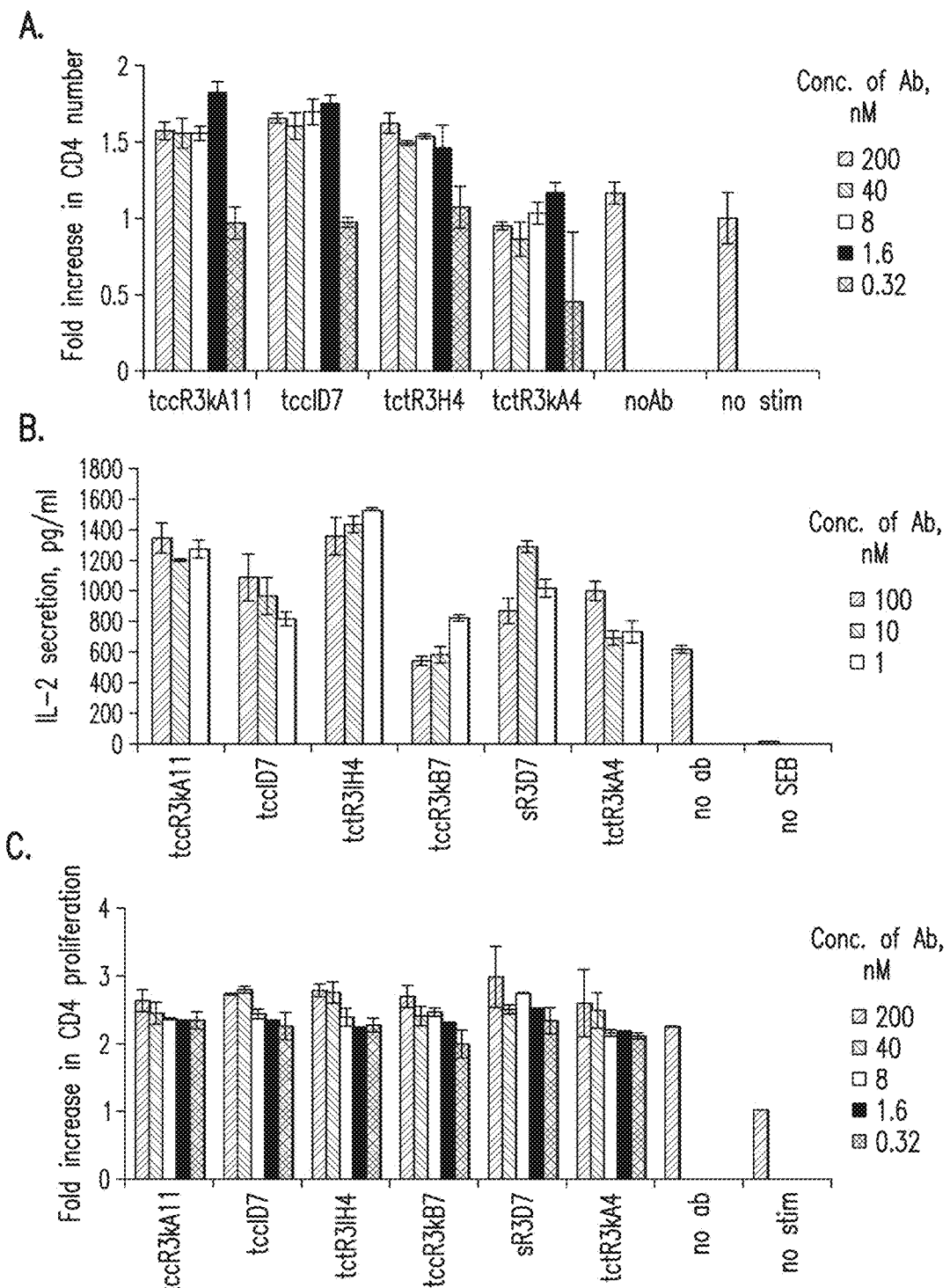
FIG. 7 shows functional blocking activity of anti-PD-L1 antibodies measured by (A) increase in CD4 proliferation when activated by αCD3 and PD-L1Fc coated beads, (B) increase in cytokine secretion in SEB-activated human PBMC, and (C) increase in CD4 proliferation in Mixed-Lymphocyte Reaction with mo-DC.

When PBMC isolated from whole blood are stimulated with the super antigen *Staphylococcus* Enterotoxin B (SEB) in the presence of anti-PD-L1 blocking antibodies, increase in cytokine secretions is observed. Supernatants of PBMC (previously frozen) cultured with SEB for 48 hours were collected, and IFNγ and IL-2 were measured by ELISA. No increase in T cells numbers were observed, but significant increases in the levels of IFNγ and IL-2 were observed in cultures of several anti-PD-L1 antibodies when compared to controls where no antibodies were added (FIG. 7B).

In addition, an increase in CD4 proliferation and activation is also observed in mixed-lymphocyte reaction (MLR) of CD4 T cells and mo-DC cultured in the presence of anti-PD-L1 blocking antibodies. Several of anti-PD-L1 antibodies increased CD4 proliferation in MLR when compared to cultures where no antibody was added (FIG. 7C). These antibodies also increased IFNγ and IL-2 secretion as evaluated by ELISA.

IL15 Increases Anti-PD-L1 Antibodies Effects on T Cell Proliferation and Activation In Vitro MLR of CD4 T cells and mo-DC in the presence of both anti-PD-L1 blocking antibodies and the cytokine IL15 resulted in significant increases in CD4 proliferation (FIG. 8A), IFNγ and IL-2 secretions when compared to cultures of CD4 and mo-DC with anti-PD-L1 antibodies alone. IL15 was added at equimolar concentrations as anti-PD-L1 antibodies in these assays. At lower anti-PD-L1 antibody and IL15 concentrations (0.5 nM, FIG. 8A), some synergistic effect on CD4 proliferation was observed.

Figure 8:
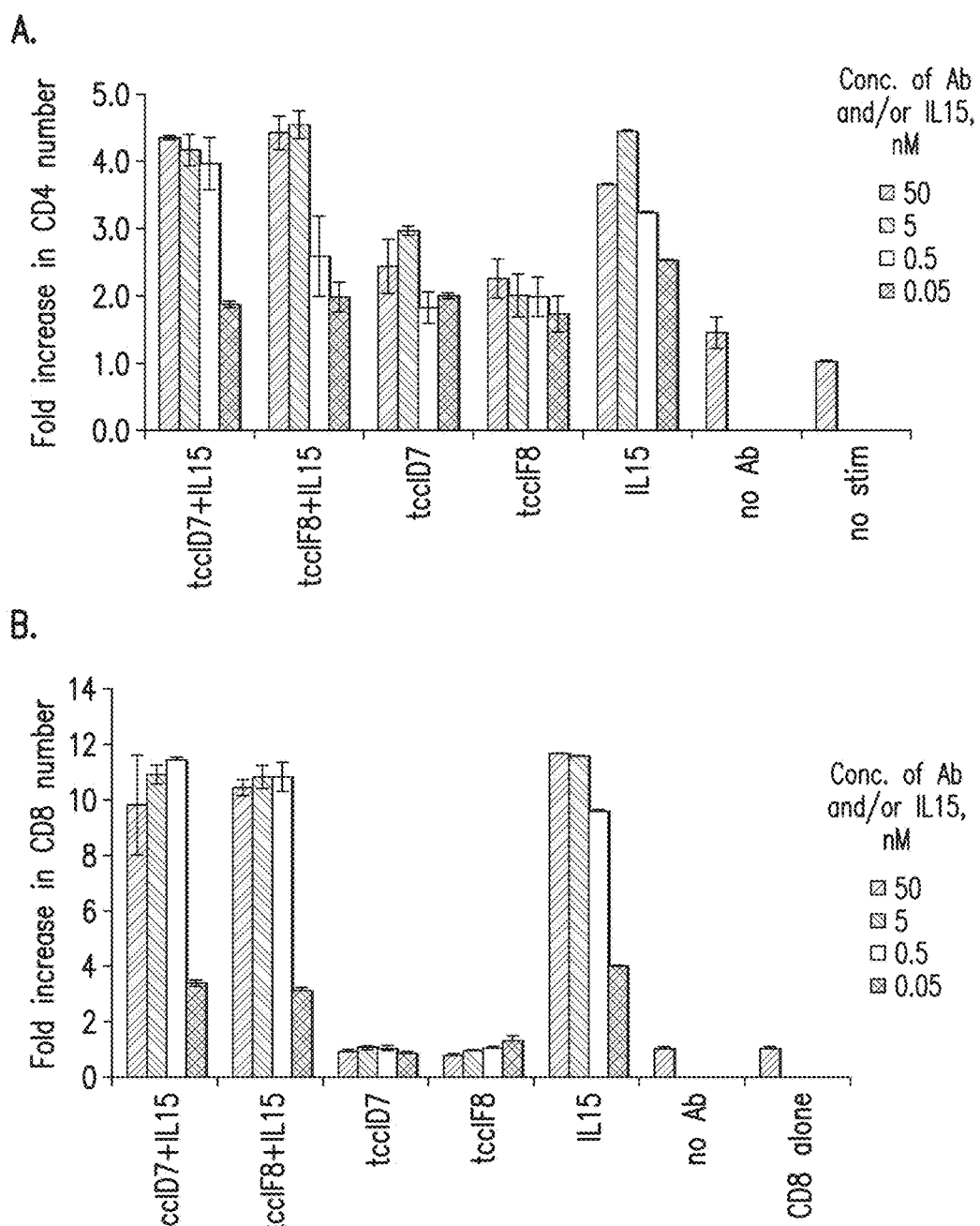
FIG. 8 shows CD4 and CD8 activation when both anti-PDL1 antibody and IL15 were present in (A) mixed-lymphocyte reaction with mo-DC, and (B) CD8 stimulation by αCD3 and PD-L1Fc coated beads.

Negatively purified CD8 from whole blood stimulated in vitro with αCD3 and PD-L1Fc coated beads also responds to IL15 in a dose-dependent fashion. Addition of IL15 to cultures of CD8 with αCD3 and PD-L1Fc coated beads and anti-PD-L1 antibodies resulted in large increases in CD8 proliferation (FIG. 8B).

Anti-PD-L1-IL15 Fusion Protein Targets IL15 to PD-L1-Expressing Antigen Presenting Cells and Increases Proliferation and Activation of Responding CD8 Cells Anti-PD-L1 antibody and IL15 fusion protein was constructed by linking the Fc domain of the antibody to the sushi-domain of IL15R and to IL15 molecule itself. The fusion of the IL15Rα sushi domain, IRD-11 exone3, linker and IL15 (designated "SD15") is provided as SEQ ID NO:261. SD15 was appended to the heavy chain c-terminal of conventional IgG. The fusion protein with IL15Rα sushi domain, IRD-11 exone3, linker and IL15 was appended to the heavy chain c-terminal of tccλD7 variable domain and IgG1 $C_H1$-CH2-CH3 variable domain (SEQ ID NO:262). The construct also included a K to S replacement at the end of the IgG1 heavy chain (1) to diminish the possibility of "G-K" cleavage; (2) to add the cloning site (BamHI) to the vector.

The light chain is that of a conventional antibody. Both the light chain and fusion heavy chain with or without LALA mutant were inserted to Dyax pBh1 vector for expression.

This fusion molecule is designate anti-PD-L1-sushi domain-IL15 or anti-PD-L1-SD15. A different version of the fusion protein where IL15 was linked to the Fc instead of the sushi domain was also constructed, and as this fusion protein did not have IL15 functional activity we used this protein as negative control in some assays (termed anti-PD-L1-SD15neg).

Figure 9:
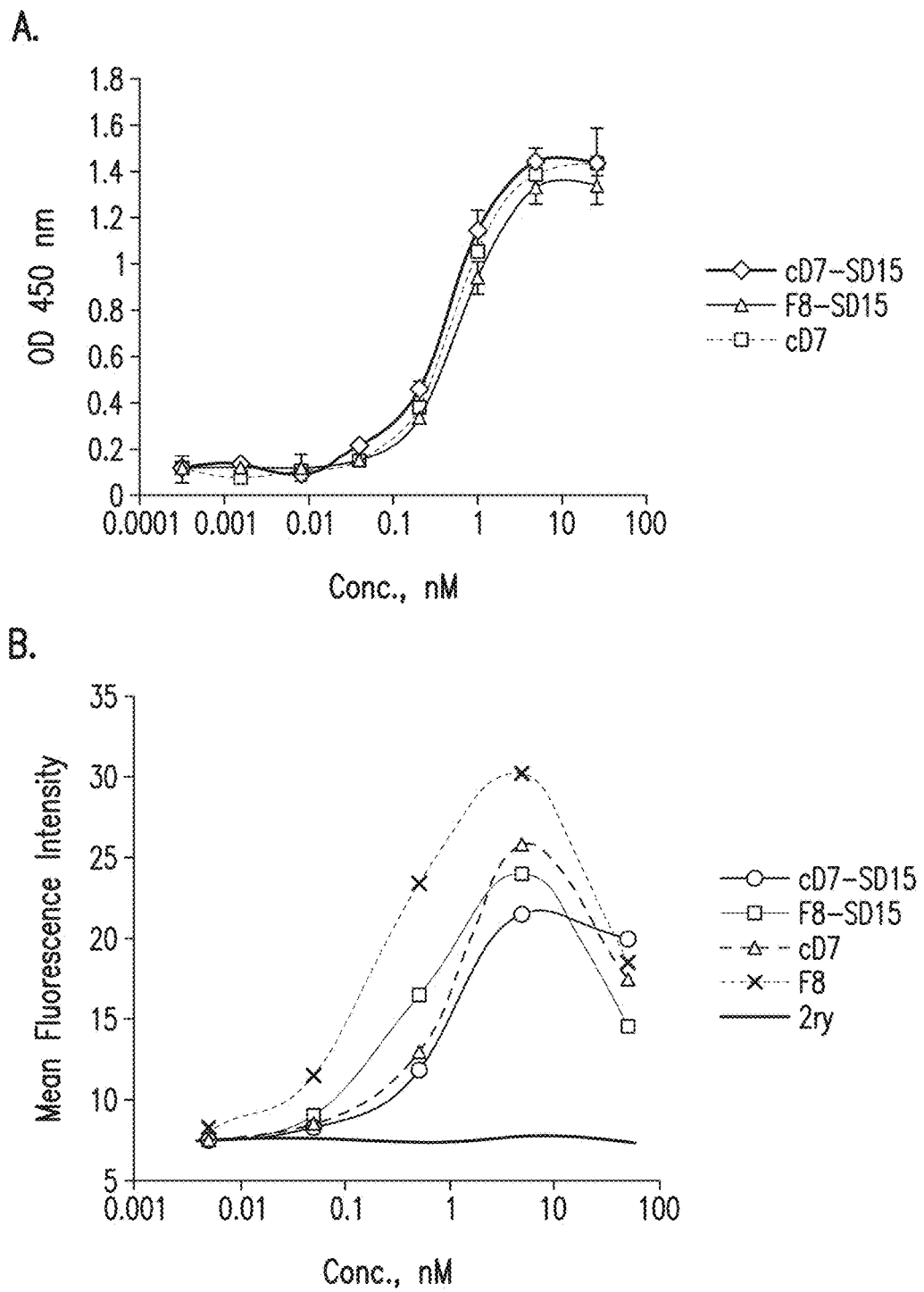
FIG. 9 shows anti-PD-L1-sushi domain-IL15 (termed anti-PDL1-SD15) fusion proteins retain binding to PD-L1 as measured by (A) solid-phase ELISA, and (B) binding to CD4 activated by αCD3 coated beads.

No significant change was observed when binding of anti-PD-L1-SD15 fusion proteins were compared to anti-PD-L1 antibodies in solid-phase PD-L1Fc binding ELISA assay (FIG. 9A). Some changes in binding affinity to activated CD4 cells expressing PD-L1 was observed when binding of anti-PD-L1-SD15 proteins were compared to their respective original anti-PD-L1 antibodies (FIG. 9B). Anti-PD-L1-SD15 proteins have lower affinity to cells expressing PD-L1 when compared to their respective anti-PD-L1 antibodies; although, there might be differences in binding of the secondary antibody to the bound anti-PD-L1-SD15 versus bound anti-PD-L1 on the surface of cells.

Figure 10:
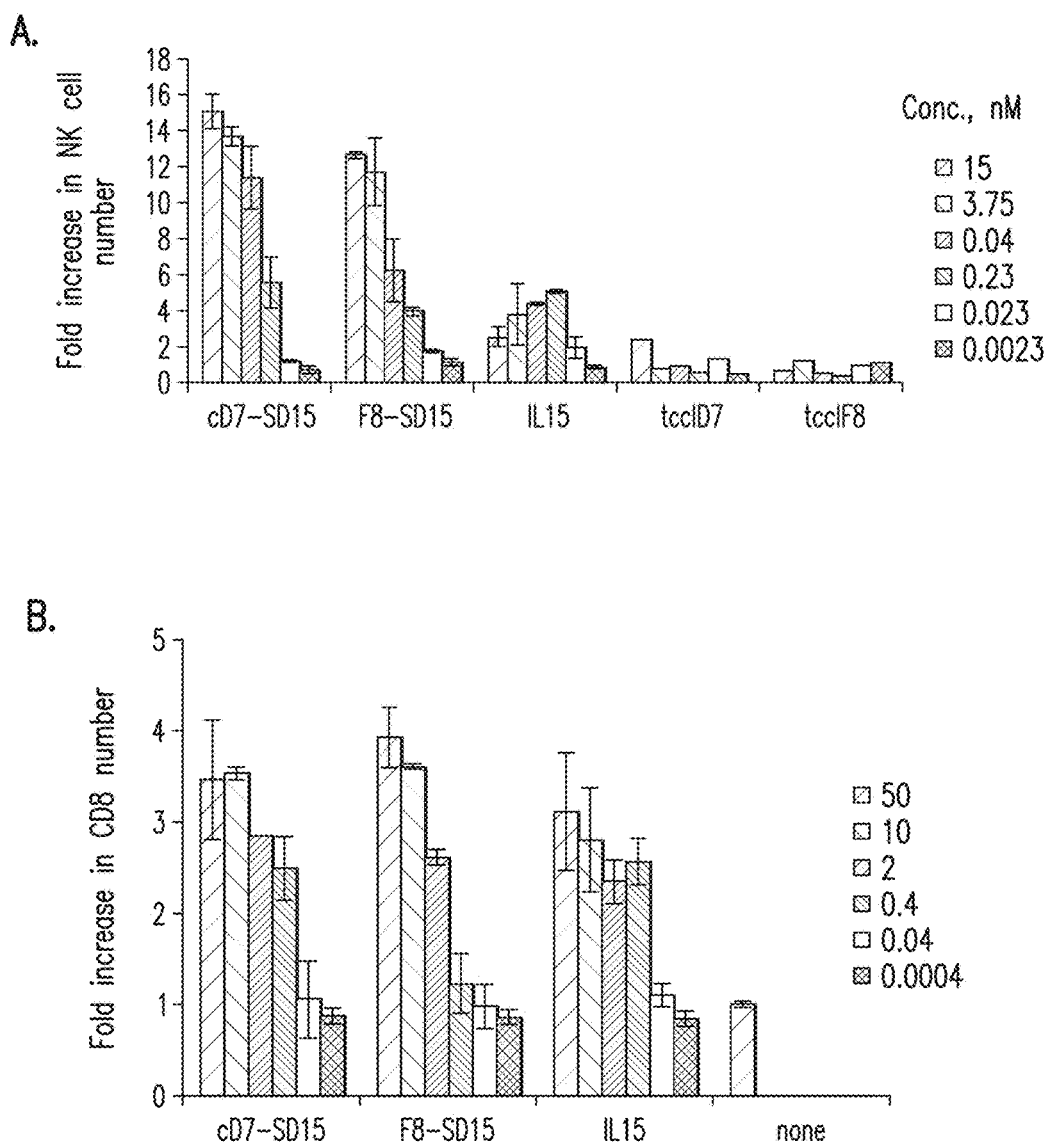
FIG. 10 shows PBMC cultured in vitro with anti-PD-L1-SD15 fusion proteins resulted in increased NK cell number (A), increased CD8 cell number (B) and activation status as measured by % granzymeB (C). No effect was observed on CD4 cells (D).
Figure 10:
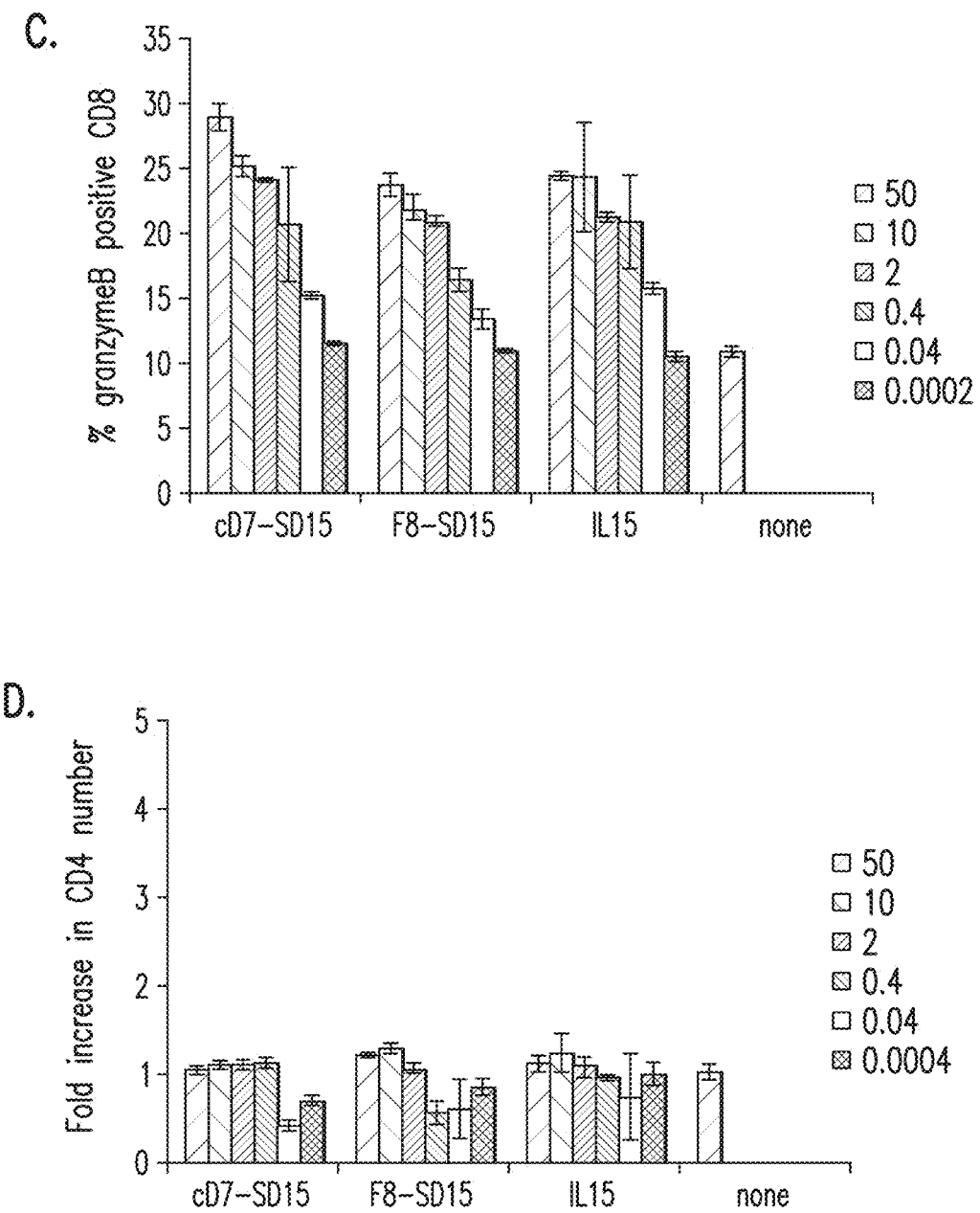

To evaluate the function of IL15 of anti-PD-L1-SD15 fusion proteins, PBMC isolated from whole blood was cultured in the presence of either anti-PD-L1-SD15 fusion proteins or IL15. No other stimulations were added to the cultures. Anti-PD-L1-SD15 fusion proteins increased NK cell number (FIG. 10A), increased CD8 proliferation (FIG. 10B) and activation (measured by % of granzymeB positive CD8, FIG. 10C) similarly as IL15. No significant increase in CD4 numbers were observed for all cultures (FIG. 10D).

To assess anti-PD-L1-SD15 activity on CD8, these fusion proteins were added to CD8 cultures in the presence of either αCD3 or αCD3 and PDL1Fc coated beads. Anti-PD-L1-SD15 increased CD8 proliferation significantly when PDL1Fc was present on the antigen presenting cells, αCD3 and PDL1Fc coated beads in this case (FIG. 11A, no PD-L1Fc versus FIG. 11B, with PD-L1Fc on the beads). Moreover, significant increase of CD8 activation was also observed. cD7-SD15 lowers the effective dose needed to activate CD8 as measured by increase in % of granzymeB positive CD8 cells (FIG. 12A) and IFNγ secretion (FIG. 12B) by about ten-fold. cD7-SD15 also increases maximum level of CD8 activation when compared to IL15 (FIGS. 12A and B). When compared to addition of anti-PD-L1 antibody plus free IL15, the anti-PD-L1-SD15 fusion protein increased CD8 proliferation to a level higher than the combination added separately (FIG. 12C). These properties of anti-PD-L1-SD15 fusion protein will be beneficial in the setting of immunotherapy as lower doses of anti-PD-L1-SD15 fusion protein can be used to achieve a higher level of CD8 activation and proliferation. The high amplified response of CD8 to anti-PD-L1-SD15 fusion protein in cases where the antigen presenting cells express PD-L1 will be advantageous in achieving selective CD8 activation.

Cytotoxicity of Anti-PD-L1-IL15 Fusion Protein

Figure 15:
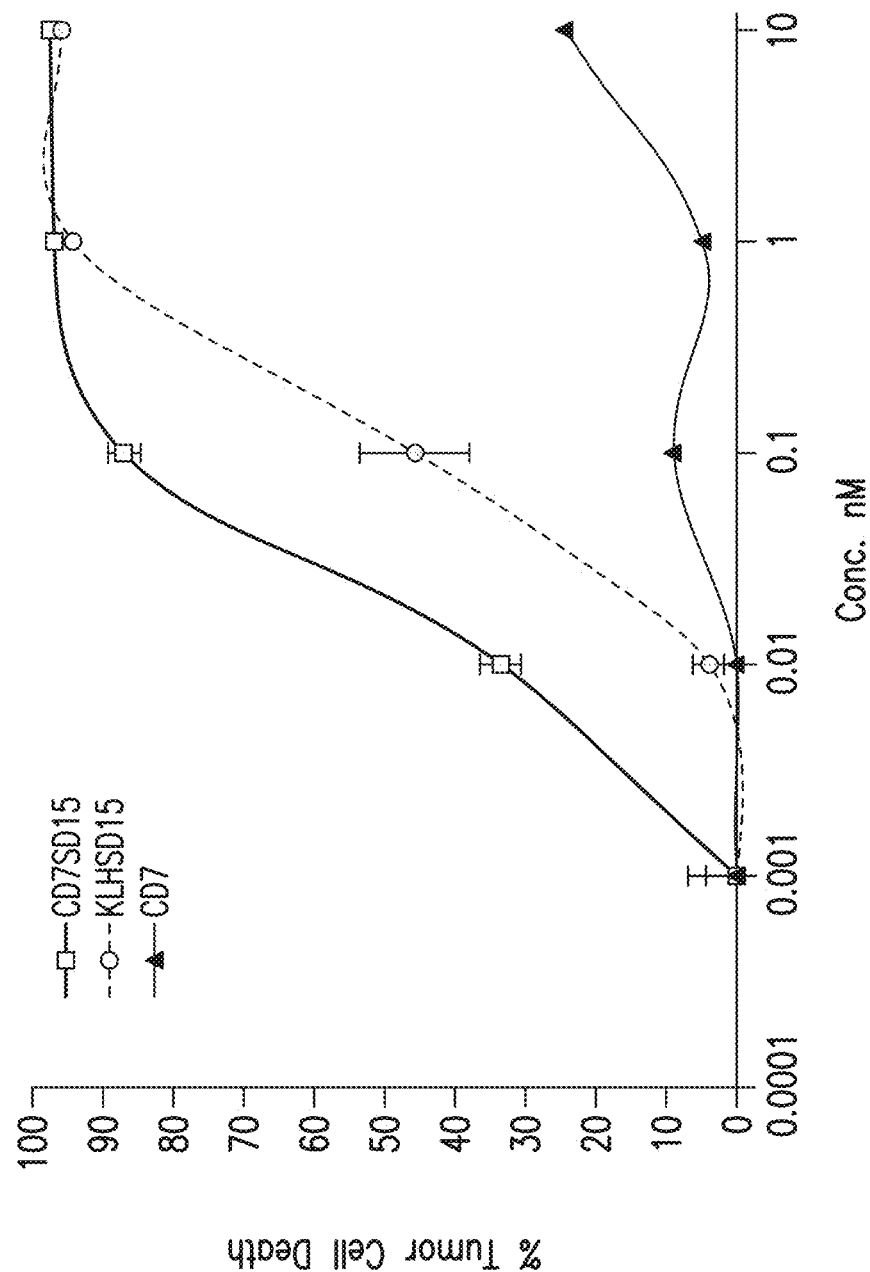
FIG. 15 shows cytoxicity of anti-PD-L1-SD15 fusion protein (CD7SD15) compared to the PD-L1 binding portion of the molecule alone (cD7) and a fusion protein containing a binding domain specific for KLH and the IL15 domain (KLHSD15). Human CD8 T cells and MAD-MB-231 tumor cells were co-cultured in IMDM supplemented with 10% FBS for 7 days. Tumor cell killing activity was assessed by the measurement of the number of dead tumor cells stained by Viability Dye eFluor 780 in FACS.
Figure 16:
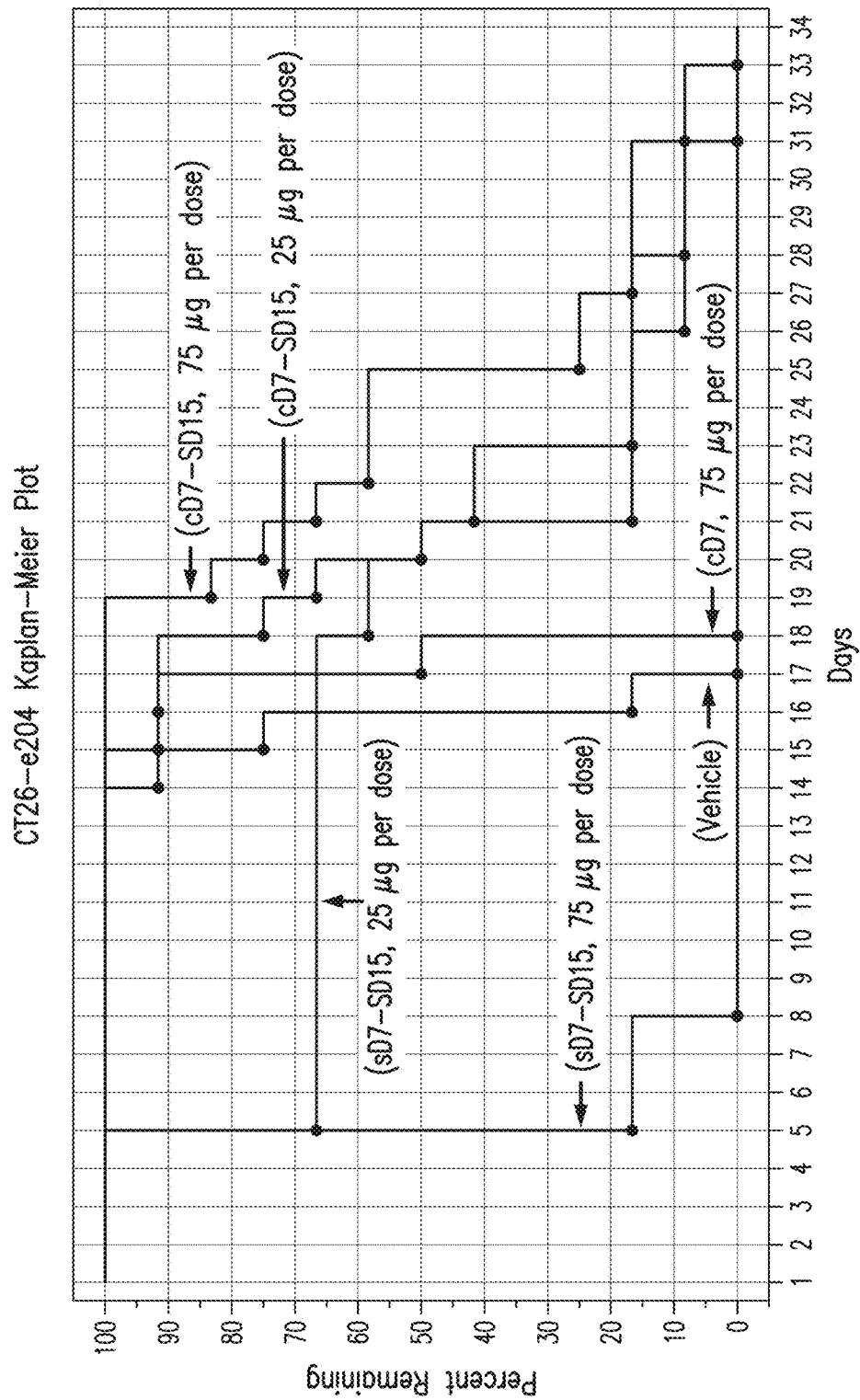
FIG. 16 shows anti-PD-L1-SD15 fusion protein prolonged the survival rate of mice bearing PD-L1 expressing tumors. Balb/c mice were intravenously injected with 2×10$^5$ murine CT26 colon tumor cells. 24 hrs later, mice received i.p. administration of the anti-PD-L1 antibody cD7 (purple line: 75 ug per dose), anti-PD-L1-SD15 fusion protein cD7-SD15 (green line: 75 ug per dose, blue line: 25 ug per dose) or sD7-SD15 (Grey line: 75 ug per dose, Red line: 25 ug per dose) twice a week in the first week then once weekly in the rest of treatment course. Mice in control groups received an equal volume of saline or normal IgG solution. Survival rate was measured by using Kaplan-Meier Plot.

To determine whether anti-PD-L1-SD15 fusion protein will increase IL15 induced cytotoxicity of CD8 T cells to PD-L1 expressing tumor cells, CD8 T cells were co-cultured with human PD-L1 expressing MAD-MB-231 tumor cells in the presence of anti-PD-L1-SD15 fusion protein or anti-KLH-SD15, which has no binding activity to PD-L1 expressing tumor cells, for 7 days prior to the measurement of tumor cell death. Human CD8 T cells and the tumor cells were co-cultured in IMDM supplemented with 10% FBS for 7 days. Tumor cell killing activity was assessed by the measurement of the number of dead tumor cells stained by Viability Dye eFluor 780 in FACS. The CD8 T cell mediated cytotoxicity of MDA-MB-231 was significantly enhanced by anti-PD-L1-SD15 fusion protein in comparison to the treatment with anti-KLH-SD15 in the co-culture (FIG. 15). Moreover, PD-L1-SD15 fusion protein cD7-SD15 significantly increased the survival rate of mice bearing PD-L1 expressing tumor cells in the tumor model of mice intravenously injected with murine CT26 colon tumor cells in comparison to the mice treated with vehicle or PD-L1-SD15 fusion protein sD7-SD15, which does not have binding activity to murine PD-L1 (FIG. 16). These results indicate that the targeting IL15 stimulated immunological effector cells to PD-L1 overexpressed tumor sites by the bifunctional anti-PD-L1-SD15 fusion protein has advantage to enhance antitumor immunity while minimize side effects. This type of bifunctional antibody cytokine fusion proteins has potential as novel immunomodulatory therapeutics to achieve greater antitumor efficacy in the control of tumor progression.

Affinity Maturation

Variants of the tccλD7 heavy chain were produced by introducing amino acid substitutions at three of the methionine positions in CDR-1H and screening for improved affinity. More particularly, a library containing about 1×10⁸ variants of CDRH1 of tccλD7 was generated in which the first, second and fourth methionine positions were simultaneously varied. The library was panned on recombinant human PDL1-Fc (PDL1 ECD and human Fc fusion protein, Q9NZQ7) or murine PDL1-Fc (Q9EP73) which were immobilized on immune-tubes for four rounds. The ELISA positive clones from rounds 3 and 4 were sequenced. The unique clones were compared by competition ELISA. Table 4 shows the amino acid substitutions observed in 25 variants obtained from the screen, with SEQ ID NOs: for the affinity matured CDR-1H sequences and heavy chain variable domains containing the CDRs. The amino acid sequences of these variants are also set forth the sequence listing as indicated in Table 1.

TABLE 4

CDR-H1 sequences of affinity matured variants of tccλD7.

| tccλD7 | G | F | T | F | S | M | Y | M | M | M | CDR-1H SEQ ID NO | VH |
|---|---|---|---|---|---|---|---|---|---|---|---|---|
| #101 | — | — | — | — | — | A | — | A | — | A | 264 | 265 |
| #102 | — | — | — | — | — | A | — | R | — | F | 266 | 267 |
| #103 | — | — | — | — | — | A | — | L | — | V | 268 | 269 |
| #104 | — | — | — | — | — | A | — | V | — | F | 270 | 271 |
| #105 | — | — | — | — | — | A | — | V | — | S | 272 | 273 |
| #106 | — | — | — | — | — | G | — | L | — | V | 274 | 275 |
| #107 | — | — | — | — | — | G | — | Q | — | L | 276 | 277 |
| #108 | — | — | — | — | — | G | — | S | — | F | 278 | 279 |
| #109 | — | — | — | — | — | G | — | W | — | A | 280 | 281 |
| #110 | — | — | — | — | — | Q | — | L | — | Y | 282 | 283 |
| #111 | — | — | — | — | — | Q | — | V | — | F | 284 | 285 |
| #112 | — | — | — | — | — | Q | — | Y | — | Y | 286 | 287 |
| #113 | — | — | — | — | — | S | — | L | — | S | 288 | 289 |
| #114 | — | — | — | — | — | S | — | L | — | V | 290 | 291 |
| #115 | — | — | — | — | — | S | — | L | — | T | 292 | 293 |
| #116 | — | — | — | — | — | S | — | Q | — | V | 294 | 295 |
| #117 | — | — | — | — | — | S | — | S | — | A | 296 | 297 |
| #118 | — | — | — | — | — | S | — | V | — | F | 298 | 299 |
| #119 | — | — | — | — | — | S | — | V | — | S | 300 | 301 |
| #120 | — | — | — | — | — | S | — | V | — | Y | 302 | 301 |
| #121 | — | — | — | — | — | S | — | Y | — | F | 304 | 305 |
| #122 | — | — | — | — | — | S | — | Y | — | V | 306 | 307 |
| #123 | — | — | — | — | — | Y | — | S | — | V | 308 | 309 |
| #124 | — | — | — | — | — | W | — | L | — | A | 310 | 311 |
| #125 | — | — | — | — | — | W | — | Q | — | S | 312 | 313 |

Figure 17:
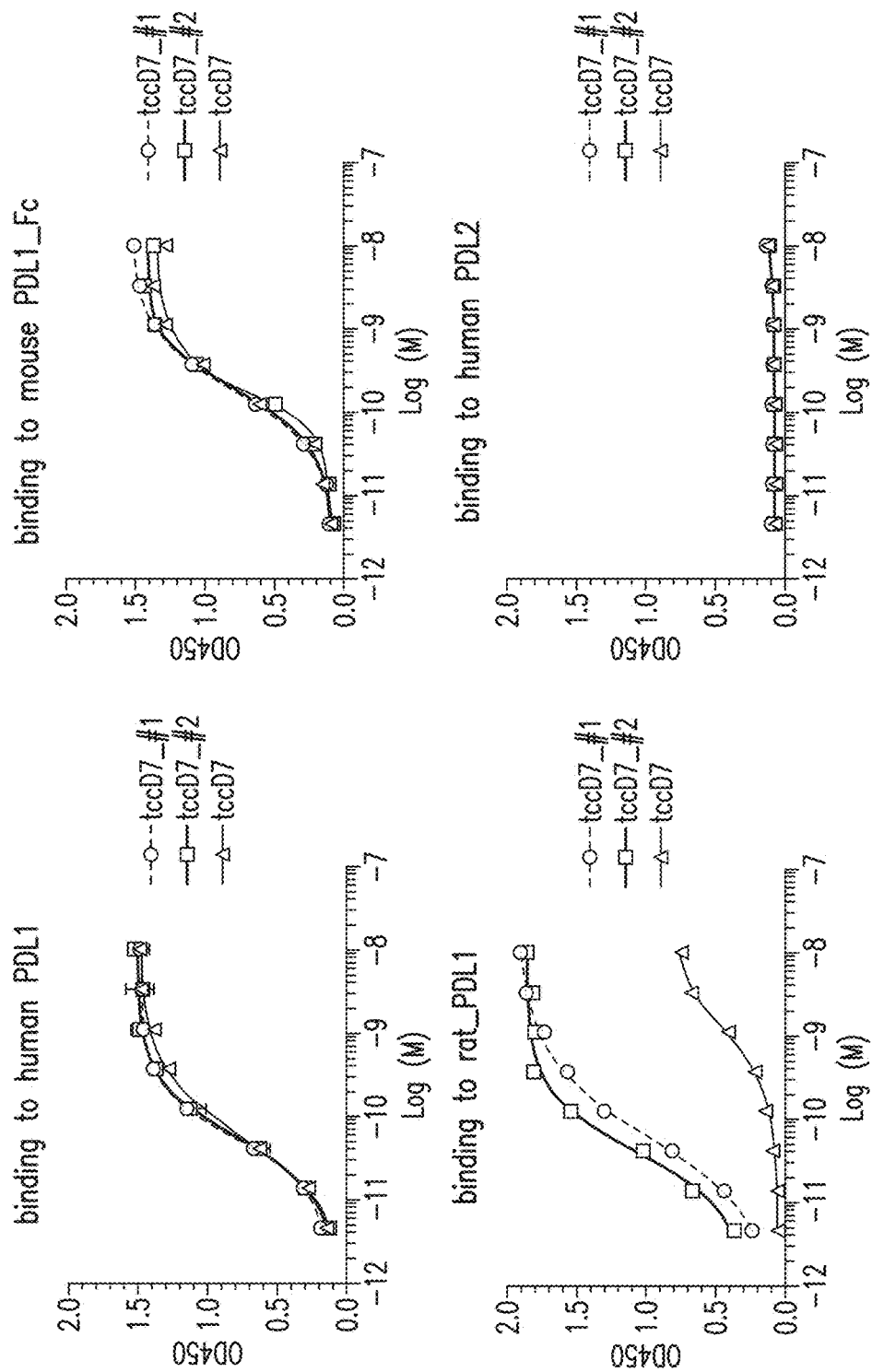
FIG. 17 shows binding of two affinity matured anti-PDL1 antibdodies to soluble human PDL1, soluble mouse PDL1, and soluble rat PDL1, and no binding to human PDL2.
Figure 19:
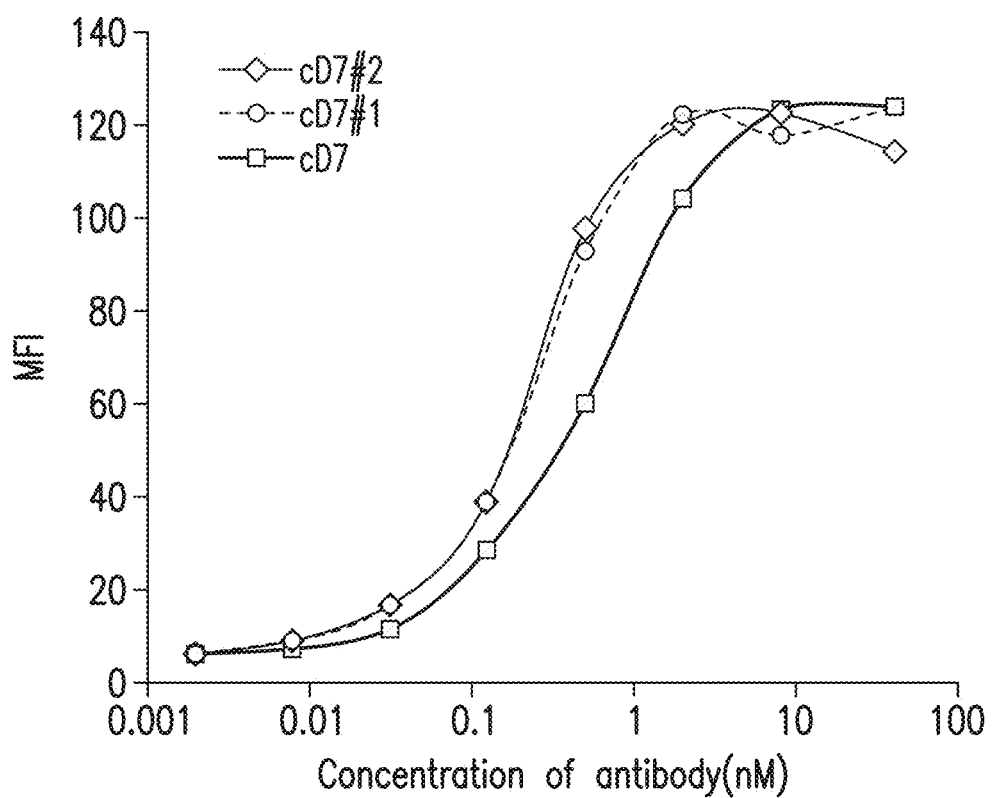
FIG. 19 shows two affinity matured variants of anti-PD-L1 antibodies tccλD7 have higher binding activity to PD-L1 expressing human MDA-MB-231 tumor cells as measured by flow cytometry.

Two variants, tccD7_#114 and tccD7_#102 (also respectively referred to herein as tccD7_#1 and tccD7_#2) were converted to IgG and also to an IgG form containing two Leu-Ala substitutions in the hinge region for reduced ADCC, as described elsewhere herein. The antibodies were expressed and purified for the further characterization. Improved binding to soluble PDL1 is shown in FIG. 17 for the two affinity matured variants. FIG. 18 shows the two variants blocked binding of human PD1 to human PDL1 (left panel) and blocked binding of mouse PD1 to mouse PDL1 (right panel). The variants wlao demonstrated higher binding activity to MDA-MB-231 cells compared to the parent (FIG. 19).

Figure 20:
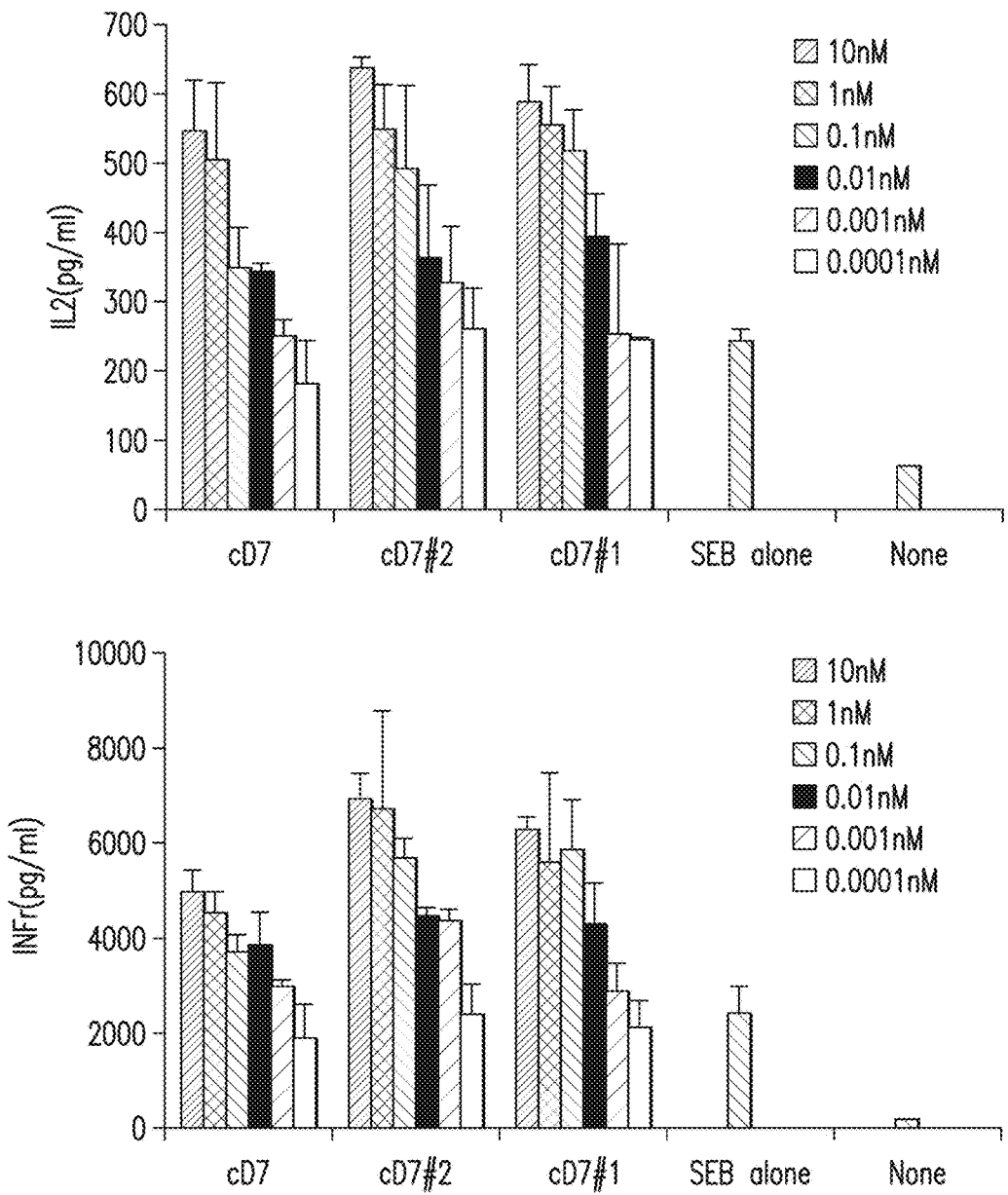
FIG. 20 shows affinity matured variants of anti-PD-L1 antibodies tccλD7 having increased potency to promote production of Th1 cytokines IL2 (top panel) and IFNγ (bottom panel).

The affinity matured variants were tested for their ability to promote production of Th1 cytokines IL2 and IFNγ. PBMC isolated from whole blood were stimulated with the super antigen Staphylococcus Enterotoxin B (SEB, 0.1 ug/mL) in the presence of anti-PD-L1 antibodies. Supernatants of PBMC cultured with SEB for 7 days were collected, and IFNγ and IL-2 were measured by ELISA. Significant increases in the levels of IFNγ and IL-2 were observed in cultures with the variants of anti-PD-L1 antibodies cD7_#1 and #2 when compared to cD7 (FIG. 20).

Several fusion protein variants comprising a PD-L1 binding domain, an IL15R a sushi domain and IL15 were constructed. Certain constructs include a linker between the IL15R a sushi domain and the IL15 portion. In one construct, 11 amino acids of exon 3 present in the c-terminal of the IL15 receptor α sushi domain were replaced with "GS" linkers of various lengths. GS linkers include SGGSGGGGSGGGSGGGGS (SEQ ID NO:324; 18 amino acids), SGGSGGGGSGGGSGGGGSLQ (SEQ ID NO:314; 20 amino acids), SGGGGSGGGGSGGGGSGGGGSGGGG (SEQ ID NO:316; 25 amino acids), SGGGGSGGGGSGGGGSGGGGSGGGGSGGGG (SEQ ID NO:318; 30 amino acids), SGGGGSGGGGSGGGGSGGGGSGGGGSGGGGSGGGGSGGGG (SEQ ID NO:320; 40 amino acids), and SGGGGSGGGGSGGGGSGGGGSGGGGSGGGGSGGGGSGGGGSGGGGSGGGG (SEQ ID NO:322; 50 amino acids) in constructs having SEQ ID NOS:325, 315, 317, 319, 321, and 323, respectively.

Fusion proteins were expressed in HEK293 cells, transiently or stably, and purified by protein A column chromatography according to manufacturers instructions. In certain experiments, to stabilize the association between the Ig heavy and light chain constant domains of the anti-PD-L1 portion of the molecule, the C-terminal serine of the lambda light chain was deleted, referred to herein by the designation "ds."

Figure 21:
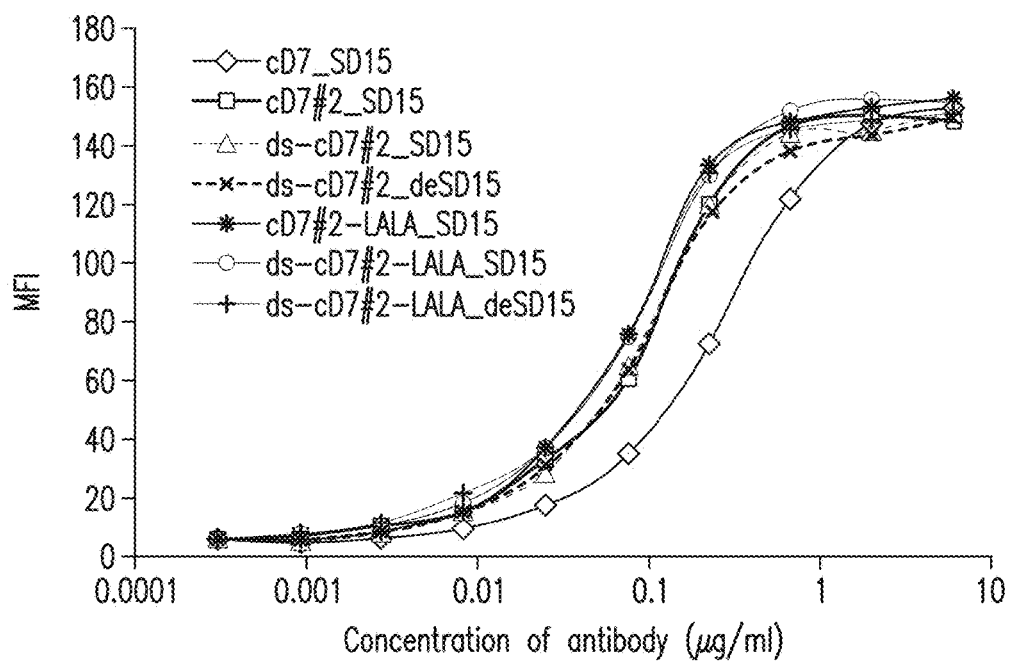
FIG. 21 shows binding of fusion proteins of the invention to PD-L1-expressing MDA-MB-231 tumor cells.
Figure 22:
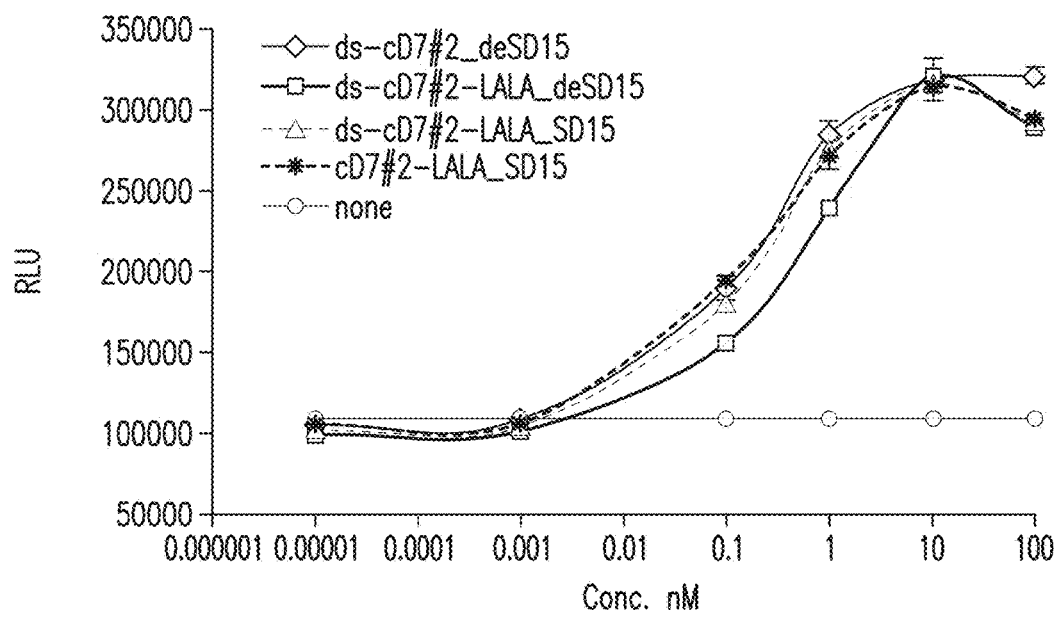
FIG. 22 shows stimulatory activity of proteins of the invention on IL15-responsive human megakaryoblastic leukemia cells.

Fusion proteins containing the tcc2 D7 affinity matured variant #102 with the sushi domain and IL15 (SEQ ID NO:325) were tested for binding to MDA-MB-231 by flow cytometry. All demonstrated imporved binding compared to the fusion protein containing tccλD7 (FIG. 21). The fusion proteins containing the tccλD7 affinity matured variant #102 were also confirmed to have stimulatory activity on IL15-responsive human megakaryoblastic leukemia cells. Cells were cultured with anti-PD-L1-SD15 fusion proteins in RPMI 1640 supplemented with 10% FBS and 20% conditioned medium of human bladder carcinoma 5637 cells for 48 hours. Cell proliferation was measured as Relative Luminescence Units (RLU) by CellTiter-Glo® Luminescent Cell Viability Assay (FIG. 22).

Figure 24:
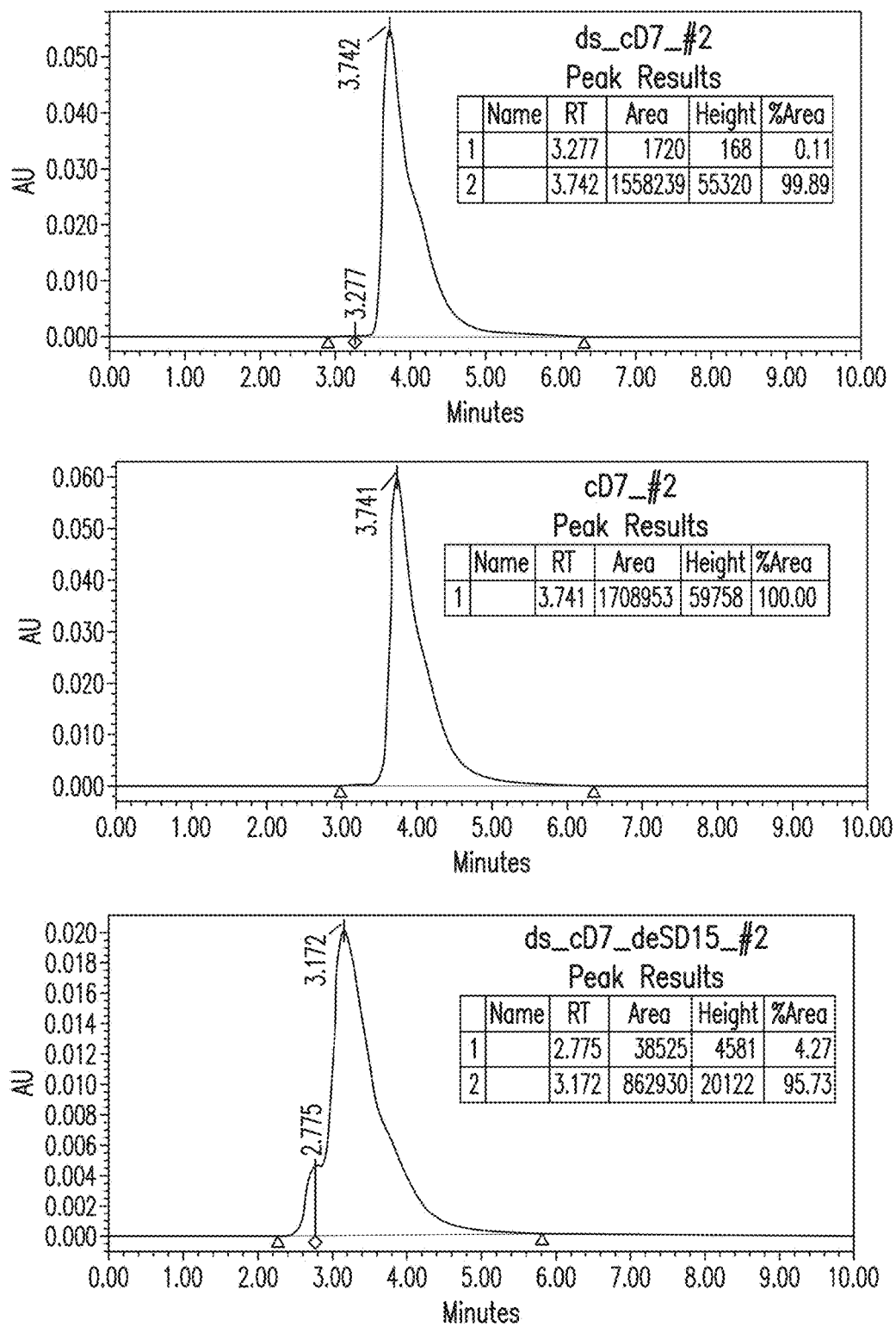
FIG. 24 shows the results of size exclusion chromatography for fusion proteins of the invention.
Figure 25:
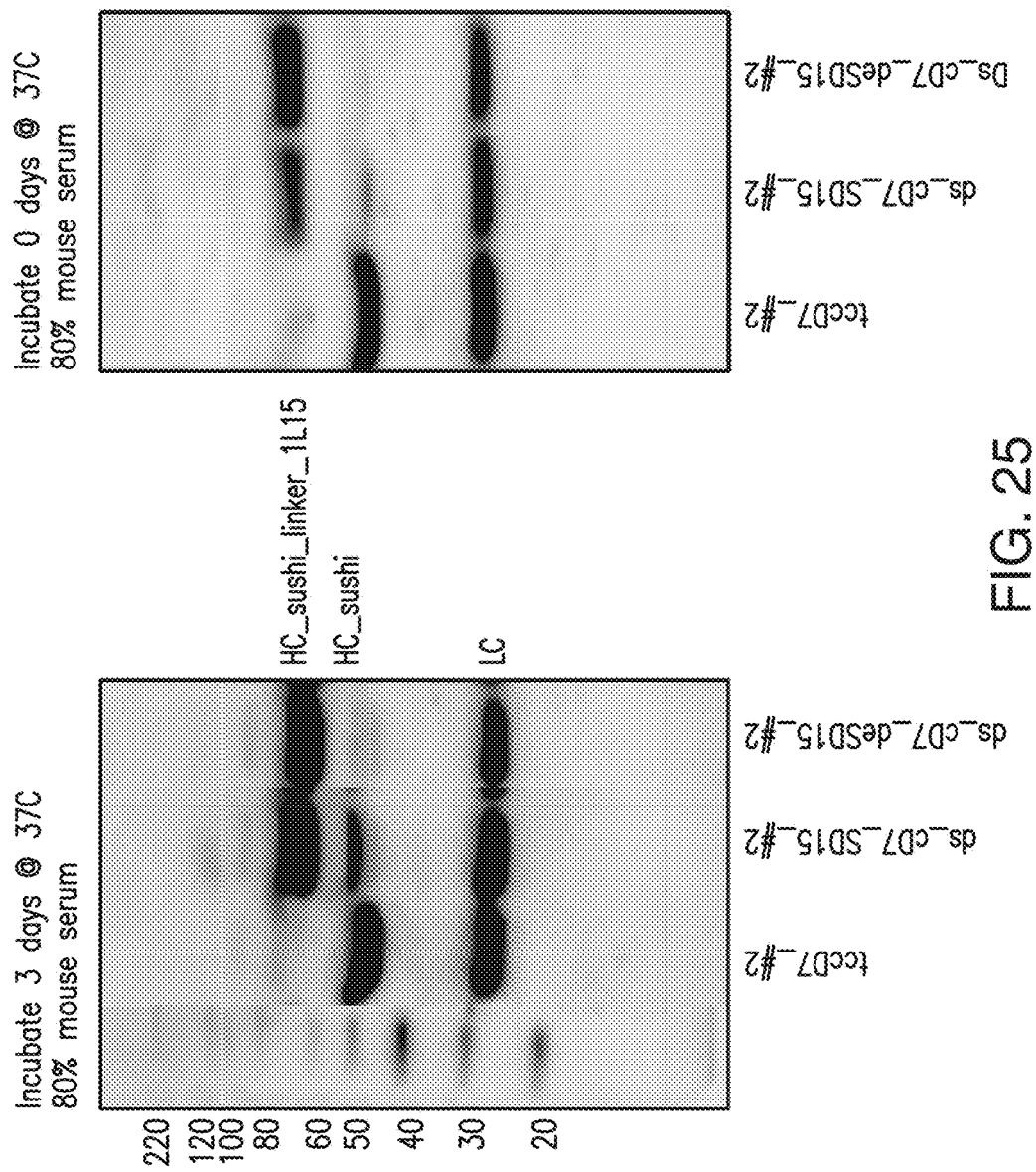
FIG. 25 shows serum stability for fusion proteins of the invention.

Analysis by size exclusion chromatography showed less than 5% aggregation (FIG. 24) and improved serum stability of the expressed fusion protein (FIG. 25).

What is claimed is:

1. A PD-L1 binding protein comprising a heavy chain CDR-1H comprising SEQ ID NO:121; a heavy chain CDR-2H comprising SEQ ID NO:123; a heavy chain CDR-3H comprising SEQ ID NO:125; a light chain CDR-1L comprising SEQ ID NO:127; a light chain CDR-2L comprising SEQ ID NO:128; and a light chain CDR-3L comprising SEQ ID NO:129.

2. The PD-L1 binding protein of claim 1, comprising a heavy chain variable domain comprising SEQ ID NO:126 or a sequence that is at least 85% identical to SEQ ID NO:126.

3. The PD-L1 binding protein of claim 1, comprising a light chain variable domain comprising SEQ ID NO:130 or a sequence that is at least 85% identical to SEQ ID NO:130.

4. The PD-L1 binding protein of claim 1, further comprising (i) an IL-15 receptor (M-15R) alpha sushi domain comprising amino acids 1-61 of SEQ ID NO:261; and (ii) IL-15 comprising amino acids 96-209 of SEQ ID NO:261, an amino acid sequence at least 95% identical to IL-15, or an IL-15R binding fragment thereof.

5. The PD-L1 binding protein of claim 4, further comprises a flexible linker joining the IL-15R alpha sushi domain to the IL-15 or IL-15R-binding fragment thereof.

6. The PD-L1 binding protein of claim 5, wherein the flexible linker comprises 15-20 amino acids which are predominantly serine and glycine.

7. The PD-L1 binding protein of claim 1, further comprising SEQ ID NO: 261.

* * * * *

SEQUENCE LISTING

<160> NUMBER OF SEQ ID NOS: 328

<210> SEQ ID NO 1

```
<211> LENGTH: 5
<212> TYPE: PRT
<213> ORGANISM: Artificial Sequence
<220> FEATURE:
<223> OTHER INFORMATION: Human antibody library

<400> SEQUENCE: 1

Leu Tyr Trp Met His
 1               5

<210> SEQ ID NO 2
<211> LENGTH: 7
<212> TYPE: PRT
<213> ORGANISM: Artificial Sequence
<220> FEATURE:
<223> OTHER INFORMATION: Human antibody library

<400> SEQUENCE: 2

Gly Phe Thr Phe Ser Leu Tyr
 1               5

<210> SEQ ID NO 3
<211> LENGTH: 17
<212> TYPE: PRT
<213> ORGANISM: Artificial Sequence
<220> FEATURE:
<223> OTHER INFORMATION: Human antibody library

<400> SEQUENCE: 3

Ser Ile Tyr Ser Ser Gly Val Met Thr Phe Tyr Ala Asp Ser Val Lys
 1               5                  10                  15

Gly

<210> SEQ ID NO 4
<211> LENGTH: 6
<212> TYPE: PRT
<213> ORGANISM: Artificial Sequence
<220> FEATURE:
<223> OTHER INFORMATION: Human antibody library

<400> SEQUENCE: 4

Tyr Ser Ser Gly Val Met
 1               5

<210> SEQ ID NO 5
<211> LENGTH: 9
<212> TYPE: PRT
<213> ORGANISM: Artificial Sequence
<220> FEATURE:
<223> OTHER INFORMATION: Human antibody library

<400> SEQUENCE: 5

Gly Ser Arg Val Asp Ala Phe Asp Ile
 1               5

<210> SEQ ID NO 6
<211> LENGTH: 118
<212> TYPE: PRT
<213> ORGANISM: Artificial Sequence
<220> FEATURE:
<223> OTHER INFORMATION: Human antibody library

<400> SEQUENCE: 6

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Leu Tyr
```

```
                 20                  25                  30
Trp Met His Trp Val Arg Gln Ala Pro Gly Lys Gly Leu Glu Trp Val
            35                  40                  45

Ser Ser Ile Tyr Ser Ser Gly Val Met Thr Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Arg Val Asp Ala Phe Asp Ile Trp Gly Gln Gly Thr
            100                 105                 110

Met Val Thr Val Ser Ser
        115

<210> SEQ ID NO 7
<211> LENGTH: 12
<212> TYPE: PRT
<213> ORGANISM: Artificial Sequence
<220> FEATURE:
<223> OTHER INFORMATION: Human antibody library

<400> SEQUENCE: 7

Arg Ala Ser Gln Ser Val Ser Ser Ser Tyr Leu Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Human antibody library

<400> SEQUENCE: 8

Gly Ala Ser Ala Arg Ala Ile
1               5

<210> SEQ ID NO 9
<211> LENGTH: 9
<212> TYPE: PRT
<213> ORGANISM: Artificial Sequence
<220> FEATURE:
<223> OTHER INFORMATION: Human antibody library

<400> SEQUENCE: 9

Gln Gln Ser Tyr Ser Ile Pro Ile Thr
1               5

<210> SEQ ID NO 10
<211> LENGTH: 108
<212> TYPE: PRT
<213> ORGANISM: Artificial Sequence
<220> FEATURE:
<223> OTHER INFORMATION: Human antibody library

<400> SEQUENCE: 10

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ala Arg Ala Ile Gly Val Pro Asp Arg Phe Arg
```

```
            50                  55                  60
Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Ser Tyr Ser Ile Pro
                 85                  90                  95

Ile Thr Phe Gly Pro Gly Thr Lys Val Asp Ile Lys
            100                 105
```

```
<210> SEQ ID NO 11
<211> LENGTH: 5
<212> TYPE: PRT
<213> ORGANISM: Artificial Sequence
<220> FEATURE:
<223> OTHER INFORMATION: Human antibody library

<400> SEQUENCE: 11

Pro Tyr Pro Met Trp
 1               5
```

```
<210> SEQ ID NO 12
<211> LENGTH: 7
<212> TYPE: PRT
<213> ORGANISM: Artificial Sequence
<220> FEATURE:
<223> OTHER INFORMATION: Human antibody library

<400> SEQUENCE: 12

Gly Phe Thr Phe Ser Pro Tyr
 1               5
```

```
<210> SEQ ID NO 13
<211> LENGTH: 17
<212> TYPE: PRT
<213> ORGANISM: Artificial Sequence
<220> FEATURE:
<223> OTHER INFORMATION: Human antibody library

<400> SEQUENCE: 13

Ser Ile Ser Pro Ser Gly Gly Phe Thr Phe Tyr Ala Asp Ser Val Lys
 1               5                  10                  15

Gly
```

```
<210> SEQ ID NO 14
<211> LENGTH: 6
<212> TYPE: PRT
<213> ORGANISM: Artificial Sequence
<220> FEATURE:
<223> OTHER INFORMATION: Human antibody library

<400> SEQUENCE: 14

Ser Pro Ser Gly Gly Phe
 1               5
```

```
<210> SEQ ID NO 15
<211> LENGTH: 13
<212> TYPE: PRT
<213> ORGANISM: Artificial Sequence
<220> FEATURE:
<223> OTHER INFORMATION: Human antibody library

<400> SEQUENCE: 15

Asp Arg Val Ser Trp Asn Asp Tyr Thr Gly Met Asp Val
 1               5                  10
```

```
<210> SEQ ID NO 16
<211> LENGTH: 122
<212> TYPE: PRT
<213> ORGANISM: Artificial Sequence
<220> FEATURE:
<223> OTHER INFORMATION: Human antibody library

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Trp Trp Val Arg Gln Ala Pro Gly Lys Gly Leu Glu Trp Val
        35                  40                  45

Ser Ser Ile Ser Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Val Ser Trp Asn Asp Tyr Thr Gly Met Asp Val Trp
            100                 105                 110

Gly Gln Gly Thr Thr Val Thr Val Ser Ser
        115                 120

<210> SEQ ID NO 17
<211> LENGTH: 11
<212> TYPE: PRT
<213> ORGANISM: Artificial Sequence
<220> FEATURE:
<223> OTHER INFORMATION: Human antibody library

<400> SEQUENCE: 17

Arg Ala Ser Glu Ser Ile Gly Lys Phe Leu Asn
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Human antibody library

<400> SEQUENCE: 18

Ser Ala Ser Ser Leu Gln Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Human antibody library

<400> SEQUENCE: 19

Gln Gln Ser Phe Asp Met Pro Ile Thr
1               5

<210> SEQ ID NO 20
<211> LENGTH: 107
<212> TYPE: PRT
<213> ORGANISM: Artificial Sequence
<220> FEATURE:
<223> OTHER INFORMATION: Human antibody library
```

```
<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Gly Lys Phe
                20                  25                  30

Leu Asn Trp Tyr Gln Gln Lys Pro Gly Lys Ala Pro Thr Leu Leu Ile
            35                  40                  45

His Ser Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Thr Thr Tyr Phe Cys Gln Gln Ser Phe Asp Met Pro Ile
                85                  90                  95

Thr Phe Gly Gln Gly Thr Gln Leu Glu Ile Lys
            100                 105

<210> SEQ ID NO 21
<211> LENGTH: 5
<212> TYPE: PRT
<213> ORGANISM: Artificial Sequence
<220> FEATURE:
<223> OTHER INFORMATION: Human antibody library

<400> SEQUENCE: 21

Ala Tyr Ile Met Gly
1               5

<210> SEQ ID NO 22
<211> LENGTH: 7
<212> TYPE: PRT
<213> ORGANISM: Artificial Sequence
<220> FEATURE:
<223> OTHER INFORMATION: Human antibody library

<400> SEQUENCE: 22

Gly Phe Thr Phe Ser Ala Tyr
1               5

<210> SEQ ID NO 23
<211> LENGTH: 17
<212> TYPE: PRT
<213> ORGANISM: Artificial Sequence
<220> FEATURE:
<223> OTHER INFORMATION: Human antibody library

<400> SEQUENCE: 23

Tyr Ile Ser Ser Ser Gly Gly Trp Thr Ala Tyr Ala Asp Ser Val Lys
1               5                   10                  15

Gly

<210> SEQ ID NO 24
<211> LENGTH: 6
<212> TYPE: PRT
<213> ORGANISM: Artificial Sequence
<220> FEATURE:
<223> OTHER INFORMATION: Human antibody library

<400> SEQUENCE: 24

Ser Ser Ser Gly Gly Trp
1               5
```

<210> SEQ ID NO 25
<211> LENGTH: 10
<212> TYPE: PRT
<213> ORGANISM: Artificial Sequence
<220> FEATURE:
<223> OTHER INFORMATION: Human antibody library

<400> SEQUENCE: 25

Asp Gln Asp Gly Tyr Asn Asp Phe Asp Tyr
1               5                   10

<210> SEQ ID NO 26
<211> LENGTH: 119
<212> TYPE: PRT
<213> ORGANISM: Artificial Sequence
<220> FEATURE:
<223> OTHER INFORMATION: Human antibody library

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Ile Met Gly Trp Val Arg Gln Ala Pro Gly Lys Gly Leu Glu Trp Val
        35                  40                  45

Ser Tyr Ile Ser Ser Ser Gly Gly Trp Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Asp Gln Asp Gly Tyr Asn Asp Phe Asp Tyr Trp Gly Gln Gly
            100                 105                 110

Thr Leu Val Thr Val Ser Ser
        115

<210> SEQ ID NO 27
<211> LENGTH: 11
<212> TYPE: PRT
<213> ORGANISM: Artificial Sequence
<220> FEATURE:
<223> OTHER INFORMATION: Human antibody library

<400> SEQUENCE: 27

Arg Ala Ser Gln Ser Ile Ser Ser Tyr Leu Asn
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Human antibody library

<400> SEQUENCE: 28

Ala Ala Ser Ser Leu Gln Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Human antibody library

<400> SEQUENCE: 29

Gln Gln Ser Tyr Ser Thr Pro Arg Thr
1               5

<210> SEQ ID NO 30
<211> LENGTH: 107
<212> TYPE: PRT
<213> ORGANISM: Artificial Sequence
<220> FEATURE:
<223> OTHER INFORMATION: Human antibody library

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly His Gly Thr Lys Val Glu Ile Lys
            100                 105

<210> SEQ ID NO 31
<211> LENGTH: 5
<212> TYPE: PRT
<213> ORGANISM: Artificial Sequence
<220> FEATURE:
<223> OTHER INFORMATION: Human antibody library

<400> SEQUENCE: 31

Met Tyr Trp Met Ala
1               5

<210> SEQ ID NO 32
<211> LENGTH: 7
<212> TYPE: PRT
<213> ORGANISM: Artificial Sequence
<220> FEATURE:
<223> OTHER INFORMATION: Human antibody library

<400> SEQUENCE: 32

Gly Phe Thr Phe Ser Met Tyr
1               5

<210> SEQ ID NO 33
<211> LENGTH: 17
<212> TYPE: PRT
<213> ORGANISM: Artificial Sequence
<220> FEATURE:
<223> OTHER INFORMATION: Human antibody library

<400> SEQUENCE: 33

Tyr Ile Val Pro Ser Gly Gly Ile Thr Leu Tyr Ala Asp Ser Val Lys
1               5                   10                  15

Gly

-continued

```
<210> SEQ ID NO 34
<211> LENGTH: 6
<212> TYPE: PRT
<213> ORGANISM: Artificial Sequence
<220> FEATURE:
<223> OTHER INFORMATION: Human antibody library

<400> SEQUENCE: 34

Val Pro Ser Gly Gly Ile
1               5

<210> SEQ ID NO 35
<211> LENGTH: 9
<212> TYPE: PRT
<213> ORGANISM: Artificial Sequence
<220> FEATURE:
<223> OTHER INFORMATION: Human antibody library

<400> SEQUENCE: 35

Gln Val Arg Gly Gly Ala Phe Asp Ile
1               5

<210> SEQ ID NO 36
<211> LENGTH: 118
<212> TYPE: PRT
<213> ORGANISM: Artificial Sequence
<220> FEATURE:
<223> OTHER INFORMATION: Human antibody library

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Trp Met Ala Trp Val Arg Gln Ala Pro Gly Lys Gly Leu Glu Trp Val
        35                  40                  45

Ser Tyr Ile Val Pro Ser Gly Gly Ile Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Gln Val Arg Gly Gly Ala Phe Asp Ile Trp Gly Gln Gly Thr
            100                 105                 110

Met Val Thr Val Ser Ser
        115

<210> SEQ ID NO 37
<211> LENGTH: 11
<212> TYPE: PRT
<213> ORGANISM: Artificial Sequence
<220> FEATURE:
<223> OTHER INFORMATION: Human antibody library

<400> SEQUENCE: 37

Gln Ala Ser His Asp Ile Ser Asn Tyr Leu Asn
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Human antibody library
```

-continued

<400> SEQUENCE: 38

Asp Ala Ser Asn Leu Glu Thr
1               5

<210> SEQ ID NO 39
<211> LENGTH: 9
<212> TYPE: PRT
<213> ORGANISM: Artificial Sequence
<220> FEATURE:
<223> OTHER INFORMATION: Human antibody library

<400> SEQUENCE: 39

Gln His Tyr Asp Asn Leu Pro Pro Ser
1               5

<210> SEQ ID NO 40
<211> LENGTH: 107
<212> TYPE: PRT
<213> ORGANISM: Artificial Sequence
<220> FEATURE:
<223> OTHER INFORMATION: Human antibody library

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Gln Ala Ser His Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln His Tyr Asp Asn Leu Pro Pro
                85                  90                  95

Ser Phe Gly Gln Gly Thr Lys Leu Glu Ile Lys
            100                 105

<210> SEQ ID NO 41
<211> LENGTH: 5
<212> TYPE: PRT
<213> ORGANISM: Artificial Sequence
<220> FEATURE:
<223> OTHER INFORMATION: from human Fab library

<400> SEQUENCE: 41

His Tyr Pro Met Val
1               5

<210> SEQ ID NO 42
<211> LENGTH: 7
<212> TYPE: PRT
<213> ORGANISM: Artificial Sequence
<220> FEATURE:
<223> OTHER INFORMATION: from human Fab library

<400> SEQUENCE: 42

Gly Phe Thr Phe Ser His Tyr
1               5

<210> SEQ ID NO 43
<211> LENGTH: 17

```
<212> TYPE: PRT
<213> ORGANISM: Artificial Sequence
<220> FEATURE:
<223> OTHER INFORMATION: from human Fab library

<400> SEQUENCE: 43

Trp Ile Gly Ser Ser Gly Gly Phe Thr Met Tyr Ala Asp Ser Val Lys
1               5                   10                  15

Gly

<210> SEQ ID NO 44
<211> LENGTH: 6
<212> TYPE: PRT
<213> ORGANISM: Artificial Sequence
<220> FEATURE:
<223> OTHER INFORMATION: from human Fab library

<400> SEQUENCE: 44

Gly Ser Ser Gly Gly Phe
1               5

<210> SEQ ID NO 45
<211> LENGTH: 11
<212> TYPE: PRT
<213> ORGANISM: Artificial Sequence
<220> FEATURE:
<223> OTHER INFORMATION: Human antibody library

<400> SEQUENCE: 45

Asp Ser Phe Glu Asp His Tyr Tyr Met Asp Val
1               5                   10

<210> SEQ ID NO 46
<211> LENGTH: 120
<212> TYPE: PRT
<213> ORGANISM: Artificial Sequence
<220> FEATURE:
<223> OTHER INFORMATION: Human antibody library

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Pro Met Val Trp Val Arg Gln Ala Pro Gly Lys Gly Leu Glu Trp Val
        35                  40                  45

Ser Trp Ile Gly Ser Ser Gly Gly Phe Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Asp Ser Phe Glu Asp His Tyr Tyr Met Asp Val Trp Gly Lys
                100                 105                 110

Gly Thr Thr Val Thr Val Ser Ser
        115                 120

<210> SEQ ID NO 47
<211> LENGTH: 16
<212> TYPE: PRT
<213> ORGANISM: Artificial Sequence
<220> FEATURE:
<223> OTHER INFORMATION: Human antibody library
```

<400> SEQUENCE: 47

Arg Ser Ser Gln Ser Leu Leu His Ser Asn Gly Tyr Asn Tyr Leu Asp
1               5                   10                  15

<210> SEQ ID NO 48
<211> LENGTH: 7
<212> TYPE: PRT
<213> ORGANISM: Artificial Sequence
<220> FEATURE:
<223> OTHER INFORMATION: Human antibody library

<400> SEQUENCE: 48

Leu Gly Ser Asn Arg Ala Ser
1               5

<210> SEQ ID NO 49
<211> LENGTH: 9
<212> TYPE: PRT
<213> ORGANISM: Artificial Sequence
<220> FEATURE:
<223> OTHER INFORMATION: Human antibody library

<400> SEQUENCE: 49

Met Gln Ala Leu Gln Thr Pro Leu Thr
1               5

<210> SEQ ID NO 50
<211> LENGTH: 112
<212> TYPE: PRT
<213> ORGANISM: Artificial Sequence
<220> FEATURE:
<223> OTHER INFORMATION: Human antibody library

<400> SEQUENCE: 50

Asp Ile Gln Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 51
<211> LENGTH: 5
<212> TYPE: PRT
<213> ORGANISM: Artificial Sequence
<220> FEATURE:
<223> OTHER INFORMATION: Human antibody library

<400> SEQUENCE: 51

Glu Tyr Val Met Ile
1               5

<210> SEQ ID NO 52
<211> LENGTH: 7

```
<212> TYPE: PRT
<213> ORGANISM: Artificial Sequence
<220> FEATURE:
<223> OTHER INFORMATION: Human antibody library

<400> SEQUENCE: 52

Gly Phe Thr Phe Ser Glu Tyr
1               5

<210> SEQ ID NO 53
<211> LENGTH: 17
<212> TYPE: PRT
<213> ORGANISM: Artificial Sequence
<220> FEATURE:
<223> OTHER INFORMATION: Human antibody library

<400> SEQUENCE: 53

Ser Ile Ser Ser Ser Gly Gly Phe Thr Trp Tyr Ala Asp Ser Val Lys
1               5                   10                  15
Gly

<210> SEQ ID NO 54
<211> LENGTH: 6
<212> TYPE: PRT
<213> ORGANISM: Artificial Sequence
<220> FEATURE:
<223> OTHER INFORMATION: Human antibody library

<400> SEQUENCE: 54

Ser Ser Ser Gly Gly Phe
1               5

<210> SEQ ID NO 55
<211> LENGTH: 12
<212> TYPE: PRT
<213> ORGANISM: Artificial Sequence
<220> FEATURE:
<223> OTHER INFORMATION: Human antibody library

<400> SEQUENCE: 55

Ala Arg Ala Pro Val Gly Ala Asp Ala Phe Asp Ile
1               5                   10

<210> SEQ ID NO 56
<211> LENGTH: 121
<212> TYPE: PRT
<213> ORGANISM: Artificial Sequence
<220> FEATURE:
<223> OTHER INFORMATION: Human antibody library

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
                20                  25                  30

Val Met Ile Trp Val Arg Gln Ala Pro Gly Lys Gly Leu Glu Trp Val
            35                  40                  45

Ser Ser Ile Ser Ser Ser Gly Gly Phe Thr Trp Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Ala Arg Ala Pro Val Gly Ala Asp Ala Phe Asp Ile Trp Gly
            100                 105                 110
Gln Gly Thr Met Val Thr Val Ser Ser
        115                 120

<210> SEQ ID NO 57
<211> LENGTH: 11
<212> TYPE: PRT
<213> ORGANISM: Artificial Sequence
<220> FEATURE:
<223> OTHER INFORMATION: Human antibody library

<400> SEQUENCE: 57

Arg Ala Ser Gln Arg Ile Ser Ser Tyr Leu Asn
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Human antibody library

<400> SEQUENCE: 58

Asn Ala Ala Ser Leu Trp Asn
1               5

<210> SEQ ID NO 59
<211> LENGTH: 9
<212> TYPE: PRT
<213> ORGANISM: Artificial Sequence
<220> FEATURE:
<223> OTHER INFORMATION: Human antibody library

<400> SEQUENCE: 59

Gln Gln Ser His Ser Ser Pro Tyr Thr
1               5

<210> SEQ ID NO 60
<211> LENGTH: 107
<212> TYPE: PRT
<213> ORGANISM: Artificial Sequence
<220> FEATURE:
<223> OTHER INFORMATION: Human antibody library

<400> SEQUENCE: 60

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Arg Ile Ser Ser Tyr
            20                  25                  30
Leu Asn Trp Tyr Gln Gln Lys Pro Gly Gln Ala Pro Lys Leu Leu Ile
        35                  40                  45
Asp Asn Ala Ala Ser Leu Trp Asn Gly Val Pro Ser Arg Phe Ser Gly
    50                  55                  60
Ser Gly Ser Gly Thr Asp Phe Thr Leu Thr Ile Thr Thr Leu Met Pro
65                  70                  75                  80
Glu Asp Phe Ala Thr Tyr Phe Cys Gln Gln Ser His Ser Ser Pro Tyr
                85                  90                  95
Thr Phe Gly Gln Gly Thr Lys Leu Glu Ile Arg
            100                 105

<210> SEQ ID NO 61
<211> LENGTH: 5

-continued

```
<212> TYPE: PRT
<213> ORGANISM: Artificial Sequence
<220> FEATURE:
<223> OTHER INFORMATION: from human Fab library

<400> SEQUENCE: 61

Ser Tyr Glu Met His
1               5

<210> SEQ ID NO 62
<211> LENGTH: 7
<212> TYPE: PRT
<213> ORGANISM: Artificial Sequence
<220> FEATURE:
<223> OTHER INFORMATION: from human Fab library

<400> SEQUENCE: 62

Gly Phe Thr Phe Ser Ser Tyr
1               5

<210> SEQ ID NO 63
<211> LENGTH: 17
<212> TYPE: PRT
<213> ORGANISM: Artificial Sequence
<220> FEATURE:
<223> OTHER INFORMATION: from human Fab library

<400> SEQUENCE: 63

Gly Ile Trp Pro Ser Gly Gly Val Thr Leu Tyr Ala Asp Ser Val Lys
1               5                   10                  15

Gly

<210> SEQ ID NO 64
<211> LENGTH: 6
<212> TYPE: PRT
<213> ORGANISM: Artificial Sequence
<220> FEATURE:
<223> OTHER INFORMATION: from human Fab library

<400> SEQUENCE: 64

Trp Pro Ser Gly Gly Val
1               5

<210> SEQ ID NO 65
<211> LENGTH: 8
<212> TYPE: PRT
<213> ORGANISM: Artificial Sequence
<220> FEATURE:
<223> OTHER INFORMATION: Human antibody library

<400> SEQUENCE: 65

Phe Arg Thr Gln Pro Phe Asp Ile
1               5

<210> SEQ ID NO 66
<211> LENGTH: 117
<212> TYPE: PRT
<213> ORGANISM: Artificial Sequence
<220> FEATURE:
<223> OTHER INFORMATION: Human antibody library

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Glu Met His Trp Val Arg Gln Ala Pro Gly Lys Gly Leu Glu Trp Val
        35                  40                  45

Ser Gly Ile Trp Pro Ser Gly Gly Val Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Arg Thr Gln Pro Phe Asp Ile Trp Gly Gln Gly Thr Met
            100                 105                 110

Val Thr Val Ser Ser
        115

<210> SEQ ID NO 67
<211> LENGTH: 11
<212> TYPE: PRT
<213> ORGANISM: Artificial Sequence
<220> FEATURE:
<223> OTHER INFORMATION: Human antibody library

<400> SEQUENCE: 67

Arg Ala Ser Gln Gly Ile Ser Asn Tyr Leu Ala
1               5                   10

<210> SEQ ID NO 68
<211> LENGTH: 7
<212> TYPE: PRT
<213> ORGANISM: Artificial Sequence
<220> FEATURE:
<223> OTHER INFORMATION: Human antibody library

<400> SEQUENCE: 68

Ala Ala Ser Thr Leu Gln Ser
1               5

<210> SEQ ID NO 69
<211> LENGTH: 8
<212> TYPE: PRT
<213> ORGANISM: Artificial Sequence
<220> FEATURE:
<223> OTHER INFORMATION: Human antibody library

<400> SEQUENCE: 69

His Asn Tyr Asn Ser Ala Leu Thr
1               5

<210> SEQ ID NO 70
<211> LENGTH: 106
<212> TYPE: PRT
<213> ORGANISM: Artificial Sequence
<220> FEATURE:
<223> OTHER INFORMATION: Human antibody library

<400> SEQUENCE: 70

Asp Ile Gln Met Thr Gln Ser Pro Asp Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Val Ala Thr Tyr Phe Cys His Asn Tyr Asn Ser Ala Leu Thr
                85                  90                  95

Phe Gly Gly Gly Thr Lys Val Glu Ile Lys
            100                 105

<210> SEQ ID NO 71
<211> LENGTH: 5
<212> TYPE: PRT
<213> ORGANISM: Artificial Sequence
<220> FEATURE:
<223> OTHER INFORMATION: Human antibody library

<400> SEQUENCE: 71

Arg Tyr Gly Met Gly
1               5

<210> SEQ ID NO 72
<211> LENGTH: 7
<212> TYPE: PRT
<213> ORGANISM: Artificial Sequence
<220> FEATURE:
<223> OTHER INFORMATION: Human antibody library

<400> SEQUENCE: 72

Gly Phe Thr Phe Ser Arg Tyr
1               5

<210> SEQ ID NO 73
<211> LENGTH: 17
<212> TYPE: PRT
<213> ORGANISM: Artificial Sequence
<220> FEATURE:
<223> OTHER INFORMATION: Human antibody library

<400> SEQUENCE: 73

Ser Ile Ser Ser Ser Gly Gly Gln Thr Ser Tyr Ala Asp Ser Val Lys
1               5                   10                  15

Gly

<210> SEQ ID NO 74
<211> LENGTH: 6
<212> TYPE: PRT
<213> ORGANISM: Artificial Sequence
<220> FEATURE:
<223> OTHER INFORMATION: Human antibody library

<400> SEQUENCE: 74

Ser Ser Ser Gly Gly Gln
1               5

<210> SEQ ID NO 75
<211> LENGTH: 9
<212> TYPE: PRT
<213> ORGANISM: Artificial Sequence
<220> FEATURE:
<223> OTHER INFORMATION: Human antibody library

<400> SEQUENCE: 75

Gly Gly Leu Trp Phe Gly Leu Asp Pro
1               5

<210> SEQ ID NO 76

```
<211> LENGTH: 118
<212> TYPE: PRT
<213> ORGANISM: Artificial Sequence
<220> FEATURE:
<223> OTHER INFORMATION: Human antibody library

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Gly Trp Val Arg Gln Ala Pro Gly Lys Gly Leu Glu Trp Val
        35                  40                  45

Ser Ser Ile Ser Ser Gly Gly Gln Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Gly Leu Trp Phe Gly Leu Asp Pro Trp Gly Gln Gly Thr
            100                 105                 110

Leu Val Thr Val Ser Ser
        115

<210> SEQ ID NO 77
<211> LENGTH: 11
<212> TYPE: PRT
<213> ORGANISM: Artificial Sequence
<220> FEATURE:
<223> OTHER INFORMATION: Human antibody library

<400> SEQUENCE: 77

Arg Ala Ser Gln Gly Ile Ser Thr Trp Leu Ala
1               5                   10

<210> SEQ ID NO 78
<211> LENGTH: 7
<212> TYPE: PRT
<213> ORGANISM: Artificial Sequence
<220> FEATURE:
<223> OTHER INFORMATION: Human antibody library

<400> SEQUENCE: 78

Ala Ala Ser Ser Leu Gln Ser
1               5

<210> SEQ ID NO 79
<211> LENGTH: 9
<212> TYPE: PRT
<213> ORGANISM: Artificial Sequence
<220> FEATURE:
<223> OTHER INFORMATION: Human antibody library

<400> SEQUENCE: 79

Gln Gln Ala Asn Ser Phe Pro Ser Thr
1               5

<210> SEQ ID NO 80
<211> LENGTH: 107
<212> TYPE: PRT
<213> ORGANISM: Artificial Sequence
<220> FEATURE:
<223> OTHER INFORMATION: Human antibody library
```

<400> SEQUENCE: 80

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Thr Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Ser Ile Ser Ser Leu Gln Pro
65                  70                  75                  80

Glu Asp Phe Ala Thr Tyr Tyr Cys Gln Gln Ala Asn Ser Phe Pro Ser
                85                  90                  95

Thr Phe Gly Gly Gly Thr Lys Val Glu Ile Lys
            100                 105

<210> SEQ ID NO 81
<211> LENGTH: 5
<212> TYPE: PRT
<213> ORGANISM: Artificial Sequence
<220> FEATURE:
<223> OTHER INFORMATION: Human antibody library

<400> SEQUENCE: 81

Lys Tyr Val Met His
1               5

<210> SEQ ID NO 82
<211> LENGTH: 7
<212> TYPE: PRT
<213> ORGANISM: Artificial Sequence
<220> FEATURE:
<223> OTHER INFORMATION: Human antibody library

<400> SEQUENCE: 82

Gly Phe Thr Phe Ser Lys Tyr
1               5

<210> SEQ ID NO 83
<211> LENGTH: 17
<212> TYPE: PRT
<213> ORGANISM: Artificial Sequence
<220> FEATURE:
<223> OTHER INFORMATION: Human antibody library

<400> SEQUENCE: 83

Tyr Ile Ser Ser Ser Gly Gly Phe Thr Val Tyr Ala Asp Ser Val Lys
1               5                   10                  15

Gly

<210> SEQ ID NO 84
<211> LENGTH: 6
<212> TYPE: PRT
<213> ORGANISM: Artificial Sequence
<220> FEATURE:
<223> OTHER INFORMATION: from human Fab library

<400> SEQUENCE: 84

Ser Ser Ser Gly Gly Phe
1               5

<210> SEQ ID NO 85

<211> LENGTH: 10
<212> TYPE: PRT
<213> ORGANISM: Artificial Sequence
<220> FEATURE:
<223> OTHER INFORMATION: Human antibody library

<400> SEQUENCE: 85

Val Phe Asp Ser Gly Asp Ala Phe Asp Ile
1               5                   10

<210> SEQ ID NO 86
<211> LENGTH: 119
<212> TYPE: PRT
<213> ORGANISM: Artificial Sequence
<220> FEATURE:
<223> OTHER INFORMATION: Human antibody library

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Val Met His Trp Val Arg Gln Ala Pro Gly Lys Gly Leu Glu Trp Val
        35                  40                  45

Ser Tyr Ile Ser Ser Gly Gly Phe Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Phe Asp Ser Gly Asp Ala Phe Asp Ile Trp Gly Gln Gly
            100                 105                 110

Thr Met Val Thr Val Ser Ser
        115

<210> SEQ ID NO 87
<211> LENGTH: 17
<212> TYPE: PRT
<213> ORGANISM: Artificial Sequence
<220> FEATURE:
<223> OTHER INFORMATION: Human antibody library

<400> SEQUENCE: 87

Lys Ser Ser Gln Ser Val Leu Tyr Ser Ser Asn Asn Asn Tyr Leu
1               5                   10                  15

Ala

<210> SEQ ID NO 88
<211> LENGTH: 7
<212> TYPE: PRT
<213> ORGANISM: Artificial Sequence
<220> FEATURE:
<223> OTHER INFORMATION: Human antibody library

<400> SEQUENCE: 88

Trp Ala Ser Thr Arg Glu Ser
1               5

<210> SEQ ID NO 89
<211> LENGTH: 9
<212> TYPE: PRT
<213> ORGANISM: Artificial Sequence
<220> FEATURE:

```
<223> OTHER INFORMATION: Human antibody library

<400> SEQUENCE: 89

Gln Gln Tyr Tyr Ser Thr Pro Pro Thr
 1               5

<210> SEQ ID NO 90
<211> LENGTH: 113
<212> TYPE: PRT
<213> ORGANISM: Artificial Sequence
<220> FEATURE:
<223> OTHER INFORMATION: from human Fab library

<400> SEQUENCE: 90

Asp Ile Gln Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gln Gly Thr Lys Val Glu Ile
            100                 105                 110

Lys

<210> SEQ ID NO 91
<211> LENGTH: 5
<212> TYPE: PRT
<213> ORGANISM: Artificial Sequence
<220> FEATURE:
<223> OTHER INFORMATION: from human Fab library

<400> SEQUENCE: 91

Trp Tyr Pro Met His
 1               5

<210> SEQ ID NO 92
<211> LENGTH: 7
<212> TYPE: PRT
<213> ORGANISM: Artificial Sequence
<220> FEATURE:
<223> OTHER INFORMATION: from human Fab library

<400> SEQUENCE: 92

Gly Phe Thr Phe Ser Trp Tyr
 1               5

<210> SEQ ID NO 93
<211> LENGTH: 17
<212> TYPE: PRT
<213> ORGANISM: Artificial Sequence
<220> FEATURE:
<223> OTHER INFORMATION: from human Fab library

<400> SEQUENCE: 93

Ser Ile Ser Ser Ser Gly Gly Phe Thr Met Tyr Ala Asp Ser Val Lys
 1               5                  10                  15
```

Gly

<210> SEQ ID NO 94
<211> LENGTH: 6
<212> TYPE: PRT
<213> ORGANISM: Artificial Sequence
<220> FEATURE:
<223> OTHER INFORMATION: from human Fab library

<400> SEQUENCE: 94

Ser Ser Ser Gly Gly Phe
1               5

<210> SEQ ID NO 95
<211> LENGTH: 11
<212> TYPE: PRT
<213> ORGANISM: Artificial Sequence
<220> FEATURE:
<223> OTHER INFORMATION: from human Fab library

<400> SEQUENCE: 95

Glu Gly Gly Tyr Ser Tyr Gly Pro Gly Asp Tyr
1               5                   10

<210> SEQ ID NO 96
<211> LENGTH: 120
<212> TYPE: PRT
<213> ORGANISM: Artificial Sequence
<220> FEATURE:
<223> OTHER INFORMATION: Human antibody library

<400> SEQUENCE: 96

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Pro Met His Trp Val Arg Gln Ala Pro Gly Lys Gly Leu Glu Trp Val
        35                  40                  45

Ser Ser Ile Ser Ser Ser Gly Gly Phe Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Lys Glu Gly Gly Tyr Ser Tyr Gly Pro Gly Asp Tyr Trp Gly Gln
            100                 105                 110

Gly Thr Leu Val Thr Val Ser Ser
        115                 120

<210> SEQ ID NO 97
<211> LENGTH: 11
<212> TYPE: PRT
<213> ORGANISM: Artificial Sequence
<220> FEATURE:
<223> OTHER INFORMATION: Human antibody library

<400> SEQUENCE: 97

Arg Ala Ser Gln Gly Ile Ser Ser Trp Leu Ala
1               5                   10

<210> SEQ ID NO 98
<211> LENGTH: 7
<212> TYPE: PRT

<213> ORGANISM: Artificial Sequence
<220> FEATURE:
<223> OTHER INFORMATION: Human antibody library

<400> SEQUENCE: 98

Ala Ala Ser Ser Leu Gln Ser
1               5

<210> SEQ ID NO 99
<211> LENGTH: 9
<212> TYPE: PRT
<213> ORGANISM: Artificial Sequence
<220> FEATURE:
<223> OTHER INFORMATION: Human antibody library

<400> SEQUENCE: 99

Gln Gln Ala Asn Ser Phe Pro Tyr Thr
1               5

<210> SEQ ID NO 100
<211> LENGTH: 107
<212> TYPE: PRT
<213> ORGANISM: Artificial Sequence
<220> FEATURE:
<223> OTHER INFORMATION: from human Fab library

<400> SEQUENCE: 100

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu Ile Lys
            100                 105

<210> SEQ ID NO 101
<211> LENGTH: 5
<212> TYPE: PRT
<213> ORGANISM: Artificial Sequence
<220> FEATURE:
<223> OTHER INFORMATION: from human Fab library

<400> SEQUENCE: 101

Trp Tyr Pro Met Thr
1               5

<210> SEQ ID NO 102
<211> LENGTH: 7
<212> TYPE: PRT
<213> ORGANISM: Artificial Sequence
<220> FEATURE:
<223> OTHER INFORMATION: from human Fab library

<400> SEQUENCE: 102

Gly Phe Thr Phe Ser Trp Tyr
1               5

<210> SEQ ID NO 103
<211> LENGTH: 17
<212> TYPE: PRT
<213> ORGANISM: Artificial Sequence
<220> FEATURE:
<223> OTHER INFORMATION: from human Fab library

<400> SEQUENCE: 103

Ser Ile Gly Ser Ser Gly Gly Phe Thr Leu Tyr Ala Asp Ser Val Lys
1               5                   10                  15

Gly

<210> SEQ ID NO 104
<211> LENGTH: 7
<212> TYPE: PRT
<213> ORGANISM: Artificial Sequence
<220> FEATURE:
<223> OTHER INFORMATION: Human antibody library

<400> SEQUENCE: 104

Ile Gly Ser Ser Gly Gly Phe
1               5

<210> SEQ ID NO 105
<211> LENGTH: 12
<212> TYPE: PRT
<213> ORGANISM: Artificial Sequence
<220> FEATURE:
<223> OTHER INFORMATION: Human antibody library

<400> SEQUENCE: 105

Asp Val Trp Gly Ile Ala Ala Pro Tyr Phe Asp Tyr
1               5                   10

<210> SEQ ID NO 106
<211> LENGTH: 121
<212> TYPE: PRT
<213> ORGANISM: Artificial Sequence
<220> FEATURE:
<223> OTHER INFORMATION: Human antibody library

<400> SEQUENCE: 106

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Pro Met Thr Trp Val Arg Gln Ala Pro Gly Lys Gly Leu Glu Trp Val
        35                  40                  45

Ser Ser Ile Gly Ser Ser Gly Gly Phe Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Asp Val Trp Gly Ile Ala Ala Pro Tyr Phe Asp Tyr Trp Gly
            100                 105                 110

Gln Gly Thr Leu Val Thr Val Ser Ser
        115                 120

<210> SEQ ID NO 107
<211> LENGTH: 11
<212> TYPE: PRT

<213> ORGANISM: Artificial Sequence
<220> FEATURE:
<223> OTHER INFORMATION: Human antibody library

<400> SEQUENCE: 107

Arg Ala Ser Gln Gly Ile Gly Ser Trp Leu Gly
1               5                   10

<210> SEQ ID NO 108
<211> LENGTH: 7
<212> TYPE: PRT
<213> ORGANISM: Artificial Sequence
<220> FEATURE:
<223> OTHER INFORMATION: Human antibody library

<400> SEQUENCE: 108

Ala Ala Ser Asn Leu Gln Ser
1               5

<210> SEQ ID NO 109
<211> LENGTH: 9
<212> TYPE: PRT
<213> ORGANISM: Artificial Sequence
<220> FEATURE:
<223> OTHER INFORMATION: Human antibody library

<400> SEQUENCE: 109

Gln Gln Val Asn Asn Phe Pro Arg Ala
1               5

<210> SEQ ID NO 110
<211> LENGTH: 107
<212> TYPE: PRT
<213> ORGANISM: Artificial Sequence
<220> FEATURE:
<223> OTHER INFORMATION: Human antibody library

<400> SEQUENCE: 110

Asp Ile Gln Met Thr Gln Ser Pro Ser Ser Val Ser Ala Ser Val Gly
1               5                   10                  15

Asp Arg Val Thr Ile Ser Cys Arg Ala Ser Gln Gly Ile Gly Ser Trp
            20                  25                  30

Leu Gly Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Val Asn Asn Phe Pro Arg
                85                  90                  95

Ala Phe Gly Gly Gly Thr Lys Val Glu Ile Lys
            100                 105

<210> SEQ ID NO 111
<211> LENGTH: 5
<212> TYPE: PRT
<213> ORGANISM: Artificial Sequence
<220> FEATURE:
<223> OTHER INFORMATION: Human antibody library

<400> SEQUENCE: 111

Trp Tyr Ile Met Ala
1               5

<210> SEQ ID NO 112
<211> LENGTH: 7
<212> TYPE: PRT
<213> ORGANISM: Artificial Sequence
<220> FEATURE:
<223> OTHER INFORMATION: from human Fab library

<400> SEQUENCE: 112

Gly Phe Thr Phe Ser Trp Tyr
1               5

<210> SEQ ID NO 113
<211> LENGTH: 17
<212> TYPE: PRT
<213> ORGANISM: Artificial Sequence
<220> FEATURE:
<223> OTHER INFORMATION: Human antibody library

<400> SEQUENCE: 113

Tyr Ile Ser Ser Ser Gly Gly Phe Thr Ala Tyr Ala Asp Ser Val Lys
1               5                   10                  15

Gly

<210> SEQ ID NO 114
<211> LENGTH: 6
<212> TYPE: PRT
<213> ORGANISM: Artificial Sequence
<220> FEATURE:
<223> OTHER INFORMATION: Human antibody library

<400> SEQUENCE: 114

Ser Ser Ser Gly Gly Phe
1               5

<210> SEQ ID NO 115
<211> LENGTH: 9
<212> TYPE: PRT
<213> ORGANISM: Artificial Sequence
<220> FEATURE:
<223> OTHER INFORMATION: Human antibody library

<400> SEQUENCE: 115

Ile Gly Gly Thr Asp Val Phe Asp Ile
1               5

<210> SEQ ID NO 116
<211> LENGTH: 118
<212> TYPE: PRT
<213> ORGANISM: Artificial Sequence
<220> FEATURE:
<223> OTHER INFORMATION: Human antibody library

<400> SEQUENCE: 116

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
                20                  25                  30

Ile Met Ala Trp Val Arg Gln Ala Pro Gly Lys Gly Leu Glu Trp Val
            35                  40                  45

Ser Tyr Ile Ser Ser Ser Gly Gly Phe Thr Ala Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Ile Gly Gly Thr Asp Val Phe Asp Ile Trp Gly Gln Gly Thr
        100                 105                 110

Leu Val Thr Val Ser Ser
        115

<210> SEQ ID NO 117
<211> LENGTH: 11
<212> TYPE: PRT
<213> ORGANISM: Artificial Sequence
<220> FEATURE:
<223> OTHER INFORMATION: Human antibody library

<400> SEQUENCE: 117

Arg Ala Ser Gln Ser Ile Ser Ser Trp Leu Ala
1               5                   10

<210> SEQ ID NO 118
<211> LENGTH: 7
<212> TYPE: PRT
<213> ORGANISM: Artificial Sequence
<220> FEATURE:
<223> OTHER INFORMATION: Human antibody library

<400> SEQUENCE: 118

Lys Ala Ser Ser Leu Glu Ser
1               5

<210> SEQ ID NO 119
<211> LENGTH: 9
<212> TYPE: PRT
<213> ORGANISM: Artificial Sequence
<220> FEATURE:
<223> OTHER INFORMATION: Human antibody library

<400> SEQUENCE: 119

Gln Gln Ser Tyr Ser Ser Pro Trp Thr
1               5

<210> SEQ ID NO 120
<211> LENGTH: 107
<212> TYPE: PRT
<213> ORGANISM: Artificial Sequence
<220> FEATURE:
<223> OTHER INFORMATION: Human antibody library

<400> SEQUENCE: 120

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Asp Phe Thr Leu Thr Ile Thr Ser Leu Leu Pro
65                  70                  75                  80

Glu Asp Phe Ala Thr Tyr Tyr Cys Gln Gln Ser Tyr Ser Ser Pro Trp
                85                  90                  95

Thr Phe Gly Gln Gly Thr Lys Val Glu Val Lys
            100                 105

```
<210> SEQ ID NO 121
<211> LENGTH: 5
<212> TYPE: PRT
<213> ORGANISM: Artificial Sequence
<220> FEATURE:
<223> OTHER INFORMATION: Human antibody library

<400> SEQUENCE: 121

Trp Tyr Leu Met Lys
1               5

<210> SEQ ID NO 122
<211> LENGTH: 7
<212> TYPE: PRT
<213> ORGANISM: Artificial Sequence
<220> FEATURE:
<223> OTHER INFORMATION: Human antibody library

<400> SEQUENCE: 122

Gly Phe Thr Phe Ser Trp Tyr
1               5

<210> SEQ ID NO 123
<211> LENGTH: 17
<212> TYPE: PRT
<213> ORGANISM: Artificial Sequence
<220> FEATURE:
<223> OTHER INFORMATION: Human antibody library

<400> SEQUENCE: 123

Tyr Ile Gly Ser Ser Gly Gly Phe Thr Ala Tyr Ala Asp Ser Val Lys
1               5                   10                  15

Gly

<210> SEQ ID NO 124
<211> LENGTH: 6
<212> TYPE: PRT
<213> ORGANISM: Artificial Sequence
<220> FEATURE:
<223> OTHER INFORMATION: Human antibody library

<400> SEQUENCE: 124

Gly Ser Ser Gly Gly Phe
1               5

<210> SEQ ID NO 125
<211> LENGTH: 9
<212> TYPE: PRT
<213> ORGANISM: Artificial Sequence
<220> FEATURE:
<223> OTHER INFORMATION: Human antibody library

<400> SEQUENCE: 125

Glu Asp Asp Phe Gly Ala Met Asp Val
1               5

<210> SEQ ID NO 126
<211> LENGTH: 118
<212> TYPE: PRT
<213> ORGANISM: Artificial Sequence
<220> FEATURE:
<223> OTHER INFORMATION: Human antibody library

<400> SEQUENCE: 126

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Trp Tyr
            20                  25                  30

Leu Met Lys Trp Val Arg Gln Ala Pro Gly Lys Gly Leu Glu Trp Val
        35                  40                  45

Ser Tyr Ile Gly Ser Ser Gly Gly Phe Thr Ala Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Met Tyr Tyr Cys
                85                  90                  95

Ala Arg Glu Asp Asp Phe Gly Ala Met Asp Val Trp Gly Gln Gly Thr
            100                 105                 110

Thr Val Thr Val Ser Ser
            115

<210> SEQ ID NO 127
<211> LENGTH: 11
<212> TYPE: PRT
<213> ORGANISM: Artificial Sequence
<220> FEATURE:
<223> OTHER INFORMATION: Human antibody library

<400> SEQUENCE: 127

Arg Ala Ser Gln Thr Val Ser Lys Tyr Phe Asn
1               5                   10

<210> SEQ ID NO 128
<211> LENGTH: 7
<212> TYPE: PRT
<213> ORGANISM: Artificial Sequence
<220> FEATURE:
<223> OTHER INFORMATION: Human antibody library

<400> SEQUENCE: 128

Ala Thr Ser Thr Leu Gln Ser
1               5

<210> SEQ ID NO 129
<211> LENGTH: 9
<212> TYPE: PRT
<213> ORGANISM: Artificial Sequence
<220> FEATURE:
<223> OTHER INFORMATION: Human antibody library

<400> SEQUENCE: 129

Gln Gln Ser Tyr Thr Thr Pro Trp Thr
1               5

<210> SEQ ID NO 130
<211> LENGTH: 107
<212> TYPE: PRT
<213> ORGANISM: Artificial Sequence
<220> FEATURE:
<223> OTHER INFORMATION: Human antibody library

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Val Ser Lys Tyr
            20                  25                  30

Phe Asn Trp Phe Gln Gln Lys Pro Gly Glu Ala Pro Lys Leu Leu Ile
        35                  40                  45
```

Tyr Ala Thr Ser Thr Leu Gln Ser Gly Val Pro Ser Arg Phe Ser Gly
            50                  55                  60

Ser Gly Tyr Gly Thr Glu Phe Thr Leu Thr Ile Ser Ser Leu Gln Pro
 65                  70                  75                  80

Glu Asp Phe Ala Thr Tyr Tyr Cys Gln Gln Ser Tyr Thr Thr Pro Trp
                 85                  90                  95

Thr Phe Gly Gln Gly Thr Lys Val Glu Ile Lys
            100                 105

<210> SEQ ID NO 131
<211> LENGTH: 5
<212> TYPE: PRT
<213> ORGANISM: Artificial Sequence
<220> FEATURE:
<223> OTHER INFORMATION: Human antibody library

<400> SEQUENCE: 131

Ser Tyr Gln Met Gly
1               5

<210> SEQ ID NO 132
<211> LENGTH: 7
<212> TYPE: PRT
<213> ORGANISM: Artificial Sequence
<220> FEATURE:
<223> OTHER INFORMATION: Human antibody library

<400> SEQUENCE: 132

Gly Phe Thr Phe Ser Ser Tyr
1               5

<210> SEQ ID NO 133
<211> LENGTH: 17
<212> TYPE: PRT
<213> ORGANISM: Artificial Sequence
<220> FEATURE:
<223> OTHER INFORMATION: Human antibody library

<400> SEQUENCE: 133

Trp Ile Val Pro Ser Gly Gly Phe Thr His Tyr Ala Asp Ser Val Lys
1               5                   10                  15

Gly

<210> SEQ ID NO 134
<211> LENGTH: 6
<212> TYPE: PRT
<213> ORGANISM: Artificial Sequence
<220> FEATURE:
<223> OTHER INFORMATION: Human antibody library

<400> SEQUENCE: 134

Val Pro Ser Gly Gly Phe
1               5

<210> SEQ ID NO 135
<211> LENGTH: 16
<212> TYPE: PRT
<213> ORGANISM: Artificial Sequence
<220> FEATURE:
<223> OTHER INFORMATION: Human antibody library

<400> SEQUENCE: 135

Asp Ala Gly Tyr Arg Ser Gly Tyr Tyr Tyr Tyr Gly Met Asp Val
1               5                   10                  15

<210> SEQ ID NO 136
<211> LENGTH: 125
<212> TYPE: PRT
<213> ORGANISM: Artificial Sequence
<220> FEATURE:
<223> OTHER INFORMATION: Human antibody library

<400> SEQUENCE: 136

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Gly Trp Val Arg Gln Ala Pro Gly Lys Gly Leu Glu Trp Val
        35                  40                  45

Ser Trp Ile Val Pro Ser Gly Gly Phe Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gly Tyr Arg Ser Gly Tyr Tyr Tyr Tyr Gly Met
            100                 105                 110

Asp Val Trp Gly Gln Gly Thr Thr Val Thr Val Ser Ser
        115                 120                 125

<210> SEQ ID NO 137
<211> LENGTH: 11
<212> TYPE: PRT
<213> ORGANISM: Artificial Sequence
<220> FEATURE:
<223> OTHER INFORMATION: Human antibody library

<400> SEQUENCE: 137

Arg Ala Ser Gln Ser Ile Ala Ser Tyr Leu Asn
1               5                   10

<210> SEQ ID NO 138
<211> LENGTH: 7
<212> TYPE: PRT
<213> ORGANISM: Artificial Sequence
<220> FEATURE:
<223> OTHER INFORMATION: Human antibody library

<400> SEQUENCE: 138

Gly Ala Ser Ser Leu Gln Ser
1               5

<210> SEQ ID NO 139
<211> LENGTH: 9
<212> TYPE: PRT
<213> ORGANISM: Artificial Sequence
<220> FEATURE:
<223> OTHER INFORMATION: Human antibody library

<400> SEQUENCE: 139

Gln Gln Ser Tyr Gly Ile Ser Tyr Thr
1               5

<210> SEQ ID NO 140
<211> LENGTH: 107
<212> TYPE: PRT
<213> ORGANISM: Artificial Sequence
<220> FEATURE:
<223> OTHER INFORMATION: Human antibody library

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Arg Ser Leu Gln Pro
65                  70                  75                  80

Glu Asp Ile Ala Thr Tyr Tyr Cys Gln Gln Ser Tyr Gly Ile Ser Tyr
                85                  90                  95

Thr Phe Gly Gln Gly Thr Lys Leu Glu Ile Lys
            100                 105

<210> SEQ ID NO 141
<211> LENGTH: 5
<212> TYPE: PRT
<213> ORGANISM: Artificial Sequence
<220> FEATURE:
<223> OTHER INFORMATION: Human antibody library

<400> SEQUENCE: 141

His Tyr Pro Met Ser
1               5

<210> SEQ ID NO 142
<211> LENGTH: 7
<212> TYPE: PRT
<213> ORGANISM: Artificial Sequence
<220> FEATURE:
<223> OTHER INFORMATION: Human antibody library

<400> SEQUENCE: 142

Gly Phe Thr Phe Ser His Tyr
1               5

<210> SEQ ID NO 143
<211> LENGTH: 17
<212> TYPE: PRT
<213> ORGANISM: Artificial Sequence
<220> FEATURE:
<223> OTHER INFORMATION: Human antibody library

<400> SEQUENCE: 143

Arg Ile Trp Ser Ser Gly Gly Asn Thr Tyr Tyr Ala Asp Ser Val Lys
1               5                   10                  15

Gly

<210> SEQ ID NO 144
<211> LENGTH: 7
<212> TYPE: PRT
<213> ORGANISM: Artificial Sequence
<220> FEATURE:
<223> OTHER INFORMATION: Human antibody library

<400> SEQUENCE: 144

Ile Trp Ser Ser Gly Gly Asn
1               5

<210> SEQ ID NO 145
<211> LENGTH: 12
<212> TYPE: PRT
<213> ORGANISM: Artificial Sequence
<220> FEATURE:
<223> OTHER INFORMATION: from human antibody library

<400> SEQUENCE: 145

```
Gly Gly Tyr Phe Asp Trp Leu Tyr Pro His Asp Tyr
1               5                   10
```

<210> SEQ ID NO 146
<211> LENGTH: 121
<212> TYPE: PRT
<213> ORGANISM: Artificial Sequence
<220> FEATURE:
<223> OTHER INFORMATION: from human antibody library

<400> SEQUENCE: 146

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Pro Met Ser Trp Val Arg Gln Ala Pro Gly Lys Gly Leu Glu Trp Val
        35                  40                  45

Ser Arg Ile Trp Ser Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Phe Asp Trp Leu Tyr Pro His Asp Tyr Trp Gly
            100                 105                 110

Gln Gly Thr Leu Val Thr Val Ser Ser
        115                 120
```

<210> SEQ ID NO 147
<211> LENGTH: 11
<212> TYPE: PRT
<213> ORGANISM: Artificial Sequence
<220> FEATURE:
<223> OTHER INFORMATION: from human antibody library

<400> SEQUENCE: 147

```
Arg Ala Ser Gln Gly Ile Ser Ser Trp Leu Ser
1               5                   10
```

<210> SEQ ID NO 148
<211> LENGTH: 7
<212> TYPE: PRT
<213> ORGANISM: Artificial Sequence
<220> FEATURE:
<223> OTHER INFORMATION: from human antibody library

<400> SEQUENCE: 148

```
Ala Ala Ser Ser Leu Gln Ser
1               5
```

<210> SEQ ID NO 149
<211> LENGTH: 9
<212> TYPE: PRT
<213> ORGANISM: Artificial Sequence
<220> FEATURE:
<223> OTHER INFORMATION: Human antibody library

<400> SEQUENCE: 149

Gln Gln Gly Asn Ser Phe Pro Pro Thr
1               5

<210> SEQ ID NO 150
<211> LENGTH: 107
<212> TYPE: PRT
<213> ORGANISM: Artificial Sequence
<220> FEATURE:
<223> OTHER INFORMATION: Human antibody library

<400> SEQUENCE: 150

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ser Trp Tyr Gln Gln Lys Pro Gly Ala Ala Pro Lys Leu Leu Ile
            35                  40                  45

Tyr Ala Ala Ser Ser Leu Gln Ser Gly Val Pro Ala Arg Phe Ser Gly
    50                  55                  60

Ser Gly Ser Gly Arg Glu Phe Thr Leu Thr Ile Ser Asn Leu Gln Pro
65                  70                  75                  80

Glu Asp Phe Ala Thr Tyr Tyr Cys Gln Gln Gly Asn Ser Phe Pro Pro
                85                  90                  95

Thr Phe Gly Gln Gly Thr Lys Val Asp Ile Lys
            100                 105

<210> SEQ ID NO 151
<211> LENGTH: 5
<212> TYPE: PRT
<213> ORGANISM: Artificial Sequence
<220> FEATURE:
<223> OTHER INFORMATION: Human antibody library

<400> SEQUENCE: 151

Arg Tyr Glu Met Leu
1               5

<210> SEQ ID NO 152
<211> LENGTH: 7
<212> TYPE: PRT
<213> ORGANISM: Artificial Sequence
<220> FEATURE:
<223> OTHER INFORMATION: Human antibody library

<400> SEQUENCE: 152

Gly Phe Thr Phe Ser Arg Tyr
1               5

<210> SEQ ID NO 153
<211> LENGTH: 17
<212> TYPE: PRT
<213> ORGANISM: Artificial Sequence
<220> FEATURE:
<223> OTHER INFORMATION: Human antibody library

<400> SEQUENCE: 153

Ser Ile Tyr Ser Ser Gly Gly Trp Thr Trp Tyr Ala Asp Ser Val Lys
1               5                   10                  15

Gly

<210> SEQ ID NO 154
<211> LENGTH: 6
<212> TYPE: PRT
<213> ORGANISM: Artificial Sequence
<220> FEATURE:
<223> OTHER INFORMATION: Human antibody library

<400> SEQUENCE: 154

Tyr Ser Ser Gly Gly Trp
1               5

<210> SEQ ID NO 155
<211> LENGTH: 10
<212> TYPE: PRT
<213> ORGANISM: Artificial Sequence
<220> FEATURE:
<223> OTHER INFORMATION: Human antibody library

<400> SEQUENCE: 155

His Ser Val Thr Gly Val Ala Phe Asp Tyr
1               5                   10

<210> SEQ ID NO 156
<211> LENGTH: 119
<212> TYPE: PRT
<213> ORGANISM: Artificial Sequence
<220> FEATURE:
<223> OTHER INFORMATION: Human antibody library

<400> SEQUENCE: 156

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Glu Met Leu Trp Val Arg Gln Ala Pro Gly Lys Gly Leu Glu Trp Val
        35                  40                  45

Ser Ser Ile Tyr Ser Ser Gly Gly Trp Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg His Ser Val Thr Gly Val Ala Phe Asp Tyr Trp Gly Gln Gly
            100                 105                 110

Thr Leu Val Thr Val Ser Ser
        115

<210> SEQ ID NO 157
<211> LENGTH: 11
<212> TYPE: PRT
<213> ORGANISM: Artificial Sequence
<220> FEATURE:
<223> OTHER INFORMATION: Human antibody library

<400> SEQUENCE: 157

Arg Ala Ser Gln Asn Ile Asp Thr Tyr Leu Ser
1               5                   10

<210> SEQ ID NO 158
<211> LENGTH: 7
<212> TYPE: PRT
<213> ORGANISM: Artificial Sequence

```
<220> FEATURE:
<223> OTHER INFORMATION: Human antibody library

<400> SEQUENCE: 158

Ala Ala Ser Ser Leu Gln Ser
1               5

<210> SEQ ID NO 159
<211> LENGTH: 8
<212> TYPE: PRT
<213> ORGANISM: Artificial Sequence
<220> FEATURE:
<223> OTHER INFORMATION: Human antibody library

<400> SEQUENCE: 159

Gln Gln Ser Tyr Tyr Thr Pro Thr
1               5

<210> SEQ ID NO 160
<211> LENGTH: 106
<212> TYPE: PRT
<213> ORGANISM: Artificial Sequence
<220> FEATURE:
<223> OTHER INFORMATION: Human antibody library

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asp Thr Tyr
            20                  25                  30

Leu Ser Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Tyr Thr Pro Thr
                85                  90                  95

Phe Gly Gly Gly Thr Lys Val Glu Ile Lys
            100                 105

<210> SEQ ID NO 161
<211> LENGTH: 5
<212> TYPE: PRT
<213> ORGANISM: Artificial Sequence
<220> FEATURE:
<223> OTHER INFORMATION: from human antibody library

<400> SEQUENCE: 161

Pro Tyr Asp Met Gly
1               5

<210> SEQ ID NO 162
<211> LENGTH: 7
<212> TYPE: PRT
<213> ORGANISM: Artificial Sequence
<220> FEATURE:
<223> OTHER INFORMATION: Human antibody library

<400> SEQUENCE: 162

Gly Phe Thr Phe Ser Pro Tyr
1               5
```

<210> SEQ ID NO 163
<211> LENGTH: 17
<212> TYPE: PRT
<213> ORGANISM: Artificial Sequence
<220> FEATURE:
<223> OTHER INFORMATION: Human antibody library

<400> SEQUENCE: 163

Ser Ile Tyr Ser Ser Gly Gly Trp Thr Lys Tyr Ala Asp Ser Val Lys
1               5                   10                  15
Gly

<210> SEQ ID NO 164
<211> LENGTH: 6
<212> TYPE: PRT
<213> ORGANISM: Artificial Sequence
<220> FEATURE:
<223> OTHER INFORMATION: Human antibody library

<400> SEQUENCE: 164

Tyr Ser Ser Gly Gly Trp
1               5

<210> SEQ ID NO 165
<211> LENGTH: 10
<212> TYPE: PRT
<213> ORGANISM: Artificial Sequence
<220> FEATURE:
<223> OTHER INFORMATION: Human antibody library

<400> SEQUENCE: 165

Asp Asn Trp Asn Asp Gly Ala Phe Asp Val
1               5                   10

<210> SEQ ID NO 166
<211> LENGTH: 119
<212> TYPE: PRT
<213> ORGANISM: Artificial Sequence
<220> FEATURE:
<223> OTHER INFORMATION: Human antibody library

<400> SEQUENCE: 166

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Asp Met Gly Trp Val Arg Gln Ala Pro Gly Lys Gly Leu Glu Trp Val
        35                  40                  45

Ser Ser Ile Tyr Ser Ser Gly Gly Trp Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Trp Asn Asp Gly Ala Phe Asp Val Trp Gly Gln Gly
            100                 105                 110

Thr Met Val Thr Val Ser Ser
        115

<210> SEQ ID NO 167
<211> LENGTH: 11
<212> TYPE: PRT
<213> ORGANISM: Artificial Sequence

```
<220> FEATURE:
<223> OTHER INFORMATION: Human antibody library

<400> SEQUENCE: 167

Arg Ala Ser Gln Ser Ile Ser Ser Trp Leu Ala
1               5                   10

<210> SEQ ID NO 168
<211> LENGTH: 7
<212> TYPE: PRT
<213> ORGANISM: Artificial Sequence
<220> FEATURE:
<223> OTHER INFORMATION: Human antibody library

<400> SEQUENCE: 168

Ala Ala Ser Arg Leu Gln Thr
1               5

<210> SEQ ID NO 169
<211> LENGTH: 9
<212> TYPE: PRT
<213> ORGANISM: Artificial Sequence
<220> FEATURE:
<223> OTHER INFORMATION: Human antibody library

<400> SEQUENCE: 169

Gln Gln Ala Lys Thr Phe Pro Leu Thr
1               5

<210> SEQ ID NO 170
<211> LENGTH: 107
<212> TYPE: PRT
<213> ORGANISM: Artificial Sequence
<220> FEATURE:
<223> OTHER INFORMATION: Human antibody library

<400> SEQUENCE: 170

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Phe Ala Ala Ser Arg Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ala Lys Thr Phe Pro Leu
                85                  90                  95

Thr Phe Gly Gly Gly Thr Arg Val Glu Ile Lys
            100                 105

<210> SEQ ID NO 171
<211> LENGTH: 5
<212> TYPE: PRT
<213> ORGANISM: Artificial Sequence
<220> FEATURE:
<223> OTHER INFORMATION: Human antibody library

<400> SEQUENCE: 171

Phe Tyr Asp Met Ser
1               5
```

```
<210> SEQ ID NO 172
<211> LENGTH: 7
<212> TYPE: PRT
<213> ORGANISM: Artificial Sequence
<220> FEATURE:
<223> OTHER INFORMATION: Human antibody library

<400> SEQUENCE: 172

Gly Phe Thr Phe Ser Phe Tyr
1               5

<210> SEQ ID NO 173
<211> LENGTH: 17
<212> TYPE: PRT
<213> ORGANISM: Artificial Sequence
<220> FEATURE:
<223> OTHER INFORMATION: Human antibody library

<400> SEQUENCE: 173

Ser Ile Val Pro Ser Gly Gly Trp Thr Phe Tyr Ala Asp Ser Val Lys
1               5                   10                  15

Gly

<210> SEQ ID NO 174
<211> LENGTH: 6
<212> TYPE: PRT
<213> ORGANISM: Artificial Sequence
<220> FEATURE:
<223> OTHER INFORMATION: Human antibody library

<400> SEQUENCE: 174

Val Pro Ser Gly Gly Trp
1               5

<210> SEQ ID NO 175
<211> LENGTH: 10
<212> TYPE: PRT
<213> ORGANISM: Artificial Sequence
<220> FEATURE:
<223> OTHER INFORMATION: Human antibody library

<400> SEQUENCE: 175

Asp Ser Trp Asn Asp Gly Ala Ser Asp Ile
1               5                   10

<210> SEQ ID NO 176
<211> LENGTH: 119
<212> TYPE: PRT
<213> ORGANISM: Artificial Sequence
<220> FEATURE:
<223> OTHER INFORMATION: Human antibody library

<400> SEQUENCE: 176

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Asp Met Ser Trp Val Arg Gln Ala Pro Gly Lys Gly Leu Glu Trp Val
        35                  40                  45

Ser Ser Ile Val Pro Ser Gly Gly Trp Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                        85                  90                  95
Ala Arg Asp Ser Trp Asn Asp Gly Ala Ser Asp Ile Trp Gly Gln Gly
            100                 105                 110

Thr Met Val Thr Val Ser Ser
        115

<210> SEQ ID NO 177
<211> LENGTH: 11
<212> TYPE: PRT
<213> ORGANISM: Artificial Sequence
<220> FEATURE:
<223> OTHER INFORMATION: from human antibody library

<400> SEQUENCE: 177

Arg Ala Ser Gln Gly Ile Ser Ser Trp Leu Ala
1               5                   10

<210> SEQ ID NO 178
<211> LENGTH: 7
<212> TYPE: PRT
<213> ORGANISM: Artificial Sequence
<220> FEATURE:
<223> OTHER INFORMATION: from human antibody library

<400> SEQUENCE: 178

Ala Ala Ser Ser Leu Gln Ser
1               5

<210> SEQ ID NO 179
<211> LENGTH: 9
<212> TYPE: PRT
<213> ORGANISM: Artificial Sequence
<220> FEATURE:
<223> OTHER INFORMATION: from human antibody library

<400> SEQUENCE: 179

Gln Gln Ala Asn Ser Phe Pro Phe Thr
1               5

<210> SEQ ID NO 180
<211> LENGTH: 107
<212> TYPE: PRT
<213> ORGANISM: Artificial Sequence
<220> FEATURE:
<223> OTHER INFORMATION: from human antibody library

<400> SEQUENCE: 180

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Phe Lys
            100                 105
```

```
<210> SEQ ID NO 181
<211> LENGTH: 5
<212> TYPE: PRT
<213> ORGANISM: Artificial Sequence
<220> FEATURE:
<223> OTHER INFORMATION: Human antibody library

<400> SEQUENCE: 181

Pro Tyr Gly Met Arg
1               5

<210> SEQ ID NO 182
<211> LENGTH: 7
<212> TYPE: PRT
<213> ORGANISM: Artificial Sequence
<220> FEATURE:
<223> OTHER INFORMATION: Human antibody library

<400> SEQUENCE: 182

Gly Phe Thr Phe Ser Pro Tyr
1               5

<210> SEQ ID NO 183
<211> LENGTH: 17
<212> TYPE: PRT
<213> ORGANISM: Artificial Sequence
<220> FEATURE:
<223> OTHER INFORMATION: Human antibody library

<400> SEQUENCE: 183

Ser Ile Ser Pro Ser Gly Gly Asn Thr Asp Tyr Ala Asp Ser Val Lys
1               5                   10                  15

Gly

<210> SEQ ID NO 184
<211> LENGTH: 6
<212> TYPE: PRT
<213> ORGANISM: Artificial Sequence
<220> FEATURE:
<223> OTHER INFORMATION: Human antibody library

<400> SEQUENCE: 184

Ser Pro Ser Gly Gly Asn
1               5

<210> SEQ ID NO 185
<211> LENGTH: 12
<212> TYPE: PRT
<213> ORGANISM: Artificial Sequence
<220> FEATURE:
<223> OTHER INFORMATION: Human antibody library

<400> SEQUENCE: 185

Arg Ala Ser His Ser Val Ser Ser Asp Tyr Leu Ala
1               5                   10

<210> SEQ ID NO 186
<211> LENGTH: 16
<212> TYPE: PRT
<213> ORGANISM: Artificial Sequence
<220> FEATURE:
<223> OTHER INFORMATION: Human antibody library

<400> SEQUENCE: 186

Ile Arg Tyr Cys Gly Ser Ala Tyr Cys Tyr Thr Asp Ala Phe Asp Ile
1               5                   10                  15
```

```
<210> SEQ ID NO 187
<211> LENGTH: 11
<212> TYPE: PRT
<213> ORGANISM: Artificial Sequence
<220> FEATURE:
<223> OTHER INFORMATION: Human antibody library

<400> SEQUENCE: 187

Ser Gly Glu Lys Leu Gly Asp Arg Tyr Val Ser
1               5                   10

<210> SEQ ID NO 188
<211> LENGTH: 7
<212> TYPE: PRT
<213> ORGANISM: Artificial Sequence
<220> FEATURE:
<223> OTHER INFORMATION: from human Fab library

<400> SEQUENCE: 188

His Asp Lys Lys Arg Pro Pro
1               5

<210> SEQ ID NO 189
<211> LENGTH: 9
<212> TYPE: PRT
<213> ORGANISM: Artificial Sequence
<220> FEATURE:
<223> OTHER INFORMATION: from human antibody library

<400> SEQUENCE: 189

Gln Ala Trp Asp Ser Pro Thr Glu Val
1               5

<210> SEQ ID NO 190
<211> LENGTH: 109
<212> TYPE: PRT
<213> ORGANISM: Artificial Sequence
<220> FEATURE:
<223> OTHER INFORMATION: from human antibody library

<400> SEQUENCE: 190

Gln Ser Ala Leu Thr Gln Ala Pro Ser Val Ser Val Ser Pro Gly Gln
1               5                   10                  15

Thr Thr Thr Ile Thr Cys Ser Gly Glu Lys Leu Gly Asp Arg Tyr Val
            20                  25                  30

Ser Trp Tyr Gln Gln Lys Pro Asp Gln Ser Pro Ile Leu Val Leu Tyr
        35                  40                  45

His Asp Lys Lys Arg Pro Pro Gly Ile Pro Glu Arg Phe Ser Gly Ser
    50                  55                  60

Asn Ser Gly Asp Thr Ala Thr Leu Thr Ile Thr Gly Thr His Thr Met
65                  70                  75                  80

Asp Glu Ala Asp Tyr Tyr Cys Gln Ala Trp Asp Ser Pro Thr Glu Val
                85                  90                  95

Phe Gly Pro Gly Thr Lys Leu Thr Val Leu Ser Gln Pro
            100                 105

<210> SEQ ID NO 191
<211> LENGTH: 5
<212> TYPE: PRT
<213> ORGANISM: Artificial Sequence
<220> FEATURE:
<223> OTHER INFORMATION: from human antibody library

<400> SEQUENCE: 191
```

Met Tyr Asp Met Ala
1               5

<210> SEQ ID NO 192
<211> LENGTH: 7
<212> TYPE: PRT
<213> ORGANISM: Artificial Sequence
<220> FEATURE:
<223> OTHER INFORMATION: from human antibody library

<400> SEQUENCE: 192

Gly Phe Thr Phe Ser Met Tyr
1               5

<210> SEQ ID NO 193
<211> LENGTH: 17
<212> TYPE: PRT
<213> ORGANISM: Artificial Sequence
<220> FEATURE:
<223> OTHER INFORMATION: Human antibody library

<400> SEQUENCE: 193

Gly Ile Trp Pro Ser Gly Gly Pro Thr Met Tyr Ala Asp Ser Val Lys
1               5                   10                  15

Gly

<210> SEQ ID NO 194
<211> LENGTH: 6
<212> TYPE: PRT
<213> ORGANISM: Artificial Sequence
<220> FEATURE:
<223> OTHER INFORMATION: Human antibody library

<400> SEQUENCE: 194

Trp Pro Ser Gly Gly Pro
1               5

<210> SEQ ID NO 195
<211> LENGTH: 10
<212> TYPE: PRT
<213> ORGANISM: Artificial Sequence
<220> FEATURE:
<223> OTHER INFORMATION: Human antibody library

<400> SEQUENCE: 195

Gly Tyr Ser Tyr Gly Asp Ala Leu Asp Tyr
1               5                   10

<210> SEQ ID NO 196
<211> LENGTH: 119
<212> TYPE: PRT
<213> ORGANISM: Artificial Sequence
<220> FEATURE:
<223> OTHER INFORMATION: Human antibody library

<400> SEQUENCE: 196

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Asp Met Ala Trp Val Arg Gln Ala Pro Gly Lys Gly Leu Glu Trp Val
        35                  40                  45

Ser Gly Ile Trp Pro Ser Gly Gly Pro Thr Met Tyr Ala Asp Ser Val
    50                  55                  60

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Tyr Ser Tyr Gly Asp Ala Leu Asp Tyr Trp Gly Gln Gly
            100                 105                 110

Thr Leu Val Thr Val Ser Ser
        115

<210> SEQ ID NO 197
<211> LENGTH: 13
<212> TYPE: PRT
<213> ORGANISM: Artificial Sequence
<220> FEATURE:
<223> OTHER INFORMATION: Human antibody library

<400> SEQUENCE: 197

Ser Gly Thr Ser Ser Asn Ile Gly Arg Asn Tyr Val Ser
1               5                   10

<210> SEQ ID NO 198
<211> LENGTH: 7
<212> TYPE: PRT
<213> ORGANISM: Artificial Sequence
<220> FEATURE:
<223> OTHER INFORMATION: Human antibody library

<400> SEQUENCE: 198

Asp Asp Arg Asn Arg Pro Ser
1               5

<210> SEQ ID NO 199
<211> LENGTH: 11
<212> TYPE: PRT
<213> ORGANISM: Artificial Sequence
<220> FEATURE:
<223> OTHER INFORMATION: Human antibody library

<400> SEQUENCE: 199

Gly Thr Trp Asp Thr Ser Leu Ser Val Val Val
1               5                   10

<210> SEQ ID NO 200
<211> LENGTH: 113
<212> TYPE: PRT
<213> ORGANISM: Artificial Sequence
<220> FEATURE:
<223> OTHER INFORMATION: Human antibody library

<400> SEQUENCE: 200

Gln Ser Ala Leu Thr Gln Pro Pro Ser Ala Ser Gly Ser Pro Gly Gln
1               5                   10                  15

Ser Val Thr Ile Ser Cys Ser Gly Thr Ser Ser Asn Ile Gly Arg Asn
                20                  25                  30

Tyr Val Ser Trp Tyr Arg His Leu Pro Gly Thr Ala Pro Lys Leu Leu
            35                  40                  45

Ile Tyr Asp Asp Arg Asn Arg Pro Ser Gly Ile Val Ala Arg Phe Ser
        50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Thr Ser Leu
                85                  90                  95
```

Ser Val Val Val Phe Gly Gly Gly Thr Lys Val Thr Val Leu Ser Gln
            100                 105                 110
Pro

<210> SEQ ID NO 201
<211> LENGTH: 5
<212> TYPE: PRT
<213> ORGANISM: Artificial Sequence
<220> FEATURE:
<223> OTHER INFORMATION: Human antibody library

<400> SEQUENCE: 201

Glu Tyr Arg Met Ile
1               5

<210> SEQ ID NO 202
<211> LENGTH: 7
<212> TYPE: PRT
<213> ORGANISM: Artificial Sequence
<220> FEATURE:
<223> OTHER INFORMATION: Human antibody library

<400> SEQUENCE: 202

Gly Phe Thr Phe Ser Glu Tyr
1               5

<210> SEQ ID NO 203
<211> LENGTH: 17
<212> TYPE: PRT
<213> ORGANISM: Artificial Sequence
<220> FEATURE:
<223> OTHER INFORMATION: Human antibody library

<400> SEQUENCE: 203

Gly Ile Tyr Pro Ser Gly Gly Trp Thr Asn Tyr Ala Asp Ser Val Lys
1               5                   10                  15
Gly

<210> SEQ ID NO 204
<211> LENGTH: 6
<212> TYPE: PRT
<213> ORGANISM: Artificial Sequence
<220> FEATURE:
<223> OTHER INFORMATION: Human antibody library

<400> SEQUENCE: 204

Tyr Pro Ser Gly Gly Trp
1               5

<210> SEQ ID NO 205
<211> LENGTH: 9
<212> TYPE: PRT
<213> ORGANISM: Artificial Sequence
<220> FEATURE:
<223> OTHER INFORMATION: Human antibody library

<400> SEQUENCE: 205

Ile Gly Gly Ala Asn Ala Phe Asp Ile
1               5

<210> SEQ ID NO 206
<211> LENGTH: 118
<212> TYPE: PRT
<213> ORGANISM: Artificial Sequence
<220> FEATURE:

<223> OTHER INFORMATION: Human antibody library

<400> SEQUENCE: 206

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Arg Met Ile Trp Val Arg Gln Ala Pro Gly Lys Gly Leu Glu Trp Val
        35                  40                  45

Ser Gly Ile Tyr Pro Ser Gly Gly Trp Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Gly Gly Ala Asn Ala Phe Asp Ile Trp Gly Gln Gly Thr
            100                 105                 110

Met Val Thr Val Ser Ser
        115

<210> SEQ ID NO 207
<211> LENGTH: 14
<212> TYPE: PRT
<213> ORGANISM: Artificial Sequence
<220> FEATURE:
<223> OTHER INFORMATION: Human antibody library

<400> SEQUENCE: 207

Thr Gly Thr Ser Ser Asp Ile Gly Gly Tyr Asn Tyr Val Ser
1               5                   10

<210> SEQ ID NO 208
<211> LENGTH: 7
<212> TYPE: PRT
<213> ORGANISM: Artificial Sequence
<220> FEATURE:
<223> OTHER INFORMATION: Human antibody library

<400> SEQUENCE: 208

Glu Val Ser Asn Arg Pro Ser
1               5

<210> SEQ ID NO 209
<211> LENGTH: 11
<212> TYPE: PRT
<213> ORGANISM: Artificial Sequence
<220> FEATURE:
<223> OTHER INFORMATION: Human antibody library

<400> SEQUENCE: 209

Ser Ser Tyr Thr Ser Gly Ser Thr Arg Tyr Val
1               5                   10

<210> SEQ ID NO 210
<211> LENGTH: 114
<212> TYPE: PRT
<213> ORGANISM: Artificial Sequence
<220> FEATURE:
<223> OTHER INFORMATION: Human antibody library

<400> SEQUENCE: 210

Gln Ser Ala Leu Thr Gln Pro Ala Ser Val Ser Gly Ser Pro Gly Gln
1               5                   10                  15

```
Ser Ile Thr Ile Ser Cys Thr Gly Thr Ser Ser Asp Ile Gly Gly Tyr
                 20                  25                  30

Asn Tyr Val Ser Trp Tyr Gln Gln His Pro Gly Lys Ala Pro Lys Leu
             35                  40                  45

Met Ile Tyr Glu Val Ser Asn Arg Pro Ser Gly Val Ser Asn Arg Phe
         50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Gly
                 85                  90                  95

Ser Thr Arg Tyr Val Phe Gly Pro Gly Thr Lys Val Thr Val Leu Gly
                100                 105                 110

Gln Pro

<210> SEQ ID NO 211
<211> LENGTH: 5
<212> TYPE: PRT
<213> ORGANISM: Artificial Sequence
<220> FEATURE:
<223> OTHER INFORMATION: Human antibody library

<400> SEQUENCE: 211

Lys Tyr Arg Met Ala
1               5

<210> SEQ ID NO 212
<211> LENGTH: 7
<212> TYPE: PRT
<213> ORGANISM: Artificial Sequence
<220> FEATURE:
<223> OTHER INFORMATION: Human antibody library

<400> SEQUENCE: 212

Gly Phe Thr Phe Ser Lys Tyr
1               5

<210> SEQ ID NO 213
<211> LENGTH: 17
<212> TYPE: PRT
<213> ORGANISM: Artificial Sequence
<220> FEATURE:
<223> OTHER INFORMATION: Human antibody library

<400> SEQUENCE: 213

Tyr Ile Tyr Pro Ser Gly Gly Phe Thr Phe Tyr Ala Asp Ser Val Lys
1               5                   10                  15

Gly

<210> SEQ ID NO 214
<211> LENGTH: 6
<212> TYPE: PRT
<213> ORGANISM: Artificial Sequence
<220> FEATURE:
<223> OTHER INFORMATION: Human antibody library

<400> SEQUENCE: 214

Tyr Pro Ser Gly Gly Phe
1               5

<210> SEQ ID NO 215
<211> LENGTH: 11
<212> TYPE: PRT
```

```
<213> ORGANISM: Artificial Sequence
<220> FEATURE:
<223> OTHER INFORMATION: Human antibody library

<400> SEQUENCE: 215

Asp Ile Gly Gln Trp Leu Phe Val Phe Asp Tyr
1               5                   10

<210> SEQ ID NO 216
<211> LENGTH: 120
<212> TYPE: PRT
<213> ORGANISM: Artificial Sequence
<220> FEATURE:
<223> OTHER INFORMATION: Human antibody library

<400> SEQUENCE: 216

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Arg Met Ala Trp Val Arg Gln Ala Pro Gly Lys Gly Leu Glu Trp Val
        35                  40                  45

Ser Tyr Ile Tyr Pro Ser Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gln Trp Leu Phe Val Phe Asp Tyr Trp Gly Gln
            100                 105                 110

Gly Thr Leu Val Thr Val Ser Ser
        115                 120

<210> SEQ ID NO 217
<211> LENGTH: 14
<212> TYPE: PRT
<213> ORGANISM: Artificial Sequence
<220> FEATURE:
<223> OTHER INFORMATION: Human antibody library

<400> SEQUENCE: 217

Thr Gly Thr Ser Ser Asp Val Gly Gly Tyr Asn Tyr Val Ser
1               5                   10

<210> SEQ ID NO 218
<211> LENGTH: 7
<212> TYPE: PRT
<213> ORGANISM: Artificial Sequence
<220> FEATURE:
<223> OTHER INFORMATION: Human antibody library

<400> SEQUENCE: 218

Asp Val Ser Asn Arg Pro Ser
1               5

<210> SEQ ID NO 219
<211> LENGTH: 10
<212> TYPE: PRT
<213> ORGANISM: Artificial Sequence
<220> FEATURE:
<223> OTHER INFORMATION: Human antibody library

<400> SEQUENCE: 219
```

```
Ser Ser Tyr Thr Asn Thr Ile Thr Val Val
1               5                   10
```

<210> SEQ ID NO 220
<211> LENGTH: 113
<212> TYPE: PRT
<213> ORGANISM: Artificial Sequence
<220> FEATURE:
<223> OTHER INFORMATION: Human antibody library

<400> SEQUENCE: 220

```
Gln Ser Glu Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Asn Thr
                85                  90                  95

Ile Thr Val Val Phe Gly Gly Gly Thr Lys Leu Thr Val Leu Gly Gln
            100                 105                 110

Pro
```

<210> SEQ ID NO 221
<211> LENGTH: 5
<212> TYPE: PRT
<213> ORGANISM: Artificial Sequence
<220> FEATURE:
<223> OTHER INFORMATION: Human antibody library

<400> SEQUENCE: 221

```
Lys Tyr Asp Met Tyr
1               5
```

<210> SEQ ID NO 222
<211> LENGTH: 7
<212> TYPE: PRT
<213> ORGANISM: Artificial Sequence
<220> FEATURE:
<223> OTHER INFORMATION: Human antibody library

<400> SEQUENCE: 222

```
Gly Phe Thr Phe Ser Lys Tyr
1               5
```

<210> SEQ ID NO 223
<211> LENGTH: 17
<212> TYPE: PRT
<213> ORGANISM: Artificial Sequence
<220> FEATURE:
<223> OTHER INFORMATION: Human antibody library

<400> SEQUENCE: 223

```
Gly Ile Trp Pro Ser Gly Gly Leu Thr Met Tyr Ala Asp Ser Val Lys
1               5                   10                  15

Gly
```

<210> SEQ ID NO 224

```
<211> LENGTH: 6
<212> TYPE: PRT
<213> ORGANISM: Artificial Sequence
<220> FEATURE:
<223> OTHER INFORMATION: Human antibody library

<400> SEQUENCE: 224

Trp Pro Ser Gly Gly Leu
1               5

<210> SEQ ID NO 225
<211> LENGTH: 12
<212> TYPE: PRT
<213> ORGANISM: Artificial Sequence
<220> FEATURE:
<223> OTHER INFORMATION: Human antibody library

<400> SEQUENCE: 225

Asp Gly Val Val Gly Gly Ser Tyr Ala Phe Asp Ile
1               5                   10

<210> SEQ ID NO 226
<211> LENGTH: 121
<212> TYPE: PRT
<213> ORGANISM: Artificial Sequence
<220> FEATURE:
<223> OTHER INFORMATION: Human antibody library

<400> SEQUENCE: 226

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Asp Met Tyr Trp Val Arg Gln Ala Pro Gly Lys Gly Leu Glu Trp Val
        35                  40                  45

Ser Gly Ile Trp Pro Ser Gly Gly Leu Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Asp Gly Val Val Gly Gly Ser Tyr Ala Phe Asp Ile Trp Gly
            100                 105                 110

Gln Gly Thr Met Val Thr Val Ser Ser
        115                 120

<210> SEQ ID NO 227
<211> LENGTH: 13
<212> TYPE: PRT
<213> ORGANISM: Artificial Sequence
<220> FEATURE:
<223> OTHER INFORMATION: Human antibody library

<400> SEQUENCE: 227

Ser Gly Ala Ser Ser Asn Leu Gly Arg Asn Thr Val Asn
1               5                   10

<210> SEQ ID NO 228
<211> LENGTH: 7
<212> TYPE: PRT
<213> ORGANISM: Artificial Sequence
<220> FEATURE:
<223> OTHER INFORMATION: Human antibody library
```

<400> SEQUENCE: 228

Thr Asn Asp His Arg Pro Ser
1               5

<210> SEQ ID NO 229
<211> LENGTH: 11
<212> TYPE: PRT
<213> ORGANISM: Artificial Sequence
<220> FEATURE:
<223> OTHER INFORMATION: Human antibody library

<400> SEQUENCE: 229

Ala Ala Trp Asp His Ser Leu Asn Gly Tyr Val
1               5                   10

<210> SEQ ID NO 230
<211> LENGTH: 113
<212> TYPE: PRT
<213> ORGANISM: Artificial Sequence
<220> FEATURE:
<223> OTHER INFORMATION: Human antibody library

<400> SEQUENCE: 230

Gln Ser Ala Leu Thr Gln Pro Pro Ser Ala Ser Gly Thr Pro Gly Gln
1               5                   10                  15

Arg Val Thr Ile Ser Cys Ser Gly Ala Ser Ser Asn Leu Gly Arg Asn
            20                  25                  30

Thr Val Asn Trp Tyr Gln Gln Val Pro Gly Ser Ala Pro Lys Leu Leu
        35                  40                  45

Ile Tyr Thr Asn Asp His Arg Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp His Ser Leu
                85                  90                  95

Asn Gly Tyr Val Phe Gly Pro Gly Thr Lys Val Thr Val Leu Ser Gln
            100                 105                 110

Pro

<210> SEQ ID NO 231
<211> LENGTH: 5
<212> TYPE: PRT
<213> ORGANISM: Artificial Sequence
<220> FEATURE:
<223> OTHER INFORMATION: Human antibody library

<400> SEQUENCE: 231

Ile Tyr Ser Met Asn
1               5

<210> SEQ ID NO 232
<211> LENGTH: 7
<212> TYPE: PRT
<213> ORGANISM: Artificial Sequence
<220> FEATURE:
<223> OTHER INFORMATION: Human antibody library

<400> SEQUENCE: 232

Gly Phe Thr Phe Ser Ile Tyr
1               5

<210> SEQ ID NO 233

```
<211> LENGTH: 17
<212> TYPE: PRT
<213> ORGANISM: Artificial Sequence
<220> FEATURE:
<223> OTHER INFORMATION: Human antibody library

<400> SEQUENCE: 233

Val Ile Tyr Pro Ser Gly Gly Phe Thr His Tyr Ala Asp Ser Val Lys
1               5                   10                  15
Gly

<210> SEQ ID NO 234
<211> LENGTH: 6
<212> TYPE: PRT
<213> ORGANISM: Artificial Sequence
<220> FEATURE:
<223> OTHER INFORMATION: Human antibody library

<400> SEQUENCE: 234

Tyr Pro Ser Gly Gly Phe
1               5

<210> SEQ ID NO 235
<211> LENGTH: 11
<212> TYPE: PRT
<213> ORGANISM: Artificial Sequence
<220> FEATURE:
<223> OTHER INFORMATION: Human antibody library

<400> SEQUENCE: 235

Gly Arg Lys Thr Thr Val Thr Asp Phe Asp Tyr
1               5                   10

<210> SEQ ID NO 236
<211> LENGTH: 120
<212> TYPE: PRT
<213> ORGANISM: Artificial Sequence
<220> FEATURE:
<223> OTHER INFORMATION: Human antibody library

<400> SEQUENCE: 236

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ser Met Asn Trp Val Arg Gln Ala Pro Gly Lys Gly Leu Glu Trp Val
        35                  40                  45

Ser Val Ile Tyr Pro Ser Gly Gly Phe Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Lys Thr Thr Val Thr Asp Phe Asp Tyr Trp Gly Gln
            100                 105                 110

Gly Thr Leu Val Thr Val Ser Ser
        115                 120

<210> SEQ ID NO 237
<211> LENGTH: 14
<212> TYPE: PRT
<213> ORGANISM: Artificial Sequence
<220> FEATURE:
```

<223> OTHER INFORMATION: Human antibody library

<400> SEQUENCE: 237

Thr Gly Thr Ser Ser Asp Val Gly Gly Tyr Asn Tyr Val Ser
1               5                   10

<210> SEQ ID NO 238
<211> LENGTH: 7
<212> TYPE: PRT
<213> ORGANISM: Artificial Sequence
<220> FEATURE:
<223> OTHER INFORMATION: Human antibody library

<400> SEQUENCE: 238

Glu Val Ser His Arg Pro Ser
1               5

<210> SEQ ID NO 239
<211> LENGTH: 10
<212> TYPE: PRT
<213> ORGANISM: Artificial Sequence
<220> FEATURE:
<223> OTHER INFORMATION: Human antibody library

<400> SEQUENCE: 239

Ser Ser Tyr Thr Ser Gly Ser Thr Arg Val
1               5                   10

<210> SEQ ID NO 240
<211> LENGTH: 113
<212> TYPE: PRT
<213> ORGANISM: Artificial Sequence
<220> FEATURE:
<223> OTHER INFORMATION: Human antibody library

<400> SEQUENCE: 240

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Val
        35                  40                  45

Met Ile Tyr Glu Val Ser His Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Gly
                85                  90                  95

Ser Thr Arg Val Phe Gly Gly Gly Thr Lys Val Thr Val Leu Gly Gln
            100                 105                 110

Pro

<210> SEQ ID NO 241
<211> LENGTH: 5
<212> TYPE: PRT
<213> ORGANISM: Artificial Sequence
<220> FEATURE:
<223> OTHER INFORMATION: Human antibody library

<400> SEQUENCE: 241

Met Tyr Met Met Met
1               5

<210> SEQ ID NO 242
<211> LENGTH: 7
<212> TYPE: PRT
<213> ORGANISM: Artificial Sequence
<220> FEATURE:
<223> OTHER INFORMATION: Human antibody library

<400> SEQUENCE: 242

Gly Phe Thr Phe Ser Met Tyr
1               5

<210> SEQ ID NO 243
<211> LENGTH: 17
<212> TYPE: PRT
<213> ORGANISM: Artificial Sequence
<220> FEATURE:
<223> OTHER INFORMATION: Human antibody library

<400> SEQUENCE: 243

Ser Ile Tyr Pro Ser Gly Gly Ile Thr Phe Tyr Ala Asp Ser Val Lys
1               5                   10                  15

Gly

<210> SEQ ID NO 244
<211> LENGTH: 6
<212> TYPE: PRT
<213> ORGANISM: Artificial Sequence
<220> FEATURE:
<223> OTHER INFORMATION: Human antibody library

<400> SEQUENCE: 244

Tyr Pro Ser Gly Gly Ile
1               5

<210> SEQ ID NO 245
<211> LENGTH: 11
<212> TYPE: PRT
<213> ORGANISM: Artificial Sequence
<220> FEATURE:
<223> OTHER INFORMATION: Human antibody library

<400> SEQUENCE: 245

Ile Lys Leu Gly Thr Val Thr Thr Val Asp Tyr
1               5                   10

<210> SEQ ID NO 246
<211> LENGTH: 120
<212> TYPE: PRT
<213> ORGANISM: Artificial Sequence
<220> FEATURE:
<223> OTHER INFORMATION: Human antibody library

<400> SEQUENCE: 246

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
                20                  25                  30

Met Met Met Trp Val Arg Gln Ala Pro Gly Lys Gly Leu Glu Trp Val
            35                  40                  45

Ser Ser Ile Tyr Pro Ser Gly Gly Ile Thr Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Val Asp Tyr Trp Gly Gln
            100                 105                 110

Gly Thr Leu Val Thr Val Ser Ser
        115                 120

<210> SEQ ID NO 247
<211> LENGTH: 14
<212> TYPE: PRT
<213> ORGANISM: Artificial Sequence
<220> FEATURE:
<223> OTHER INFORMATION: Human antibody library

<400> SEQUENCE: 247

Thr Gly Thr Ser Ser Asp Val Gly Ala Tyr Asn Tyr Val Ser
1               5                   10

<210> SEQ ID NO 248
<211> LENGTH: 7
<212> TYPE: PRT
<213> ORGANISM: Artificial Sequence
<220> FEATURE:
<223> OTHER INFORMATION: Human antibody library

<400> SEQUENCE: 248

Asp Val Ser Asn Arg Pro Ser
1               5

<210> SEQ ID NO 249
<211> LENGTH: 10
<212> TYPE: PRT
<213> ORGANISM: Artificial Sequence
<220> FEATURE:
<223> OTHER INFORMATION: Human antibody library

<400> SEQUENCE: 249

Ser Ser Tyr Thr Ser Ser Ser Thr Arg Val
1               5                   10

<210> SEQ ID NO 250
<211> LENGTH: 113
<212> TYPE: PRT
<213> ORGANISM: Artificial Sequence
<220> FEATURE:
<223> OTHER INFORMATION: Human antibody library

<400> SEQUENCE: 250

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro

<210> SEQ ID NO 251
<211> LENGTH: 5
<212> TYPE: PRT
<213> ORGANISM: Artificial Sequence
<220> FEATURE:
<223> OTHER INFORMATION: Human antibody library

<400> SEQUENCE: 251

Ala Tyr Arg Met Val
1               5

<210> SEQ ID NO 252
<211> LENGTH: 7
<212> TYPE: PRT
<213> ORGANISM: Artificial Sequence
<220> FEATURE:
<223> OTHER INFORMATION: Human antibody library

<400> SEQUENCE: 252

Gly Phe Thr Phe Ser Ala Tyr
1               5

<210> SEQ ID NO 253
<211> LENGTH: 17
<212> TYPE: PRT
<213> ORGANISM: Artificial Sequence
<220> FEATURE:
<223> OTHER INFORMATION: Human antibody library

<400> SEQUENCE: 253

Arg Ile Tyr Pro Ser Gly Gly Phe Thr Phe Tyr Ala Asp Ser Val Lys
1               5                   10                  15

Gly

<210> SEQ ID NO 254
<211> LENGTH: 6
<212> TYPE: PRT
<213> ORGANISM: Artificial Sequence
<220> FEATURE:
<223> OTHER INFORMATION: Human antibody library

<400> SEQUENCE: 254

Tyr Pro Ser Gly Gly Phe
1               5

<210> SEQ ID NO 255
<211> LENGTH: 10
<212> TYPE: PRT
<213> ORGANISM: Artificial Sequence
<220> FEATURE:
<223> OTHER INFORMATION: Human antibody library

<400> SEQUENCE: 255

Ala Leu Gly Pro Leu Ser Pro Leu Asp Ser
1               5                   10

<210> SEQ ID NO 256
<211> LENGTH: 119
<212> TYPE: PRT
<213> ORGANISM: Artificial Sequence
<220> FEATURE:
<223> OTHER INFORMATION: Human antibody library

<400> SEQUENCE: 256

-continued

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Arg Met Val Trp Val Arg Gln Ala Pro Gly Lys Gly Leu Glu Trp Val
        35                  40                  45

Ser Arg Ile Tyr Pro Ser Gly Gly Phe Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Gly Pro Leu Ser Pro Leu Asp Ser Trp Gly Gln Gly
            100                 105                 110

Thr Leu Val Thr Val Ser Ser
            115

<210> SEQ ID NO 257
<211> LENGTH: 14
<212> TYPE: PRT
<213> ORGANISM: Artificial Sequence
<220> FEATURE:
<223> OTHER INFORMATION: Human antibody library

<400> SEQUENCE: 257

Thr Gly Thr Ser Ser Asp Val Gly Gly Tyr Asn Tyr Val Ser
1               5                   10

<210> SEQ ID NO 258
<211> LENGTH: 7
<212> TYPE: PRT
<213> ORGANISM: Artificial Sequence
<220> FEATURE:
<223> OTHER INFORMATION: Human antibody library

<400> SEQUENCE: 258

Glu Val Ser Asn Arg Pro Ser
1               5

<210> SEQ ID NO 259
<211> LENGTH: 10
<212> TYPE: PRT
<213> ORGANISM: Artificial Sequence
<220> FEATURE:
<223> OTHER INFORMATION: Human antibody library

<400> SEQUENCE: 259

Ser Ser Tyr Arg Ser Gly Asn Thr Leu Val
1               5                   10

<210> SEQ ID NO 260
<211> LENGTH: 113
<212> TYPE: PRT
<213> ORGANISM: Artificial Sequence
<220> FEATURE:
<223> OTHER INFORMATION: Human antibody library

<400> SEQUENCE: 260

Gln Ser Glu Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

```
Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Gly Asp Tyr Tyr Cys Ser Ser Tyr Arg Ser Gly
                 85                  90                  95

Asn Thr Leu Val Phe Gly Gly Gly Thr Lys Val Thr Val Leu Gly Gln
                100                 105                 110

Pro

<210> SEQ ID NO 261
<211> LENGTH: 209
<212> TYPE: PRT
<213> ORGANISM: Artificial Sequence
<220> FEATURE:
<223> OTHER INFORMATION: SD15 fusion protein
<220> FEATURE:
<221> NAME/KEY: DOMAIN
<222> LOCATION: (1)..(61)
<223> OTHER INFORMATION: human ILL-15Ra Sushi domain (NM-002189)
<220> FEATURE:
<221> NAME/KEY: DOMAIN
<222> LOCATION: (62)..(75)
<223> OTHER INFORMATION: IRD-11exone3
<220> FEATURE:
<221> NAME/KEY: DOMAIN
<222> LOCATION: (76)..(95)
<223> OTHER INFORMATION: linker
<220> FEATURE:
<221> NAME/KEY: DOMAIN
<222> LOCATION: (96)..(209)
<223> OTHER INFORMATION: human IL-15 (NM-000585-3)

<400> SEQUENCE: 261

Cys Pro Pro Pro Met Ser Val Glu His Ala Asp Ile Trp Val Lys Ser
 1               5                  10                  15

Tyr Ser Leu Tyr Ser Arg Glu Arg Tyr Ile Cys Asn Ser Gly Phe Lys
                 20                  25                  30

Arg Lys Ala Gly Thr Ser Ser Leu Thr Glu Cys Val Leu Asn Lys Ala
            35                  40                  45

Thr Asn Val Ala His Trp Thr Thr Pro Ser Leu Lys Cys Ile Arg Asp
 50                  55                  60

Pro Ala Leu Val His Gln Arg Pro Ala Pro Pro Ser Gly Gly Ser Gly
 65                  70                  75                  80

Gly Gly Gly Ser Gly Gly Gly Ser Gly Gly Gly Gly Ser Leu Gln Asn
                 85                  90                  95

Trp Val Asn Val Ile Ser Asp Leu Lys Lys Ile Glu Asp Leu Ile Gln
                100                 105                 110

Ser Met His Ile Asp Ala Thr Leu Tyr Thr Glu Ser Asp Val His Pro
            115                 120                 125

Ser Cys Lys Val Thr Ala Met Lys Cys Phe Leu Leu Glu Leu Gln Val
130                 135                 140

Ile Ser Leu Glu Ser Gly Asp Ala Ser Ile His Asp Thr Val Glu Asn
145                 150                 155                 160

Leu Ile Ile Leu Ala Asn Asn Ser Leu Ser Ser Asn Gly Asn Val Thr
                165                 170                 175

Glu Ser Gly Cys Lys Glu Cys Glu Glu Leu Glu Glu Lys Asn Ile Lys
            180                 185                 190
```

Glu Phe Leu Gln Ser Phe Val His Ile Val Gln Met Phe Ile Asn Thr
            195                 200                 205

Ser

<210> SEQ ID NO 262
<211> LENGTH: 659
<212> TYPE: PRT
<213> ORGANISM: Artificial Sequence
<220> FEATURE:
<223> OTHER INFORMATION: Fusion protein

<400> SEQUENCE: 262

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Met Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr

```
                340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Ser Cys Pro Pro Met Ser Val Glu His Ala Asp Ile Trp Val
    450                 455                 460
Lys Ser Tyr Ser Leu Tyr Ser Arg Glu Arg Tyr Ile Cys Asn Ser Gly
465                 470                 475                 480
Phe Lys Arg Lys Ala Gly Thr Ser Ser Leu Thr Glu Cys Val Leu Asn
                485                 490                 495
Lys Ala Thr Asn Val Ala His Trp Thr Thr Pro Ser Leu Lys Cys Ile
            500                 505                 510
Arg Asp Pro Ala Leu Val His Gln Arg Pro Ala Pro Pro Ser Gly Gly
        515                 520                 525
Ser Gly Gly Gly Gly Ser Gly Gly Gly Ser Gly Gly Gly Gly Ser Leu
    530                 535                 540
Gln Asn Trp Val Asn Val Ile Ser Asp Leu Lys Lys Ile Glu Asp Leu
545                 550                 555                 560
Ile Gln Ser Met His Ile Asp Ala Thr Leu Tyr Thr Glu Ser Asp Val
                565                 570                 575
His Pro Ser Cys Lys Val Thr Ala Met Lys Cys Phe Leu Leu Glu Leu
            580                 585                 590
Gln Val Ile Ser Leu Glu Ser Gly Asp Ala Ser Ile His Asp Thr Val
        595                 600                 605
Glu Asn Leu Ile Ile Leu Ala Asn Asn Ser Leu Ser Ser Asn Gly Asn
    610                 615                 620
Val Thr Glu Ser Gly Cys Lys Glu Cys Glu Glu Leu Glu Glu Lys Asn
625                 630                 635                 640
Ile Lys Glu Phe Leu Gln Ser Phe Val His Ile Val Gln Met Phe Ile
                645                 650                 655
Asn Thr Ser

<210> SEQ ID NO 263
<211> LENGTH: 659
<212> TYPE: PRT
<213> ORGANISM: Artificial Sequence
<220> FEATURE:
<223> OTHER INFORMATION: Fusion protein

<400> SEQUENCE: 263

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Met Tyr
            20                  25                  30
Met Met Met Trp Val Arg Gln Ala Pro Gly Lys Gly Leu Glu Trp Val
        35                  40                  45
```

Ser Ser Ile Tyr Pro Ser Gly Ile Thr Phe Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Ser Cys Pro Pro Pro Met Ser Val Glu His Ala Asp Ile Trp Val
    450                 455                 460

-continued

```
Lys Ser Tyr Ser Leu Tyr Ser Arg Glu Arg Tyr Ile Cys Asn Ser Gly
465                 470                 475                 480

Phe Lys Arg Lys Ala Gly Thr Ser Ser Leu Thr Glu Cys Val Leu Asn
            485                 490                 495

Lys Ala Thr Asn Val Ala His Trp Thr Thr Pro Ser Leu Lys Cys Ile
        500                 505                 510

Arg Asp Pro Ala Leu Val His Gln Arg Pro Ala Pro Pro Ser Gly Gly
    515                 520                 525

Ser Gly Gly Gly Gly Ser Gly Gly Gly Ser Gly Gly Gly Ser Leu
530                 535                 540

Gln Asn Trp Val Asn Val Ile Ser Asp Leu Lys Lys Ile Glu Asp Leu
545                 550                 555                 560

Ile Gln Ser Met His Ile Asp Ala Thr Leu Tyr Thr Glu Ser Asp Val
            565                 570                 575

His Pro Ser Cys Lys Val Thr Ala Met Lys Cys Phe Leu Leu Glu Leu
        580                 585                 590

Gln Val Ile Ser Leu Glu Ser Gly Asp Ala Ser Ile His Asp Thr Val
    595                 600                 605

Glu Asn Leu Ile Ile Leu Ala Asn Asn Ser Leu Ser Ser Asn Gly Asn
610                 615                 620

Val Thr Glu Ser Gly Cys Lys Glu Cys Glu Glu Leu Glu Glu Lys Asn
625                 630                 635                 640

Ile Lys Glu Phe Leu Gln Ser Phe Val His Ile Val Gln Met Phe Ile
            645                 650                 655

Asn Thr Ser

<210> SEQ ID NO 264
<211> LENGTH: 5
<212> TYPE: PRT
<213> ORGANISM: Artificial Sequence
<220> FEATURE:
<223> OTHER INFORMATION: synthetic

<400> SEQUENCE: 264

Ala Tyr Ala Met Ala
1               5

<210> SEQ ID NO 265
<211> LENGTH: 120
<212> TYPE: PRT
<213> ORGANISM: Artificial Sequence
<220> FEATURE:
<223> OTHER INFORMATION: synthetic

<400> SEQUENCE: 265

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Ala Met Ala Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
            85                  90                  95
```

-continued

Ala Arg Ile Lys Leu Gly Thr Val Thr Val Asp Tyr Trp Gly Gln
            100                 105                 110

Gly Thr Leu Val Thr Val Ser Ser
        115                 120

<210> SEQ ID NO 266
<211> LENGTH: 5
<212> TYPE: PRT
<213> ORGANISM: Artificial Sequence
<220> FEATURE:
<223> OTHER INFORMATION: synthetic

<400> SEQUENCE: 266

Ala Tyr Arg Met Phe
1               5

<210> SEQ ID NO 267
<211> LENGTH: 120
<212> TYPE: PRT
<213> ORGANISM: Artificial Sequence
<220> FEATURE:
<223> OTHER INFORMATION: synthetic

<400> SEQUENCE: 267

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Arg Met Phe Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Val Asp Tyr Trp Gly Gln
            100                 105                 110

Gly Thr Leu Val Thr Val Ser Ser
        115                 120

<210> SEQ ID NO 268
<211> LENGTH: 5
<212> TYPE: PRT
<213> ORGANISM: Artificial Sequence
<220> FEATURE:
<223> OTHER INFORMATION: synthetic

<400> SEQUENCE: 268

Ala Tyr Leu Met Val
1               5

<210> SEQ ID NO 269
<211> LENGTH: 120
<212> TYPE: PRT
<213> ORGANISM: Artificial Sequence
<220> FEATURE:
<223> OTHER INFORMATION: synthetic

<400> SEQUENCE: 269

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ala Tyr
            20                  25                  30

Leu Met Val Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser
        115                 120

<210> SEQ ID NO 270
<211> LENGTH: 5
<212> TYPE: PRT
<213> ORGANISM: Artificial Sequence
<220> FEATURE:
<223> OTHER INFORMATION: synthetic

<400> SEQUENCE: 270

Ala Tyr Val Met Phe
1               5

<210> SEQ ID NO 271
<211> LENGTH: 120
<212> TYPE: PRT
<213> ORGANISM: Artificial Sequence
<220> FEATURE:
<223> OTHER INFORMATION: synthetic

<400> SEQUENCE: 271

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Val Met Phe Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser
        115                 120

<210> SEQ ID NO 272
<211> LENGTH: 5
<212> TYPE: PRT
<213> ORGANISM: Artificial Sequence
<220> FEATURE:
<223> OTHER INFORMATION: synthetic

<400> SEQUENCE: 272

Ala Tyr Val Met Ser
1               5
```

<210> SEQ ID NO 273
<211> LENGTH: 120
<212> TYPE: PRT
<213> ORGANISM: Artificial Sequence
<220> FEATURE:
<223> OTHER INFORMATION: synthetic

<400> SEQUENCE: 273

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ala Tyr
            20                  25                  30
Val Met Ser Trp Val Arg Gln Ala Pro Gly Lys Gly Leu Glu Trp Val
        35                  40                  45
Ser Ser Ile Tyr Pro Ser Gly Gly Ile Thr Phe Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Ile Tyr Tyr Cys
                85                  90                  95
Ala Arg Ile Lys Leu Gly Thr Val Thr Thr Val Asp Tyr Trp Gly Gln
            100                 105                 110
Gly Thr Leu Val Thr Val Ser Ser
        115                 120

<210> SEQ ID NO 274
<211> LENGTH: 5
<212> TYPE: PRT
<213> ORGANISM: Artificial Sequence
<220> FEATURE:
<223> OTHER INFORMATION: synthetic

<400> SEQUENCE: 274

Gly Tyr Leu Met Val
1               5

<210> SEQ ID NO 275
<211> LENGTH: 120
<212> TYPE: PRT
<213> ORGANISM: Artificial Sequence
<220> FEATURE:
<223> OTHER INFORMATION: synthetic

<400> SEQUENCE: 275

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Gly Tyr
            20                  25                  30
Leu Met Val Trp Val Arg Gln Ala Pro Gly Lys Gly Leu Glu Trp Val
        35                  40                  45
Ser Ser Ile Tyr Pro Ser Gly Gly Ile Thr Phe Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Ile Tyr Tyr Cys
                85                  90                  95
Ala Arg Ile Lys Leu Gly Thr Val Thr Thr Val Asp Tyr Trp Gly Gln
            100                 105                 110

Gly Thr Leu Val Thr Val Ser Ser
        115             120

<210> SEQ ID NO 276
<211> LENGTH: 5
<212> TYPE: PRT
<213> ORGANISM: Artificial Sequence
<220> FEATURE:
<223> OTHER INFORMATION: synthetic

<400> SEQUENCE: 276

Gly Tyr Gln Met Leu
1               5

<210> SEQ ID NO 277
<211> LENGTH: 120
<212> TYPE: PRT
<213> ORGANISM: Artificial Sequence
<220> FEATURE:
<223> OTHER INFORMATION: synthetic

<400> SEQUENCE: 277

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Gln Met Leu Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser
        115             120

<210> SEQ ID NO 278
<211> LENGTH: 5
<212> TYPE: PRT
<213> ORGANISM: Artificial Sequence
<220> FEATURE:
<223> OTHER INFORMATION: synthetic

<400> SEQUENCE: 278

Gly Tyr Ser Met Phe
1               5

<210> SEQ ID NO 279
<211> LENGTH: 120
<212> TYPE: PRT
<213> ORGANISM: Artificial Sequence
<220> FEATURE:
<223> OTHER INFORMATION: synthetic

<400> SEQUENCE: 279

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

```
Ser Met Phe Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Val Asp Tyr Trp Gly Gln
            100                 105                 110

Gly Thr Leu Val Thr Val Ser Ser
        115                 120

<210> SEQ ID NO 280
<211> LENGTH: 5
<212> TYPE: PRT
<213> ORGANISM: Artificial Sequence
<220> FEATURE:
<223> OTHER INFORMATION: synthetic

<400> SEQUENCE: 280

Gly Tyr Trp Met Ala
1               5

<210> SEQ ID NO 281
<211> LENGTH: 120
<212> TYPE: PRT
<213> ORGANISM: Artificial Sequence
<220> FEATURE:
<223> OTHER INFORMATION: synthetic

<400> SEQUENCE: 281

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Trp Met Ala Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Val Asp Tyr Trp Gly Gln
            100                 105                 110

Gly Thr Leu Val Thr Val Ser Ser
        115                 120

<210> SEQ ID NO 282
<211> LENGTH: 5
<212> TYPE: PRT
<213> ORGANISM: Artificial Sequence
<220> FEATURE:
<223> OTHER INFORMATION: synthetic

<400> SEQUENCE: 282

Gln Tyr Leu Met Tyr
1               5
```

```
<210> SEQ ID NO 283
<211> LENGTH: 120
<212> TYPE: PRT
<213> ORGANISM: Artificial Sequence
<220> FEATURE:
<223> OTHER INFORMATION: synthetic

<400> SEQUENCE: 283

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Leu Met Tyr Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser
        115                 120

<210> SEQ ID NO 284
<211> LENGTH: 5
<212> TYPE: PRT
<213> ORGANISM: Artificial Sequence
<220> FEATURE:
<223> OTHER INFORMATION: synthetic

<400> SEQUENCE: 284

Gln Tyr Val Met Phe
1               5

<210> SEQ ID NO 285
<211> LENGTH: 120
<212> TYPE: PRT
<213> ORGANISM: Artificial Sequence
<220> FEATURE:
<223> OTHER INFORMATION: synthetic

<400> SEQUENCE: 285

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Val Met Phe Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser
```

```
<210> SEQ ID NO 286
<211> LENGTH: 5
<212> TYPE: PRT
<213> ORGANISM: Artificial Sequence
<220> FEATURE:
<223> OTHER INFORMATION: synthetic

<400> SEQUENCE: 286

Gln Tyr Tyr Met Tyr
1               5

<210> SEQ ID NO 287
<211> LENGTH: 120
<212> TYPE: PRT
<213> ORGANISM: Artificial Sequence
<220> FEATURE:
<223> OTHER INFORMATION: synthetic

<400> SEQUENCE: 287

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Tyr Met Tyr Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Val Asp Tyr Trp Gly Gln
                100                 105                 110

Gly Thr Leu Val Thr Val Ser Ser
            115                 120

<210> SEQ ID NO 288
<211> LENGTH: 5
<212> TYPE: PRT
<213> ORGANISM: Artificial Sequence
<220> FEATURE:
<223> OTHER INFORMATION: synthetic

<400> SEQUENCE: 288

Ser Tyr Leu Met Ser
1               5

<210> SEQ ID NO 289
<211> LENGTH: 120
<212> TYPE: PRT
<213> ORGANISM: Artificial Sequence
<220> FEATURE:
<223> OTHER INFORMATION: synthetic

<400> SEQUENCE: 289

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Leu Met Ser Trp Val Arg Gln Ala Pro Gly Lys Gly Leu Glu Trp Val
```

```
                35                  40                  45
Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Val Asp Tyr Trp Gly Gln
                100                 105                 110

Gly Thr Leu Val Thr Val Ser Ser
        115                 120

<210> SEQ ID NO 290
<211> LENGTH: 5
<212> TYPE: PRT
<213> ORGANISM: Artificial Sequence
<220> FEATURE:
<223> OTHER INFORMATION: synthetic

<400> SEQUENCE: 290

Ser Tyr Leu Met Val
1               5

<210> SEQ ID NO 291
<211> LENGTH: 120
<212> TYPE: PRT
<213> ORGANISM: Artificial Sequence
<220> FEATURE:
<223> OTHER INFORMATION: synthetic

<400> SEQUENCE: 291

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
                20                  25                  30

Leu Met Val Trp Val Arg Gln Ala Pro Gly Lys Gly Leu Glu Trp Val
                35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Val Asp Tyr Trp Gly Gln
                100                 105                 110

Gly Thr Leu Val Thr Val Ser Ser
        115                 120

<210> SEQ ID NO 292
<211> LENGTH: 12
<212> TYPE: PRT
<213> ORGANISM: Artificial Sequence
<220> FEATURE:
<223> OTHER INFORMATION: synthetic

<400> SEQUENCE: 292

Ser Tyr Leu Met Thr Thr Cys Cys Leu Asp His Lys
1               5                  10

<210> SEQ ID NO 293
```

```
<211> LENGTH: 120
<212> TYPE: PRT
<213> ORGANISM: Artificial Sequence
<220> FEATURE:
<223> OTHER INFORMATION: synthetic

<400> SEQUENCE: 293
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Leu Met Thr Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Val Asp Tyr Trp Gly Gln
            100                 105                 110

Gly Thr Leu Val Thr Val Ser Ser
        115                 120

```
<210> SEQ ID NO 294
<211> LENGTH: 5
<212> TYPE: PRT
<213> ORGANISM: Artificial Sequence
<220> FEATURE:
<223> OTHER INFORMATION: synthetic

<400> SEQUENCE: 294
```

Ser Tyr Gln Met Val
1               5

```
<210> SEQ ID NO 295
<211> LENGTH: 120
<212> TYPE: PRT
<213> ORGANISM: Artificial Sequence
<220> FEATURE:
<223> OTHER INFORMATION: synthetic

<400> SEQUENCE: 295
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Val Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Val Asp Tyr Trp Gly Gln
            100                 105                 110

Gly Thr Leu Val Thr Val Ser Ser
        115                 120

```
<210> SEQ ID NO 296
<211> LENGTH: 5
<212> TYPE: PRT
<213> ORGANISM: Artificial Sequence
<220> FEATURE:
<223> OTHER INFORMATION: synthetic

<400> SEQUENCE: 296

Ser Tyr Ser Met Ala
1               5

<210> SEQ ID NO 297
<211> LENGTH: 120
<212> TYPE: PRT
<213> ORGANISM: Artificial Sequence
<220> FEATURE:
<223> OTHER INFORMATION: synthetic

<400> SEQUENCE: 297

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ala Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser
        115                 120

<210> SEQ ID NO 298
<211> LENGTH: 5
<212> TYPE: PRT
<213> ORGANISM: Artificial Sequence
<220> FEATURE:
<223> OTHER INFORMATION: synthetic

<400> SEQUENCE: 298

Ser Tyr Val Met Phe
1               5

<210> SEQ ID NO 299
<211> LENGTH: 120
<212> TYPE: PRT
<213> ORGANISM: Artificial Sequence
<220> FEATURE:
<223> OTHER INFORMATION: synthetic

<400> SEQUENCE: 299

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Phe Trp Val Arg Gln Ala Pro Gly Lys Gly Leu Glu Trp Val
        35                  40                  45
```

Ser Ser Ile Tyr Pro Ser Gly Gly Ile Thr Phe Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ala Arg Ile Lys Leu Gly Thr Val Thr Val Asp Tyr Trp Gly Gln
                100                 105                 110

Gly Thr Leu Val Thr Val Ser Ser
        115                 120

<210> SEQ ID NO 300
<211> LENGTH: 5
<212> TYPE: PRT
<213> ORGANISM: Artificial Sequence
<220> FEATURE:
<223> OTHER INFORMATION: synthetic

<400> SEQUENCE: 300

Ser Tyr Val Met Ser
 1               5

<210> SEQ ID NO 301
<211> LENGTH: 120
<212> TYPE: PRT
<213> ORGANISM: Artificial Sequence
<220> FEATURE:
<223> OTHER INFORMATION: synthetic

<400> SEQUENCE: 301

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Val Met Ser Trp Val Arg Gln Ala Pro Gly Lys Gly Leu Glu Trp Val
             35                  40                  45

Ser Ser Ile Tyr Pro Ser Gly Gly Ile Thr Phe Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ala Arg Ile Lys Leu Gly Thr Val Thr Val Asp Tyr Trp Gly Gln
                100                 105                 110

Gly Thr Leu Val Thr Val Ser Ser
        115                 120

<210> SEQ ID NO 302
<211> LENGTH: 5
<212> TYPE: PRT
<213> ORGANISM: Artificial Sequence
<220> FEATURE:
<223> OTHER INFORMATION: synthetic

<400> SEQUENCE: 302

Ser Tyr Val Met Tyr
 1               5

<210> SEQ ID NO 303
<211> LENGTH: 120
<212> TYPE: PRT

<213> ORGANISM: Artificial Sequence
<220> FEATURE:
<223> OTHER INFORMATION: synthetic

<400> SEQUENCE: 303

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Val Met Tyr Trp Val Arg Gln Ala Pro Gly Lys Gly Leu Glu Trp Val
        35                  40                  45
Ser Ser Ile Tyr Pro Ser Gly Gly Ile Thr Phe Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Ile Tyr Tyr Cys
                85                  90                  95
Ala Arg Ile Lys Leu Gly Thr Val Thr Thr Val Asp Tyr Trp Gly Gln
            100                 105                 110
Gly Thr Leu Val Thr Val Ser Ser
        115                 120
```

<210> SEQ ID NO 304
<211> LENGTH: 5
<212> TYPE: PRT
<213> ORGANISM: Artificial Sequence
<220> FEATURE:
<223> OTHER INFORMATION: synthetic

<400> SEQUENCE: 304

```
Ser Tyr Tyr Met Phe
1               5
```

<210> SEQ ID NO 305
<211> LENGTH: 120
<212> TYPE: PRT
<213> ORGANISM: Artificial Sequence
<220> FEATURE:
<223> OTHER INFORMATION: synthetic

<400> SEQUENCE: 305

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Tyr Met Phe Trp Val Arg Gln Ala Pro Gly Lys Gly Leu Glu Trp Val
        35                  40                  45
Ser Ser Ile Tyr Pro Ser Gly Gly Ile Thr Phe Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Ile Tyr Tyr Cys
                85                  90                  95
Ala Arg Ile Lys Leu Gly Thr Val Thr Thr Val Asp Tyr Trp Gly Gln
            100                 105                 110
Gly Thr Leu Val Thr Val Ser Ser
        115                 120
```

<210> SEQ ID NO 306

```
<211> LENGTH: 5
<212> TYPE: PRT
<213> ORGANISM: Artificial Sequence
<220> FEATURE:
<223> OTHER INFORMATION: synthetic

<400> SEQUENCE: 306

Ser Tyr Tyr Met Val
1               5

<210> SEQ ID NO 307
<211> LENGTH: 120
<212> TYPE: PRT
<213> ORGANISM: Artificial Sequence
<220> FEATURE:
<223> OTHER INFORMATION: synthetic

<400> SEQUENCE: 307

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Val Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser
        115                 120

<210> SEQ ID NO 308
<211> LENGTH: 5
<212> TYPE: PRT
<213> ORGANISM: Artificial Sequence
<220> FEATURE:
<223> OTHER INFORMATION: synthetic

<400> SEQUENCE: 308

Tyr Tyr Ser Met Val
1               5

<210> SEQ ID NO 309
<211> LENGTH: 120
<212> TYPE: PRT
<213> ORGANISM: Artificial Sequence
<220> FEATURE:
<223> OTHER INFORMATION: synthetic

<400> SEQUENCE: 309

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Ser Met Val Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Val Asp Tyr Trp Gly Gln
            100                 105                 110

Gly Thr Leu Val Thr Val Ser Ser
        115                 120

<210> SEQ ID NO 310
<211> LENGTH: 5
<212> TYPE: PRT
<213> ORGANISM: Artificial Sequence
<220> FEATURE:
<223> OTHER INFORMATION: synthetic

<400> SEQUENCE: 310

Trp Tyr Leu Met Ala
1               5

<210> SEQ ID NO 311
<211> LENGTH: 120
<212> TYPE: PRT
<213> ORGANISM: Artificial Sequence
<220> FEATURE:
<223> OTHER INFORMATION: synthetic

<400> SEQUENCE: 311

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Leu Met Ala Trp Val Arg Gln Ala Pro Gly Lys Gly Leu Glu Trp Val
        35                  40                  45

Ser Ser Ile Tyr Pro Ser Gly Ile Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Val Asp Tyr Trp Gly Gln
            100                 105                 110

Gly Thr Leu Val Thr Val Ser Ser
        115                 120

<210> SEQ ID NO 312
<211> LENGTH: 5
<212> TYPE: PRT
<213> ORGANISM: Artificial Sequence
<220> FEATURE:
<223> OTHER INFORMATION: synthetic

<400> SEQUENCE: 312

Trp Tyr Gln Met Ser
1               5

<210> SEQ ID NO 313
<211> LENGTH: 120
<212> TYPE: PRT
<213> ORGANISM: Artificial Sequence
<220> FEATURE:

<223> OTHER INFORMATION: synthetic

<400> SEQUENCE: 313

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Gln Met Ser Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ile Lys Leu Gly Thr Val Thr Val Asp Tyr Trp Gly Gln
            100                 105                 110

Gly Thr Leu Val Thr Val Ser Ser
        115                 120

<210> SEQ ID NO 314
<211> LENGTH: 20
<212> TYPE: PRT
<213> ORGANISM: Artificial Sequence
<220> FEATURE:
<223> OTHER INFORMATION: synthetic

<400> SEQUENCE: 314

Ser Gly Gly Ser Gly Gly Gly Ser Gly Gly Ser Gly Gly
1               5                   10                  15

Gly Ser Leu Gln
        20

<210> SEQ ID NO 315
<211> LENGTH: 198
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(61)
<223> OTHER INFORMATION: human IL-15Ra Sushi domain (NM-002189)
<220> FEATURE:
<221> NAME/KEY: DOMAIN
<222> LOCATION: (62)..(64)
<223> OTHER INFORMATION: IRD-11exone3
<220> FEATURE:
<221> NAME/KEY: DOMAIN
<222> LOCATION: (65)..(84)
<223> OTHER INFORMATION: linker1
<220> FEATURE:
<221> NAME/KEY: DOMAIN
<222> LOCATION: (85)..(198)
<223> OTHER INFORMATION: human IL-15 (NM-000585-3)

<400> SEQUENCE: 315

Cys Pro Pro Pro Met Ser Val Glu His Ala Asp Ile Trp Val Lys Ser
1               5                   10                  15

Tyr Ser Leu Tyr Ser Arg Glu Arg Tyr Ile Cys Asn Ser Gly Phe Lys
            20                  25                  30

Arg Lys Ala Gly Thr Ser Ser Leu Thr Glu Cys Val Leu Asn Lys Ala
        35                  40                  45

-continued

```
Thr Asn Val Ala His Trp Thr Thr Pro Ser Leu Lys Cys Ile Arg Asp
 50                  55                  60

Ser Gly Gly Ser Gly Gly Gly Ser Gly Gly Ser Gly Gly Gly
 65                  70                  75                  80

Gly Ser Leu Gln Asn Trp Val Asn Val Ile Ser Asp Leu Lys Lys Ile
                 85                  90                  95

Glu Asp Leu Ile Gln Ser Met His Ile Asp Ala Thr Leu Tyr Thr Glu
            100                 105                 110

Ser Asp Val His Pro Ser Cys Lys Val Thr Ala Met Lys Cys Phe Leu
            115                 120                 125

Leu Glu Leu Gln Val Ile Ser Leu Glu Ser Gly Asp Ala Ser Ile His
130                 135                 140

Asp Thr Val Glu Asn Leu Ile Ile Leu Ala Asn Asn Ser Leu Ser Ser
145                 150                 155                 160

Asn Gly Asn Val Thr Glu Ser Gly Cys Lys Glu Cys Glu Glu Leu Glu
                165                 170                 175

Glu Lys Asn Ile Lys Glu Phe Leu Gln Ser Phe Val His Ile Val Gln
            180                 185                 190

Met Phe Ile Asn Thr Ser
            195
```

<210> SEQ ID NO 316
<211> LENGTH: 25
<212> TYPE: PRT
<213> ORGANISM: Artificial Sequence
<220> FEATURE:
<223> OTHER INFORMATION: synthetic

<400> SEQUENCE: 316

```
Ser Gly Gly Gly Gly Ser Gly Gly Gly Gly Ser Gly Gly Gly Gly Ser
 1               5                  10                  15

Gly Gly Gly Gly Ser Gly Gly Gly Gly
                20                  25
```

<210> SEQ ID NO 317
<211> LENGTH: 203
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(61)
<223> OTHER INFORMATION: human ILL-15Ra Sushi domain (NM-002189)
<220> FEATURE:
<221> NAME/KEY: DOMAIN
<222> LOCATION: (62)..(64)
<223> OTHER INFORMATION: human IL-15Ra Sushi domain (NM-002189)
     IRD-11exone3
<220> FEATURE:
<221> NAME/KEY: DOMAIN
<222> LOCATION: (65)..(89)
<223> OTHER INFORMATION: linker2
<220> FEATURE:
<221> NAME/KEY: DOMAIN
<222> LOCATION: (90)..(203)
<223> OTHER INFORMATION: human IL-15 (NM-000585-3)

<400> SEQUENCE: 317

```
Cys Pro Pro Pro Met Ser Val Glu His Ala Asp Ile Trp Val Lys Ser
 1               5                  10                  15

Tyr Ser Leu Tyr Ser Arg Glu Arg Tyr Ile Cys Asn Ser Gly Phe Lys
                20                  25                  30
```

-continued

Arg Lys Ala Gly Thr Ser Ser Leu Thr Glu Cys Val Leu Asn Lys Ala
                35                  40                  45

Thr Asn Val Ala His Trp Thr Thr Pro Ser Leu Lys Cys Ile Arg Asp
 50                  55                  60

Ser Gly Gly Gly Ser Gly Gly Gly Ser Gly Gly Gly Ser
 65                  70                  75                  80

Gly Gly Gly Gly Ser Gly Gly Gly Asn Trp Val Asn Val Ile Ser
                 85                  90                  95

Asp Leu Lys Lys Ile Glu Asp Leu Ile Gln Ser Met His Ile Asp Ala
                100                 105                 110

Thr Leu Tyr Thr Glu Ser Asp Val His Pro Ser Cys Lys Val Thr Ala
            115                 120                 125

Met Lys Cys Phe Leu Leu Glu Leu Gln Val Ile Ser Leu Glu Ser Gly
130                 135                 140

Asp Ala Ser Ile His Asp Thr Val Glu Asn Leu Ile Ile Leu Ala Asn
145                 150                 155                 160

Asn Ser Leu Ser Ser Asn Gly Asn Val Thr Glu Ser Gly Cys Lys Glu
                165                 170                 175

Cys Glu Glu Leu Glu Glu Lys Asn Ile Lys Glu Phe Leu Gln Ser Phe
            180                 185                 190

Val His Ile Val Gln Met Phe Ile Asn Thr Ser
            195                 200

<210> SEQ ID NO 318
<211> LENGTH: 30
<212> TYPE: PRT
<213> ORGANISM: Artificial Sequence
<220> FEATURE:
<223> OTHER INFORMATION: synthetic

<400> SEQUENCE: 318

Ser Gly Gly Gly Ser Gly Gly Gly Ser Gly Gly Gly Ser
1               5                   10                  15

Gly Gly Gly Gly Ser Gly Gly Gly Ser Gly Gly Gly Gly
            20                  25                  30

<210> SEQ ID NO 319
<211> LENGTH: 208
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(61)
<223> OTHER INFORMATION: human ILL-15Ra Sushi domain (NM-002189)
<220> FEATURE:
<221> NAME/KEY: DOMAIN
<222> LOCATION: (62)..(64)
<223> OTHER INFORMATION: IRD-11exone3
<220> FEATURE:
<221> NAME/KEY: DOMAIN
<222> LOCATION: (65)..(94)
<223> OTHER INFORMATION: linker3
<220> FEATURE:
<221> NAME/KEY: DOMAIN
<222> LOCATION: (95)..(208)
<223> OTHER INFORMATION: human IL-15 (NM-000585-3)

<400> SEQUENCE: 319

Cys Pro Pro Pro Met Ser Val Glu His Ala Asp Ile Trp Val Lys Ser
1               5                   10                  15

Tyr Ser Leu Tyr Ser Arg Glu Arg Tyr Ile Cys Asn Ser Gly Phe Lys

```
                    20                  25                  30
Arg Lys Ala Gly Thr Ser Ser Leu Thr Glu Cys Val Leu Asn Lys Ala
                35                  40                  45

Thr Asn Val Ala His Trp Thr Thr Pro Ser Leu Lys Cys Ile Arg Asp
        50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Ser Gly Gly Gly Asn Trp
                85                  90                  95

Val Asn Val Ile Ser Asp Leu Lys Lys Ile Glu Asp Leu Ile Gln Ser
                100                 105                 110

Met His Ile Asp Ala Thr Leu Tyr Thr Glu Ser Asp Val His Pro Ser
            115                 120                 125

Cys Lys Val Thr Ala Met Lys Cys Phe Leu Leu Glu Leu Gln Val Ile
        130                 135                 140

Ser Leu Glu Ser Gly Asp Ala Ser Ile His Asp Thr Val Glu Asn Leu
145                 150                 155                 160

Ile Ile Leu Ala Asn Asn Ser Leu Ser Ser Asn Gly Asn Val Thr Glu
                165                 170                 175

Ser Gly Cys Lys Glu Cys Glu Glu Leu Glu Glu Lys Asn Ile Lys Glu
            180                 185                 190

Phe Leu Gln Ser Phe Val His Ile Val Gln Met Phe Ile Asn Thr Ser
        195                 200                 205

<210> SEQ ID NO 320
<211> LENGTH: 40
<212> TYPE: PRT
<213> ORGANISM: Artificial Sequence
<220> FEATURE:
<223> OTHER INFORMATION: synthetic

<400> SEQUENCE: 320

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
                20                  25                  30

Gly Gly Gly Ser Gly Gly Gly Gly
        35                  40

<210> SEQ ID NO 321
<211> LENGTH: 218
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(61)
<223> OTHER INFORMATION: human ILL-15Ra Sushi domain (NM-002189)
<220> FEATURE:
<221> NAME/KEY: DOMAIN
<222> LOCATION: (62)..(64)
<223> OTHER INFORMATION: IRD-11exone3
<220> FEATURE:
<221> NAME/KEY: DOMAIN
<222> LOCATION: (65)..(104)
<223> OTHER INFORMATION: linker4
<220> FEATURE:
<221> NAME/KEY: DOMAIN
<222> LOCATION: (105)..(218)
<223> OTHER INFORMATION: human IL-15 (NM-000585-3)

<400> SEQUENCE: 321
```

Cys Pro Pro Pro Met Ser Val Glu His Ala Asp Ile Trp Val Lys Ser
1               5                   10                  15

Tyr Ser Leu Tyr Ser Arg Glu Arg Tyr Ile Cys Asn Ser Gly Phe Lys
            20                  25                  30

Arg Lys Ala Gly Thr Ser Ser Leu Thr Glu Cys Val Leu Asn Lys Ala
        35                  40                  45

Thr Asn Val Ala His Trp Thr Thr Pro Ser Leu Lys Cys Ile Arg Asp
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Ser Gly Gly Gly Gly Ser Gly
                85                  90                  95

Gly Gly Gly Ser Gly Gly Gly Gly Asn Trp Val Asn Val Ile Ser Asp
            100                 105                 110

Leu Lys Lys Ile Glu Asp Leu Ile Gln Ser Met His Ile Asp Ala Thr
        115                 120                 125

Leu Tyr Thr Glu Ser Asp Val His Pro Ser Cys Lys Val Thr Ala Met
    130                 135                 140

Lys Cys Phe Leu Leu Glu Leu Gln Val Ile Ser Leu Glu Ser Gly Asp
145                 150                 155                 160

Ala Ser Ile His Asp Thr Val Glu Asn Leu Ile Ile Leu Ala Asn Asn
                165                 170                 175

Ser Leu Ser Ser Asn Gly Asn Val Thr Glu Ser Gly Cys Lys Glu Cys
            180                 185                 190

Glu Glu Leu Glu Glu Lys Asn Ile Lys Glu Phe Leu Gln Ser Phe Val
        195                 200                 205

His Ile Val Gln Met Phe Ile Asn Thr Ser
    210                 215

<210> SEQ ID NO 322
<211> LENGTH: 50
<212> TYPE: PRT
<213> ORGANISM: Artificial Sequence
<220> FEATURE:
<223> OTHER INFORMATION: synthetic

<400> SEQUENCE: 322

Ser Gly Gly Gly Gly Ser Gly Gly Gly Gly Ser Gly Gly Gly Gly Ser
1               5                   10                  15

Gly Gly Gly Gly Ser Gly Gly Gly Ser Gly Gly Gly Gly Ser Gly
            20                  25                  30

Gly Gly Gly Ser Gly Gly Gly Gly Ser Gly Gly Gly Gly Ser Gly Gly
        35                  40                  45

Gly Gly
    50

<210> SEQ ID NO 323
<211> LENGTH: 228
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(61)
<223> OTHER INFORMATION: human ILL-15Ra Sushi domain (NM-002189)
<220> FEATURE:
<221> NAME/KEY: DOMAIN
<222> LOCATION: (62)..(64)

```
<223> OTHER INFORMATION: IRD-11exone3
<220> FEATURE:
<221> NAME/KEY: DOMAIN
<222> LOCATION: (65)..(114)
<223> OTHER INFORMATION: linker5
<220> FEATURE:
<221> NAME/KEY: DOMAIN
<222> LOCATION: (115)..(228)
<223> OTHER INFORMATION: human IL-15 (NM-000585-3)

<400> SEQUENCE: 323

Cys Pro Pro Pro Met Ser Val Glu His Ala Asp Ile Trp Val Lys Ser
1               5                   10                  15

Tyr Ser Leu Tyr Ser Arg Glu Arg Tyr Ile Cys Asn Ser Gly Phe Lys
            20                  25                  30

Arg Lys Ala Gly Thr Ser Ser Leu Thr Glu Cys Val Leu Asn Lys Ala
        35                  40                  45

Thr Asn Val Ala His Trp Thr Thr Pro Ser Leu Lys Cys Ile Arg Asp
    50                  55                  60

Ser Gly Gly Gly Ser Gly Gly Gly Ser Gly Gly Gly Ser
65                  70                  75                  80

Gly Gly Gly Gly Ser Gly Gly Gly Ser Gly Gly Gly Ser Gly
            85                  90                  95

Gly Gly Ser Gly Gly Gly Ser Gly Gly Gly Ser Gly Gly
        100                 105                 110

Gly Gly Asn Trp Val Asn Val Ile Ser Asp Leu Lys Lys Ile Glu Asp
            115                 120                 125

Leu Ile Gln Ser Met His Ile Asp Ala Thr Leu Tyr Thr Glu Ser Asp
130                 135                 140

Val His Pro Ser Cys Lys Val Thr Ala Met Lys Cys Phe Leu Leu Glu
145                 150                 155                 160

Leu Gln Val Ile Ser Leu Glu Ser Gly Asp Ala Ser Ile His Asp Thr
                165                 170                 175

Val Glu Asn Leu Ile Ile Leu Ala Asn Asn Ser Leu Ser Ser Asn Gly
            180                 185                 190

Asn Val Thr Glu Ser Gly Cys Lys Glu Cys Glu Glu Leu Glu Glu Lys
        195                 200                 205

Asn Ile Lys Glu Phe Leu Gln Ser Phe Val His Ile Val Gln Met Phe
    210                 215                 220

Ile Asn Thr Ser
225

<210> SEQ ID NO 324
<211> LENGTH: 18
<212> TYPE: PRT
<213> ORGANISM: Artificial Sequence
<220> FEATURE:
<223> OTHER INFORMATION: synthetic

<400> SEQUENCE: 324

Ser Gly Gly Ser Gly Gly Gly Ser Gly Gly Gly Ser Gly Gly Gly
1               5                   10                  15

Gly Ser

<210> SEQ ID NO 325
<211> LENGTH: 646
<212> TYPE: PRT
<213> ORGANISM: Artificial Sequence
<220> FEATURE:
<223> OTHER INFORMATION: synthetic
```

```
<220> FEATURE:
<221> NAME/KEY: DOMAIN
<222> LOCATION: (1)..(120)
<223> OTHER INFORMATION: tccLD7-102 heavy chain variable domain
<220> FEATURE:
<221> NAME/KEY: DOMAIN
<222> LOCATION: (121)..(449)
<223> OTHER INFORMATION: IgG1 CH1-CH2-CH3 domain
<220> FEATURE:
<221> NAME/KEY: DOMAIN
<222> LOCATION: (450)..(646)
<223> OTHER INFORMATION: deSD15-20

<400> SEQUENCE: 325
```

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly |
| 1 | | | | 5 | | | | | 10 | | | | | 15 |
| Gly | Ser | Leu | Arg | Leu | Ser | Cys | Ala | Ala | Ser | Gly | Phe | Thr | Phe | Ser |
| | | | 20 | | | | | 25 | | | | | 30 | |
| Ala | Tyr | Arg | Met | Phe | Trp | Val | Arg | Gln | Ala | Pro | Gly | Lys | Gly | Leu |
| | | | 35 | | | | | 40 | | | | | 45 | |
| Glu | Trp | Val | Ser | Ser | Ile | Tyr | Pro | Ser | Gly | Gly | Ile | Thr | Phe | Tyr |
| | | | 50 | | | | | 55 | | | | | 60 | |
| Ala | Asp | Ser | Val | Lys | Gly | Arg | Phe | Thr | Ile | Ser | Arg | Asp | Asn | Ser |
| 65 | | | | | 70 | | | | | 75 | | | | | 80 |
| Lys | Asn | Thr | Leu | Tyr | Leu | Gln | Met | Asn | Ser | Leu | Arg | Ala | Glu | Asp |
| | | | | 85 | | | | | 90 | | | | | 95 |
| Thr | Ala | Ile | Tyr | Tyr | Cys | Ala | Arg | Ile | Lys | Leu | Gly | Thr | Val | Thr |
| | | | | 100 | | | | | 105 | | | | | 110 |
| Val | Asp | Tyr | Trp | Gly | Gln | Gly | Thr | Leu | Val | Thr | Val | Ser | Ser | Ala |
| | | | | 115 | | | | | 120 | | | | | 125 |
| Ser | Thr | Lys | Gly | Pro | Ser | Val | Phe | Pro | Leu | Ala | Pro | Ser | Ser | Lys |
| | | | | 130 | | | | | 135 | | | | | 140 |
| Ser | Thr | Ser | Gly | Gly | Thr | Ala | Ala | Leu | Gly | Cys | Leu | Val | Lys | Asp |
| 145 | | | | | 150 | | | | | 155 | | | | | 160 |
| Tyr | Phe | Pro | Glu | Pro | Val | Thr | Val | Ser | Trp | Asn | Ser | Gly | Ala | Leu |
| | | | | 165 | | | | | 170 | | | | | 175 |
| Thr | Ser | Gly | Val | His | Thr | Phe | Pro | Ala | Val | Leu | Gln | Ser | Ser | Gly |
| | | | | 180 | | | | | 185 | | | | | 190 |
| Leu | Tyr | Ser | Leu | Ser | Ser | Val | Val | Thr | Val | Pro | Ser | Ser | Ser | Leu |
| | | | | 195 | | | | | 200 | | | | | 205 |
| Gly | Thr | Gln | Thr | Tyr | Ile | Cys | Asn | Val | Asn | His | Lys | Pro | Ser | Asn |
| | | | | 210 | | | | | 215 | | | | | 220 |
| Thr | Lys | Val | Asp | Lys | Arg | Val | Glu | Pro | Lys | Ser | Cys | Asp | Lys | Thr |
| 225 | | | | | 230 | | | | | 235 | | | | | 240 |
| His | Thr | Cys | Pro | Pro | Cys | Pro | Ala | Pro | Glu | Leu | Leu | Gly | Gly | Pro |
| | | | | 245 | | | | | 250 | | | | | 255 |
| Ser | Val | Phe | Leu | Phe | Pro | Pro | Lys | Pro | Lys | Asp | Thr | Leu | Met | Ile |
| | | | | 260 | | | | | 265 | | | | | 270 |
| Ser | Arg | Thr | Pro | Glu | Val | Thr | Cys | Val | Val | Val | Asp | Val | Ser | His |
| | | | | 275 | | | | | 280 | | | | | 285 |
| Glu | Asp | Pro | Glu | Val | Lys | Phe | Asn | Trp | Tyr | Val | Asp | Gly | Val | Glu |
| | | | | 290 | | | | | 295 | | | | | 300 |
| Val | His | Asn | Ala | Lys | Thr | Lys | Pro | Arg | Glu | Glu | Gln | Tyr | Asn | Ser |
| 305 | | | | | 310 | | | | | 315 | | | | | 320 |
| Thr | Tyr | Arg | Val | Val | Ser | Val | Leu | Thr | Val | Leu | His | Gln | Asp | Trp |
| | | | | 325 | | | | | 330 | | | | | 335 |
| Leu | Asn | Gly | Lys | Glu | Tyr | Lys | Cys | Lys | Val | Ser | Asn | Lys | Ala | Leu |
| | | | | | | | | | | | | | | |
| Pro | Ala | Pro | Ile | Glu | Lys | Thr | Ile | Ser | Lys | Ala | Lys | Gly | Gln | Pro |
| Arg | Glu | Pro | Gln | Val | Tyr | | | | | | | | | |

```
            340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly Ser Cys Pro Pro Pro Met Ser Val Glu His Ala Asp Ile Trp Val
            450                 455                 460
Lys Ser Tyr Ser Leu Tyr Ser Arg Glu Arg Tyr Ile Cys Asn Ser Gly
465                 470                 475                 480
Phe Lys Arg Lys Ala Gly Thr Ser Ser Leu Thr Glu Cys Val Leu Asn
                485                 490                 495
Lys Ala Thr Asn Val Ala His Trp Thr Thr Pro Ser Leu Lys Cys Ile
            500                 505                 510
Arg Asp Ser Gly Gly Ser Gly Gly Gly Ser Gly Gly Gly Ser Gly
            515                 520                 525
Gly Gly Gly Ser Asn Trp Val Asn Val Ile Ser Asp Leu Lys Lys Ile
            530                 535                 540
Glu Asp Leu Ile Gln Ser Met His Ile Asp Ala Thr Leu Tyr Thr Glu
545                 550                 555                 560
Ser Asp Val His Pro Ser Cys Lys Val Thr Ala Met Lys Cys Phe Leu
                565                 570                 575
Leu Glu Leu Gln Val Ile Ser Leu Glu Ser Gly Asp Ala Ser Ile His
            580                 585                 590
Asp Thr Val Glu Asn Leu Ile Ile Leu Ala Asn Asn Ser Leu Ser Ser
            595                 600                 605
Asn Gly Asn Val Thr Glu Ser Gly Cys Lys Glu Cys Glu Glu Leu Glu
            610                 615                 620
Glu Lys Asn Ile Lys Glu Phe Leu Gln Ser Phe Val His Ile Val Gln
625                 630                 635                 640
Met Phe Ile Asn Thr Ser
                645

<210> SEQ ID NO 326
<211> LENGTH: 216
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(113)
<223> OTHER INFORMATION: VL
<220> FEATURE:
<221> NAME/KEY: DOMAIN
<222> LOCATION: (114)..(216)
<223> OTHER INFORMATION: CL

<400> SEQUENCE: 326

Gln Ser Ala Leu Thr Gln Pro Ala Ser Val Ser Gly Ser Pro Gly Gln
1               5                   10                  15
```

```
Ser Ile Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 327
<211> LENGTH: 215
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(113)
<223> OTHER INFORMATION: VL
<220> FEATURE:
<221> NAME/KEY: DOMAIN
<222> LOCATION: (114)..(215)
<223> OTHER INFORMATION: CL w/ C-terminal serine deleted

<400> SEQUENCE: 327

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110
```

```
Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145             150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys
    210                 215

<210> SEQ ID NO 328
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: (1)..(1)
<223> OTHER INFORMATION: residue is A G M Q S Y or W
<220> FEATURE:
<221> NAME/KEY: VARIANT
<222> LOCATION: (3)..(3)
<223> OTHER INFORMATION: residue is A L M Q R S V W or Y
<220> FEATURE:
<221> NAME/KEY: VARIANT
<222> LOCATION: (5)..(5)
<223> OTHER INFORMATION: residue is A F L M S T V or Y

<400> SEQUENCE: 328

Xaa Tyr Xaa Met Xaa
1               5
```